US010844118B2

(12) United States Patent
Winau et al.

(10) Patent No.: US 10,844,118 B2
(45) Date of Patent: Nov. 24, 2020

(54) TREATMENT OF INFLAMMATORY SKIN DISEASE

(71) Applicant: CHILDREN'S MEDICAL CENTER CORPORATION, Boston, MA (US)

(72) Inventors: Florian E. Winau, Boston, MA (US); Ji Hyung Kim, Brookline, MA (US)

(73) Assignee: CHILDREN'S MEDICAL CENTER CORPORATION, Boston, MA (US)

( * ) Notice: Subject to any disclaimer, the term of this patent is extended or adjusted under 35 U.S.C. 154(b) by 905 days.

(21) Appl. No.: 15/023,283

(22) PCT Filed: Sep. 17, 2014

(86) PCT No.: PCT/US2014/056021
§ 371 (c)(1),
(2) Date: Mar. 18, 2016

(87) PCT Pub. No.: WO2015/042110
PCT Pub. Date: Mar. 26, 2015

(65) Prior Publication Data
US 2016/0229912 A1  Aug. 11, 2016

Related U.S. Application Data

(60) Provisional application No. 61/880,522, filed on Sep. 20, 2013.

(51) Int. Cl.
| | | |
|---|---|---|
| *A61K 39/00* | (2006.01) | |
| *C07K 16/28* | (2006.01) | |
| *A61K 31/713* | (2006.01) | |
| *A61K 31/05* | (2006.01) | |
| *G01N 33/50* | (2006.01) | |
| *A61K 9/00* | (2006.01) | |
| *A61K 31/04* | (2006.01) | |
| *A61K 31/437* | (2006.01) | |
| *A61K 39/395* | (2006.01) | |

(52) U.S. Cl.
CPC ........ *C07K 16/2803* (2013.01); *A61K 9/0014* (2013.01); *A61K 9/0019* (2013.01); *A61K 31/04* (2013.01); *A61K 31/05* (2013.01); *A61K 31/437* (2013.01); *A61K 31/713* (2013.01); *A61K 39/3955* (2013.01); *G01N 33/5044* (2013.01); *G01N 33/5047* (2013.01); *A61K 2039/505* (2013.01); *C07K 2317/76* (2013.01); *G01N 2333/70539* (2013.01); *G01N 2800/202* (2013.01)

(58) Field of Classification Search
None
See application file for complete search history.

(56) References Cited

U.S. PATENT DOCUMENTS 7,968,092 B2 * 6/2011 Throsby ............. C07K 16/2833
424/142.1

| 2006/0257397 A1 | 11/2006 | Throsby et al. |
| 2009/0203586 A1 | 8/2009 | Dearman et al. |
| 2011/0038860 A1 | 2/2011 | Zeng et al. |

FOREIGN PATENT DOCUMENTS

| WO | 2005063819 A2 | 7/2005 |
| WO | WO2005063819 A2 * | 7/2005 |

OTHER PUBLICATIONS

Edwards et al (JMB, 2003, 334: 103-118) (Year: 2003).*
Lloyd et al (Protein Engineering, Eng. Design & Selection, 2009, 22(3): 159-168) (Year: 2009).*
Goel et al (J. Immunol., 2004, 173: 7358-7367) (Year: 2004).*
Khan and Salunke (J. Immunol, 2014, 192: 5398-5405) (Year: 2014).*
Poosarla et al (Biotechn. Bioeng., 2017, 114(6): 1331-1342) (Year: 2017).*
Torres and Casadevall (Trend. Immunol., 2008, 29(2): 91-97) (Year: 2008).*
Johnson-Huang et al (J. Clin. Immunol. 2009, 29: 247-256) (Year: 2009).*
Lauren et al (TRENDS in Immunol. 2003, 24(4): 190-196) (Year: 2003).*
Hussein, "Evaluation of Langerhans' cells in normal and eczematous dermatitis skin by CD1a protein immunohistochemistry: preliminary findings", J Cutan Pathol 35(6) 554-558 (2008).
Lam et al., "Rapid and Efficient Differentiation of Human Pluripotent Stem Cells into Intermediate Mesoderm That Forms Tubules Expressing Kidney Proximal Tubular Markers" J Am Soc Nephrol 25(6):1211-1225 (2014).
Brigl et al., "CD1: Antigen Presentation and T Cell Function", Annu. Rev. Immunol. 22:817-890 (2004).
Duhen et al., "Production of interleukin 22 but not interleukin 17 by a subset of human skin-homing memory T cells", Nature Immunology 10(8):857-863 (2009).
Moody, "The Surprising Diversity of Lipid Antigens for CD1-Restricted T Cells", Advances in Immunology 89:87-139 (2006).
Bashir et al., "Pollen Lipidomics: Lipid Profiling Exposes a Notable Diversity in 22 Allergenic Pollen and Potential Biomarkers of the Allergic Immune Response", PLoS One 8(2):e57566 (2013).
Boniface et al., "A role for T cell-derived interleukin 22 in psoriatic skin inflammation", Clin. Exp. Immunol. 150:407-415 (2007).
Boyman et al., "Spontaneous Development of Psoriasis in a New Animal Model Shows an Essential Role for Resident T Cells and Tumor Necrosis Factor-alpha", J. Exp. Med. 199(5):731-736 (2004).
Cohen et al., "Antigen Presentation by CD1: Lipids, T Cells and NKT Cells in Microbial Immunity", Advances in Immunology 102:1-94 (2009).

(Continued)

*Primary Examiner* — G. R. Ewoldt
*Assistant Examiner* — Marianne DiBrino
(74) *Attorney, Agent, or Firm* — Nixon Peabody LLP; David S. Resnick; Teresa A. Ptashka

(57) ABSTRACT

The methods, compositions, and assays described herein are based, in part, on the discovery that CD1a mediates inflammation related to certain conditions such as urushiol exposure, psoriasis and other inflammatory skin diseases. One aspect provided herein relates to a method for treating or preventing an inflammatory skin disease, the method comprising: administering a therapeutically effective amount of an inhibitor of CD 1a to a subject having an inflammatory skin disease, thereby treating or preventing the inflammatory skin diseases.

2 Claims, 21 Drawing Sheets
Specification includes a Sequence Listing.

(56) References Cited

OTHER PUBLICATIONS

Colonna, "Skin function for human CD1a-reactive T cells", Nature Immunology 11(12):1079-1080 (2010).
De Lalla et al., "High-frequency and adpative-like dynamics of human CD1 self-reactive T cells", Eur. J. Immunol., 41 (3):602-610 (2011).
Fujita et al., "Human Langerhans cells induce distinct IL-22-producing CD4+ T cells lacking IL-17 production", PNAS 106(51):21795-21800 (2009).
Hunger et al., "Langerhans cells utilize CD1a and langerin to efficiently present nonpeptide antigens to T cells", J. Clin. Invest. 113(5):701-708 (2004).
De Jong et al., "CD1a-autoreactive T cells are a normal component of the human alphabeta T cell repertoire", Nat. Immunol. 11(12):1102-1109 (2010).
Pena-Cruz et al., "Epidermal Langerhans Cells Efficiently Mediate CD1a-Dependent Presentation of Microbial Lipid Antigens to T cells", J. Invest Dermatol. 121(3):517-521 (2003).

\* cited by examiner

TREATMENT OF INFLAMMATORY SKIN DISEASE

CROSS REFERENCE TO RELATED APPLICATION

This application is a 35 U.S.C. § 371 National Phase Entry Application of International Application No. PCT/US2014/056021 filed Sep. 17, 2014, which designates the U.S. and claims benefit under 35 U.S.C. § 119(e) of U.S. Provisional Patent Application Ser. No. 61/880,522, filed Sep. 20, 2013, the contents of which are herein incorporated by reference in their entirety.

GOVERNMENT SUPPORT

This invention was made with government support under Grant Numbers AI122291, AI127766, AI083426, and AI136937 awarded by the National Institutes of Health. The Government has certain rights in the invention.

SEQUENCE LISTING

The instant application contains a Sequence Listing which has been filed electronically in ASCII format and is hereby incorporated by reference in its entirety. Said ASCII copy, created on Aug. 30, 2019, is named 701039-078732-US_SL.txt and is 167,557 bytes in size.

TECHNICAL FIELD

The technical field relates to the compositions and methods for the treatment of inflammatory skin diseases. The field also relates to screening assays for agents the treatment of inflammatory skin diseases.

BACKGROUND

Various skin conditions are associated with increased T cell activation and abnormal antigen presentation in the dermis and epidermis. For example, in contact allergic dermatitis, activation of intracutaneous T-cells is observed. It is known that skin from patients exhibiting atopic dermatitis contains an increased number of Langerhans cells. In psoriatic skin, there is an increased number of antigen presenting cells, composed of both Langerhans cells and non-Langerhans cell Class II MHC-bearing antigen presenting cells.

T cells play a major role in the immune response by interacting with target and antigen presenting cells. For example, T cell-mediated killing of target cells is a multi-step process involving, initially, adhesion of cytolytic T cells (the effector cells) to target cells. Also, helper T cells help initiate the immune response by adhesion to antigen presenting cells.

These interactions of T cells with target and antigen presenting cells are highly specific and depend on the recognition of an antigen on the surface of a target or antigen presenting cell by one of the many specific antigen receptors on the surface of T cells.

One way in which T cells are activated is by binding of their antigen specific T cell receptors to peptide-MHC complexes on the surface of antigen presenting cells such as macrophages. T cell activation stimulates proliferation and differentiation of two types of functional T cells: helper cells, which promote the proliferation and maturation of antibody-producing B lymphocytes, and killer cells, which lyse target cells.

CD1 proteins are a family of transmembrane glycoproteins that mediate the presentation of lipid and glycolipid antigens of self or microbial origin to T cells in a manner similar to MHC Class I molecules. CD1a molecules are found primarily on Langerhans cells, which are the major dendritic antigen-presenting cells in the skin.

SUMMARY

The methods, compositions, and assays described herein are based, in part, on the discovery that CD1a mediates inflammation related to certain conditions such as urushiol exposure (e.g., poison oak, poison ivy, and poison sumac), psoriasis and atopic dermatitis. Further, the inventors have discovered that inhibitors of CD1a are effective to therapeutically treat or prevent these and other inflammatory skin diseases.

One aspect provided herein relates to a method for treating or preventing an inflammatory skin disease, the method comprising: administering a therapeutically effective amount of an inhibitor of CD1a to a subject having an inflammatory skin disease, thereby treating or preventing the inflammatory skin diseases.

In one embodiment of this aspect and all other aspects described herein, the inhibitor of CD1a inhibits CD1a expression and/or activity.

In another embodiment of this aspect and all other aspects described herein, the inhibitor of CD1a expression is an RNA interference molecule or a small molecule.

In another embodiment of this aspect and all other aspects described herein, the inhibitor of CD1a activity is a small molecule, an antibody or fragment thereof, or a peptide.

In one embodiment of this aspect and all other aspects described herein, the inhibitor of CD1a is a human binding molecule against CD1a as described in U.S. Pat. No. 7,968,092, the contents are incorporated here in reference in its entirety.

In another embodiment of this aspect and all other aspects described herein, the inflammatory skin disease is a T-cell mediated skin disease or disorder.

In another embodiment of this aspect and all other aspects described herein, the inflammatory skin disease is urushiol-induced contact dermatitis.

In another embodiment of this aspect and all other aspects described herein, the inflammatory skin disease is psoriasis and/or atopic dermatitis.

In another embodiment of this aspect and all other aspects described herein, the inhibitor of CD1a activity inhibits binding of a ligand to CD1a or CD1a-mediated antigen presenting activity.

In another embodiment of this aspect and all other aspects described herein, the ligand is urushiol.

In another embodiment of this aspect and all other aspects described herein, the inhibitor of CD1a activity inhibits antigen-presenting activity of a Langerhans cell.

Also provided herein in another aspect is a pharmaceutical composition for treating an inflammatory skin disease, the composition comprising a therapeutically effective amount of an inhibitor of CD1a and a pharmaceutically acceptable carrier.

In another embodiment of this aspect and all other aspects described herein, the inhibitor of CD1a is selected from the group consisting of: an RNA interference molecule, a small molecule, a peptide, and an antibody or fragment thereof.

In one embodiment of this aspect and all other aspects described herein, the composition comprises an inhibitor of CD1a that is a human binding molecule against CD1a as described in U.S. Pat. No. 7,968,092, the contents are incorporated here in reference in its entirety.

In another embodiment of this aspect and all other aspects described herein, the composition is formulated for systemic delivery.

In another embodiment of this aspect and all other aspects described herein, the composition is formulated for topical delivery.

Another aspect provided herein relates to a method for screening a candidate agent for treating an inflammatory skin disease, the method comprising: (a) contacting a Langerhans cell or population of Langerhans cells with an agent, (b) measuring expression and/or activity of CD1a in the cell or population of cells, wherein a decrease in expression and/or activity of CD1a indicates that the agent is a candidate agent for the treatment of an inflammatory skin disease.

In one embodiment of this aspect and all other aspects described herein, the candidate agent is selected from the group consisting of: an RNA interference molecule, a small molecule, a peptide, and an antibody or fragment thereof.

Also provided herein, in another aspect, is an assay comprising: (a) contacting a population of Langerhans cells with a candidate agent, (b) contacting the cells of step (a) with a labeled CD1a ligand, (c) measuring the intensity of the signal from the bound, detectable ligand, (d) comparing the measured intensity of the signal with a reference value and if the measured intensity is decreased relative to the reference value, (e) identifying the candidate agent as an inhibitor of CD1a expression and/or activity in the cell.

In one embodiment of this aspect and all other aspects described herein, the CD1a ligand is urushiol.

Another aspect provided herein relates to an inhibitor of CD1a for use in the treatment or prevention of an inflammatory skin disease.

Also provided herein, in another aspect, is a use of an inhibitor of CD1a for the manufacture of a medicament for the treatment or prevention of an inflammatory skin disease.

BRIEF DESCRIPTION OF THE FIGURES

FIG. 1A is a schematic depicting an exemplary interaction between urushiol and CD1a on the surface of a Langerhans cell and the immune response to poison ivy.

FIG. 1B shows that urushiol interacts as a ligand with a CD1a monomer in an in vitro plate-bound assay.

FIG. 2A shows an exemplary experimental protocol for treating CD1a-transgenic mice with urushiol.

FIG. 2B shows the degree of ear swelling in wild-type B6 and CD1a-transgenic mice treated with urushiol as shown in FIG. 2A.

FIG. 2C shows inflammatory granulocytes in the ears of urushiol-challenged mice.

FIG. 2D shows T-cell subsets in ears of urushiol-challenged mice.

FIG. 3A shows IL-17A and IFN-γ in urushiol-induced dermatitis.

FIG. 3B shows IL-17A CD4+ T-cell subsets in urushiol-induced dermatitis.

FIG. 3C shows IL-17A cytokine and IL-22 in urushiol-induced dermatitis.

FIG. 3D shows IL-17A/IL-22 CD4+ T-cell subsets in urushiol-induced dermatitis.

FIG. 4A shows data indicating that blocking CD1a abrogates skin inflammation.

FIG. 4B shows data indicating that inhibition of CD1a decreases neutrophil infiltration.

FIG. 4C shows data from CD1a-expressing cells in the ear and indicates that anti-CD1a depletes Langerhans cells in skin.

FIG. 4D shows data indicating that anti-CD1a treatment reduces IL-17A-producing CD4 T cells.

FIG. 5A shows that CD1a regulates the immune response to imiquimod (IMQ) as a model of psoriasis.

FIG. 5B shows that the psoriatic immune response is dependent on CD1a.

FIG. 5C shows that CD1a mediates a Th17-type response in psoriasis.

FIG. 6A shows the effect of anti-CD1a treatment on the degree of ear swelling in a mouse model of psoriasis.

FIG. 6B shows that CD1a therapy reduces T-cell infiltration in skin.

FIG. 6C shows that treatment with anti-CD1a abrogates Th17 phenotype in a psoriasis model.

FIG. 7A shows a schematic diagram depicting an exemplary experimental protocol for assessing response to DNFB in wildtype or CD1a-transgenic mice.

FIG. 7B shows the degree of ear swelling in wildtype and CD1a-transgenic mice treated with DNFB.

FIG. 7C shows data indicating that the immune response to DNFB is decreased in CD1a-transgenic mice.

FIG. 7D shows data indicating that CD1a modulates the generation of IFN-γ-producing CD8 T cells in response to haptens (DNFB).

FIG. 8A shows the increased in CD8+ and CD4+ markers in CD1a transgenic mice exposed to urushiol.

FIG. 8B shows the number of CD8+ and CD4+ T cells in CD1a transgenic mice exposed to urushiol.

FIG. 9A shows increased ear swelling in CD1a-transgenic mice that is abrogated by anti-CD1a injection. For CD1a blocking, 200 μg of anti-CD1a Ab was intraperitoneally injected into CD1a-transgenic mice every other day (−1, +1, +3, +5, and +7 days before and after MC903 treatment).

FIG. 9B shows reduction of CD11b+Gr-1+ inflammatory granulocytes in inflamed ear tissues by anti-CD1a Ab injection. For CD1a blocking, 200 μg of anti-CD1a Ab was intraperitoneally injected into CD1a-transgenic mice every other day (−1, +1, +3, +5, and +7 days before and after MC903 treatment).

DETAILED DESCRIPTION

Figure 1A:
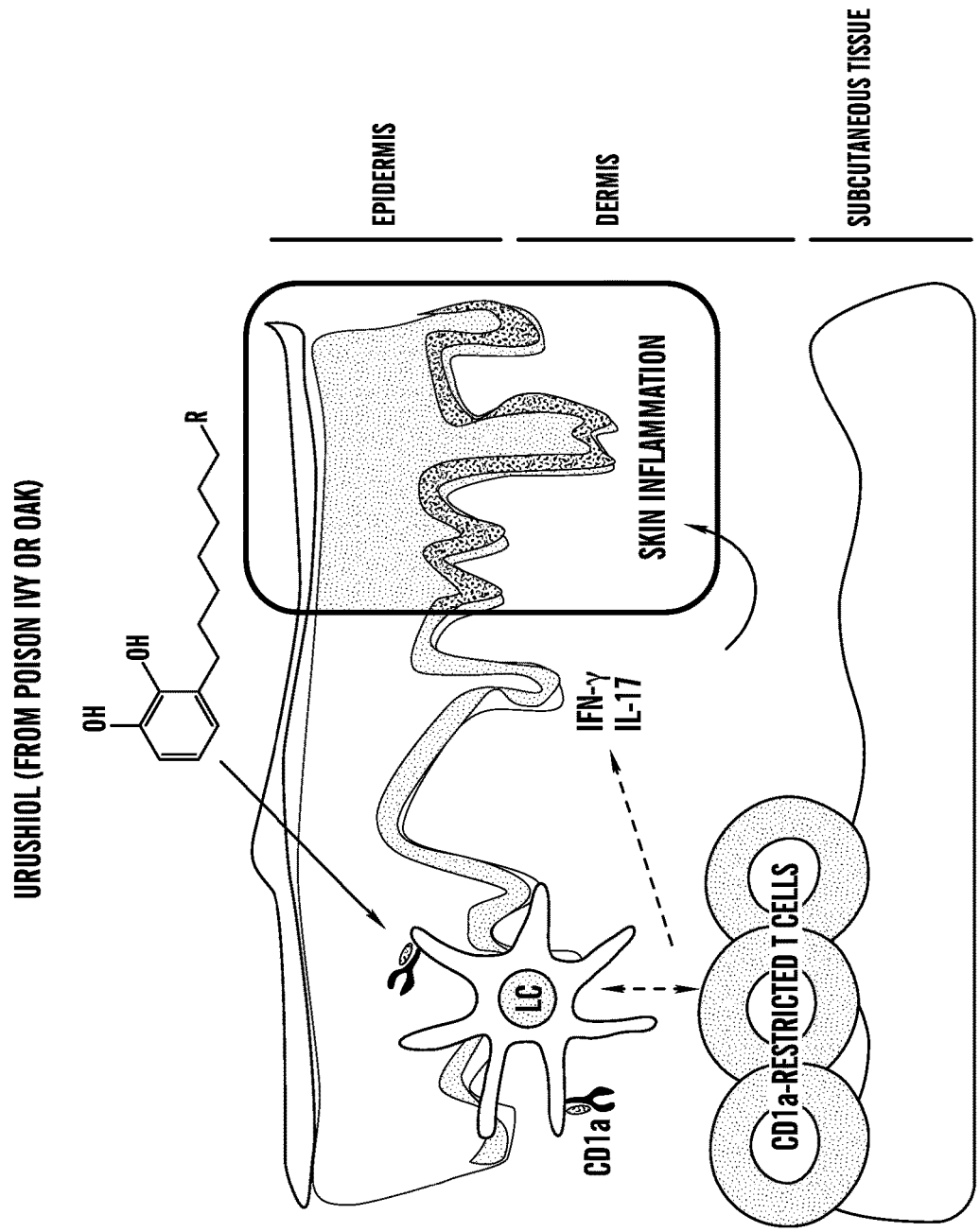
FIGS. 1A-1B show the interaction between CD1a and urushiol and the concept of the immune response to poison ivy.

The methods and assays described herein are based, in part, on the discovery that the molecule CD1a expressed on Langerhans cells in the skin participates in the generation of inflammatory skin diseases. Without wishing to be bound by theory, CD1a mediates an inflammatory T-cell response that is characterized by the prominent production of cytokines like IL-17. This forms the basis for a therapeutic treatment to target CD1a with specific antibodies, small molecule inhibitors, or RNAi to prevent, treat or even cure skin disease.

Definitions

As used herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder associated with an inflammatory skin disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but can also include a cessation or at least slowing of progress or worsening of symptoms that would be expected in absence of treatment. Beneficial or desired clinical results include, but are not limited to, alleviation of one or more symptom(s) of an inflammatory skin disease, diminishment of extent of the inflammatory skin disease, stabilized (i.e., not worsening) state of the inflammatory skin disease, delay or slowing of progression of the disease, amelioration or palliation of the inflammatory skin disease state, and remission (whether partial or total), whether detectable or undetectable. The term "treatment" of a disease also includes providing relief from the symptoms or side-effects of the disease (including palliative treatment).

In one embodiment, as used herein, the term "prevention" or "preventing" when used in the context of a subject refers to stopping, hindering, and/or slowing down the development of an immune disease and symptoms associated with the inflammatory skin disease.

As used herein, the term "therapeutically effective amount" means that amount necessary, at least partly, to attain the desired effect, or to delay the onset of, inhibit the progression of, or halt altogether, the onset or progression of the particular disease or disorder being treated (e.g., an inflammatory skin disease). Such amounts will depend, of course, on the particular condition being treated, the severity of the condition and individual patient parameters including age, physical condition, size, weight and concurrent treatment. These factors are well known to those of ordinary skill in the art and can be addressed with no more than routine experimentation. In some embodiments, a maximum dose of a therapeutic agent is used, that is, the highest safe dose according to sound medical judgment. It will be understood by those of ordinary skill in the art, however, that a lower dose or tolerable dose can be administered for medical reasons, psychological reasons or for virtually any other reason.

In one embodiment, a therapeutically effective amount of a pharmaceutical formulation, or a composition described herein for a method of treating an inflammatory skin disease is an amount of sufficient to reduce the level of at least one symptom of the inflammatory skin disease (e.g., pain, inflammation, itchiness, redness, pus, cytokine production, etc.) as compared to the level in the absence of the compound, the combination of compounds, the pharmaceutical composition/formulation or the composition. In other embodiments, the amount of the composition administered is preferably safe and sufficient to treat, delay the development of an inflammatory skin disease, and/or delay onset of the disease. In some embodiments, the amount can thus cure or result in amelioration of the symptoms of an inflammatory skin disease, slow the course of the disease, slow or inhibit a symptom of the disease, or slow or inhibit the establishment or development of secondary symptoms of the inflammatory skin disease. For example, an effective amount of a composition described herein inhibits further pain and/or inflammation associated with an inflammatory skin disease, cause a reduction in or even completely inhibit pain and/or inflammation associated with an inflammatory skin disease, even initiate complete regression of the disease, and reduce clinical symptoms associated with the inflammatory skin disease. In one embodiment, an effective amount for treating or ameliorating a disorder, disease, or medical condition is an amount sufficient to result in a reduction or complete removal of the symptoms of the disorder, disease, or medical condition. The effective amount of a given therapeutic agent will vary with factors such as the nature of the agent, the route of administration, the size and species of the animal to receive the therapeutic agent, and the purpose of the administration. Thus, it is not possible or prudent to specify an exact "therapeutically effective amount." However, for any given case, an appropriate "effective amount" can be determined by a skilled artisan according to established methods in the art using only routine experimentation.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g., the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level.

The term "statistically significant" or "significantly" refers to statistical significance and generally means a two standard deviation (2SD) below normal, or lower. The term refers to statistical evidence that there is a difference. It is defined as the probability of making a decision to reject the null hypothesis when the null hypothesis is actually true. The decision is often made using the p-value.

As used herein, the term "candidate agent" refers to a composition anticipated to reduce at least one symptom of an inflammatory skin disease by at least 10%, for example, a candidate agent can inhibit the interaction of CD1a with ligand, or can otherwise reduce the degree of inflammation, lesion size, appearance etc. of an inflammatory skin disease. Candidate agents can then be tested using the screening assays described herein using primary Langerhans cells to determine if the candidate agent can reproducibly cause a desired outcome and thereby be useful as an inhibitor of CD1a or a treatment for inflammatory skin disease in a subject.

A "nucleic acid", as described herein, can be RNA or DNA, and can be single or double stranded, and can be selected, for example, from a group including: nucleic acid encoding a protein of interest, oligonucleotides, nucleic acid analogues, for example peptide-nucleic acid (PNA), pseudo-complementary PNA (pc-PNA), locked nucleic acid (LNA) etc. Such nucleic acid sequences include, for example, but are not limited to, nucleic acid sequence encoding proteins, for example that act as transcriptional repressors, antisense molecules, ribozymes, small inhibitory nucleic acid sequences, for example but are not limited to RNAi, shRNAi, siRNA, micro RNAi (mRNAi), antisense oligonucleotides etc.

As used herein, the term "vector" refers to a nucleic acid molecule capable of transporting another nucleic acid to which it has been linked. One type of vector is a "plasmid", which refers to a circular double stranded DNA loop into which additional nucleic acid segments can be ligated. Another type of vector is a viral vector, wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors", or more simply "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, lentiviruses, adenoviruses and adeno-associated viruses), which serve equivalent functions. In one embodiment, lentiviruses are used to deliver one or more siRNA molecule of the present invention to a cell.

Within an expression vector, "operably linked" is intended to mean that the nucleotide sequence of interest is linked to the regulatory sequence(s) in a manner which allows for expression of the nucleotide sequence (e.g., in an in vitro transcription/translation system or in a target cell when the vector is introduced into the target cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). Furthermore, the RNA interfering agents can be delivered by way of a vector comprising a regulatory sequence to direct synthesis of the siRNAs of the invention at specific intervals, or over a specific time period. It will be appreciated by those skilled in the art that the design of the expression vector can depend on such factors as the choice of the target cell, the level of expression of siRNA desired, and the like.

The expression vectors of the invention can be introduced into target cells to thereby produce siRNA molecules of the present invention. In one embodiment, a DNA template, e.g., a DNA template encoding the siRNA molecule directed against CD1a, can be ligated into an expression vector under the control of RNA polymerase III (Pol III), and delivered to a target cell. Pol III directs the synthesis of small, noncoding transcripts which 3' ends are defined by termination within a stretch of 4-5 thymidines. Accordingly, DNA templates can be used to synthesize, in vivo, both sense and antisense strands of siRNAs which effect RNAi (Sui, et al. (2002) PNAS 99(8):5515).

The term "pharmaceutically acceptable" refers to compounds and compositions which can be administered to mammals without undue toxicity. The term "pharmaceutically acceptable carriers" excludes tissue culture medium. Exemplary pharmaceutically acceptable salts include but are not limited to mineral acid salts such as hydrochlorides, hydrobromides, phosphates, sulfates, and the like, and the salts of organic acids such as acetates, propionates, malonates, benzoates, and the like.

As used herein, the term "comprising" means that other elements can also be present in addition to the defined elements presented. The use of "comprising" indicates inclusion rather than limitation.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Further, unless otherwise required by context, singular terms shall include pluralities and plural terms shall include the singular.

Other than in the operating examples, or where otherwise indicated, all numbers expressing quantities of ingredients or reaction conditions used herein should be understood as modified in all instances by the term "about." The term "about" when used in connection with percentages can mean±1%.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

CD1a

CD1 proteins are a family of transmembrane glycoproteins that mediate the presentation of lipid and glycolipid antigens of self or microbial origin to T cells in a manner similar to MHC Class I molecules. CD1a molecules are found primarily on Langerhans cells, which are the major dendritic antigen-presenting cells in the skin.

The CD1 proteins are typically expressed on the surfaces of dendritic cells, monocytes, and thymocytes. The family of CD1 molecules is homologous to MHC-I and also functions in antigen presentation (Brigl, M. & Brenner, M. B. *Annu. Rev. Immunol.* 22, 817-890 (2004)). In contrast to peptide presentation by MHC, CD1 proteins present lipid antigens to T cells (Cohen, N. R et al. *Adv. Immunol.* 102, 1-94 (2009)). Based on sequence homology, CD1 molecules are segregated in group 1 (CD1a-c) and group 2 (CD1d). Whereas CD1d stimulates the invariant population of NKT cells, group 1 CD1 molecules activate polyclonal T lymphocytes with a diverse T cell receptor (TCR) repertoire (Bendelac, A., et al. *Annu. Rev. Immunol.* 25, 297-336 (2007), Strominger, J. L. *J. Immunol.* 184, 3303-3305 (2010)). TCR diversity is also reflected in the functional mode of activation, with NKT cells responding like innate-like lymphocytes and group 1 CD1-restricted T cells rather behaving like T cells of the adaptive immune system (Cohen, N. R et al. *Adv. Immunol.* 102, 1-94 (2009), Darmoise, A. et al. *Immunity.* 33, 216-228 (2010)). Whereas CD1d and NKT cells are present in all mammalian organisms, CD1a-c are mainly expressed in humans and lack in mice. Thus, analysis of group 1 CD1-restricted T cells is limited to in vitro experiments with patient-derived lymphocytes from peripheral blood. Consequently, definition of the in vivo functions of those cells remains elusive.

However, the described functions of group 1 CD1-restricted T cells indicate that they have an important role in human immunology (Brigl, M. & Brenner, M. B. Annu. Rev. Immunol. 22, 817-890 (2004)). Accordingly, CD1a, b, and c molecules can present exogenous lipid antigens from pathogens such as *Mycobacterium tuberculosis* to subsequently activate T cells in infection (Cohen, N. R et al. *Adv. Immunol.* 102, 1-94 (2009)). In addition, T cells recognize self-lipids displayed by CD1a-c, indicating their potential autoreactivity (Moody, D. B. *Adv. Immunol.* 89, 87-139 (2006)). Indeed, previous studies demonstrated that T cells reactive with CD1a are highly abundant in peripheral blood and represent a physiologic component of the human T cell population (de Jong, A. et al. *Nat. Immunol.* 11, 1102-1109 (2010), de Lalla, C. et al. *Eur. J. Immunol.* 41, 602-610 (2011)). Notably, these CD1a-autoreactive T cells expressed skin homing receptors and predominantly produced the cytokine IL-22, which is involved in skin homeostasis and inflammation (Duhen, T., et al. *Nat. Immunol.* 10, 857-863 (2009)). Additionally, IL-22-producing T cells ere stimulated by Langerhans cells (Fujita, H. et al. *Proc Natl. Acad. Sci. U.S.A* 106, 21795-21800 (2009)), which represent potent antigen-presenting cells (APCs) in human skin and, as a hallmark, abundantly express CD1a (Hunger, R. E. et al. *J. Clin. Invest* 113, 701-708 (2004), Pena-Cruz, V., et al. *J. Invest Dermatol.* 121, 517-521 (2003)).

Inflammatory Skin Disease

The skin is a large and vital organ that functions as mechanical, biochemical, and immunological barrier to protect the organism from damage (Perera, G. K., et al. *Annu. Rev. Pathol.* (2012)). Human skin consists of several layers including the outer epidermis and the dermis below that separates it from the subcutaneous tissue. The epidermis mainly consists of epithelial cells termed keratinocytes that give rise to the cornified layer on top. Langerhans cells, the epidermal APCs, are located in the basal layer close to the basement membrane (Fujita, H. et al. *Proc. Natl. Acad. Sci. U S. A* 106, 21795-21800 (2009)). The dermis consists of connective tissue containing blood vessels, dermal dendritic cells (DCs), and T cells. Human skin contains 1-2 million T lymphocytes per $cm^2$ in the steady-state, and thus, the skin is a large immunological organ (Clark, R. A. et al. *J. Immunol.* 176, 4431-4439 (2006)).

Various skin conditions are associated with increased T cell activation and abnormal antigen presentation in the dermis and epidermis (Cooper, *Curr. Probl. Dermatol.* eds. van Vloten et al., 19, pp. 69-80 at pp. 73, 74, 76 (1990)). For example, in contact allergic dermatitis, activation of intracutaneous T-cells is observed. It is known that skin from patients exhibiting atopic dermatitis contains an increased number of Langerhans cells (Cooper, supra). In psoriatic skin, there is an increased number of antigen presenting cells, composed of both Langerhans cells and non-Langerhans cell Class II MHC-bearing antigen presenting cells (Cooper, supra).

Dysregulation of skin homeostasis can lead to inflammation such as in psoriasis and atopic dermatitis (Perera, G. K., et al. *Annu. Rev. Pathol.* (2012)). Psoriasis is known as T cell-mediated chronic relapsing skin inflammation that represents an important public health problem with a prevalence of ~5% in the U.S. It macroscopically presents with classical skin lesions, including elevation, erythema, and scaling. Histologically, psoriatic skin is characterized by thickening of the epidermis (acanthosis), epidermal extensions into the dermis (papillomatosis), and a differentiation defect of keratinocytes leading to a nucleated cornified layer (parakeratosis) (Perera, G. K., et al. *Annu. Rev. Pathol.* (2012)). Cellular infiltrate in psoriatic skin consists of CD8 T cells in the epidermis and mainly CD4 T cells in the dermis. Seminal work by Nestle and colleagues demonstrated that pre-psoriatic (healthy) skin from psoriasis patients transplanted onto immunodeficient mice spontaneously developed psoriasis (Boyman, O. et al. *J. Exp. Med.* 199, 731-736 (2004)). In this context, skin-resident passenger T cells were responsible for generating inflammatory disease (Boyman, O. et al. *J. Exp. Med.* 199, 731-736 (2004)).

The methods and compositions described herein are useful to prevent or treat mammalian (e.g., human) skin conditions characterized by increased T cell activation and abnormal antigen presentation in the dermis and epidermis, by administering inhibitors of CD1a expression or activity. The methods and compositions described herein are contemplated for both therapeutic treatment of inflammatory skin disease and for prophylaxis of inflammatory skin disease. Essentially any inflammatory skin disease comprising CD1a-mediated inflammation can be treated using the methods and assays described herein.

As used herein, the term "inflammatory skin disease" refers to a skin condition accompanied by inflammation that is mediated, in part, by T-cells. Non-limiting examples of inflammatory skin diseases include psoriasis, psoriasis guttata, inverse psoriasis, pustular psoriasis, psoriatic erythroderma, acute febrile neutrophilic dermatosis, eczema, xerotic eczema, dyshidrotic eczema, vesicular palmar eczema, acne vulgaris, atopic dermatitis, contact dermatitis, allergic contact dermatitis, dermatomyositis, exfoliative dermatitis, hand eczema, pompholyx, rosacea, rosacea due to sarcoidosis, rosacea due to scleroderma, rosacea due to Sweet syndrome, rosacea due to systemic lupus erythematosus, rosacea due to urticaria, rosacea due to herpetic pain, Sweet's disease, neutrophilic hydrodenitis, sterile pustule, drug rash, seborrheic dermatitis, *pityriasis rosea*, Kikuchi's disease of the skin, pruritic urticarial papules and plaques of pregnancy, Stevens-Johnson syndrome and toxic epidermal necrolysis, tattoo reaction, Wells syndrome (eosinophilic cellulitis), reactive arthritis (Reiter syndrome), bowel-associated dermatosis-arthritis syndrome, rheumatoid neutrophilic dermatosis, neutrophilic eccrine hidradenitis, neutrophilic skin disease of dorsum of hand, balanitis circumscripta plasmacellularis, balanoposthitis, Behcet's disease, erythema annulare centrifugum, erythema dyschromicum perstans, erythema multiforme, granuloma annulare, dermatitis of hand, lichen *nitidus*, lichen planus, lichen sclerosus et atrophicus, lichen simplex chronicus, lichen spinulosus, nummular dermatitis, pyoderma gangrenosum, sarcoidosis, subkeratinous pustular dermatosis, urticaria, transient acantholytic dermatosis, urushiol-induced contact dermatitis, and the like.

In one embodiment, the inflammatory skin disease is urushiol-induced contact dermatitis, which can be caused by exposure to plants of the *Toxicodendron* family (e.g., poison oak, poison ivy, poison sumac), members of the Anacardiaceae family (e.g., (mango, Rengas tree, Burmese lacquer tree, India marking nut tree, and the shell of the cashew nut) or *Ginkgo biloba*.

In another embodiment, the inflammatory skin disease is psoriasis.

Urushiol-Induced Contact Dermatitis

Approximately 350,000 to 500,000 Americans suffer from rashes resulting from urushiol exposure every year. In particular, the genus *Toxicodendron* species (e.g., Western and Eastern poison oak *T. diversilobum*, poison ivy *T. radicans*, and poison sumac or dogwood *T. vernix*) are distributed widely across North America. Other sources of urushiol include poison wood (in Florida and the Bahamas), and the sap (kiurushi) of the Asian lacquer tree (*Toxicodendron verniciflua*) used as a varnish in Japanese lacquer ware, and cashew nut shells. (See, for example, Tucker and Swan (1998) NEJM, 339(4): 235.)

Reaction to urushiol is an immunological response to the bio-oxidized form of urushiol (the ortho-quinone). Approximately 50-70% of the U.S. population is either allergic to urushiol, or will become allergic to it upon sensitization by repeated exposure. Symptoms of allergic contact dermatitis from urushiol exposure (often referred to as Rhus dermatitis) vary from a mild annoyance to weeks of irritation and pain. Occasionally, exposure can lead to nephropathy and even to fatal systemic anaphylaxis.

The best treatment to date is to avoid contact with urushiol. There are many recommended methods to remove urushiol after recent contact, including water, soapy water, organic solvents, and a variety of commercially available solubilizing mixtures including TECHNU, IVYCLEANSE, ALL-STOP, ZANFEL (comprising fatty acid, alcohol, and the surfactant sodium lauroyl sarcosinate), and even DIAL ultra-dishwashing soap. Pharmacological treatment of the contact dermatitis usually involves a course of topical and/or enteric treatments with hydrocortisones, β-methasone, and other similar corticosteroids.

Psoriasis

Psoriasis is an inflammatory skin condition characterized by frequent episodes of redness, itching, and thick, dry, silvery scales on the skin. Psoriasis comprises lesions that can involve primary and secondary alterations in epidermal proliferation, inflammatory responses of the skin, and an expression of regulatory molecules such as lymphokines and inflammatory factors. Psoriatic skin is morphologically characterized by an increased turnover of epidermal cells, thickened epidermis, abnormal keratinization, inflammatory cell infiltrates into the epidermis and polymorphonuclear leukocyte and lymphocyte infiltration into the epidermis layer. Psoriasis can also involve fingernails or toenails, which frequently exhibit pitting, separation of the nail, thickening, and to discoloration. Psoriasis is often associated with other inflammatory disorders, for example arthritis, including rheumatoid arthritis, inflammatory bowel disease (IBD), and Crohn's disease.

Evidence of psoriasis is most commonly seen on the trunk, elbows, knees, scalp, skin folds, or fingernails, but it may affect any or all parts of the skin. Normally, it takes about a month for new skin cells to move up from the lower layers to the surface. In psoriasis, this process takes only a few days, resulting in a build-up of dead skin cells and formation of thick scales. Symptoms of psoriasis include: skin patches, that are dry or red, covered with silvery scales, raised patches of skin, accompanied by red borders, that can crack and become painful, and that are usually located on the elbows, knees, trunk, scalp, and hands; skin lesions, including pustules, cracking of the skin, and skin redness; joint pain or aching which can be associated with of arthritis, e.g., psoriatic arthritis.

A diagnosis of psoriasis is usually based on the appearance of the skin. Additionally, a skin biopsy, or scraping and culture of skin patches may be needed to rule out other skin disorders. An x-ray can be used to check for psoriatic arthritis if joint pain is present and persistent.

Severity of psoriasis can be determined according to standard clinical definitions. For example, the Psoriasis Area and Severity Index (PASI) is used by dermatologists to assess psoriasis disease intensity. This index is based on the quantitative assessment of three typical signs of psoriatic lesions: erythema, infiltration, and desquamation, combined with the skin surface area involvement. Since its development in 1978, this instrument has been used throughout the world by clinical investigators (Fredriksson T, Petersson U: Severe psoriasis—oral therapy with a new retinoid. Dermatologica 1978; 157: 238-41). PASI is indicated as PASI 50 (a 50 percent improvement in PASI from baseline), PASI 75 (a 75 percent improvement in PASI from baseline), PASI 90 (a 90 percent improvement in PASI from baseline), and PASI 100 (a 100 percent improvement in PASI from baseline).

The Physicians Global Assessment (PGA) is used to assess psoriasis activity and follow clinical response to treatment. It is a six-point score that summarizes the overall quality (erythema, scaling and thickness) and extent of plaques relative to the baseline assessment. A patient's response is rated as worse, poor (0-24%), fair (25-49%), good (50-74%), excellent (75-99%), or cleared (100%) (van der Kerkhof P. The psoriasis area and severity index and alternative approaches for the assessment of severity: persisting areas of confusion. Br J Dermatol 1997; 137:661-662).

Another measure of improvement in the disease state of a subject having psoriasis includes clinical responses, such as the Dermatology Life Quality Index (DLQI) or the Minimum Clinically Important Difference (MCID).

Atopic Dermatitis

Atopic Dermatitis (AD) is another chronic inflammatory skin disease with a prevalence of 5-20% in children and ~11% in the total population of the US. The cardinal symptoms include pruritus (itch) and xerosis (dry skin). In addition, patients show erythema and development of vesicles. In the chronic phase, epidermal thickening leads to lichenification mainly of flexural sites. The etiology of AD is unknown, and historically pathogenesis was explained by atopy (hence the name), which is characterized by IgE and Th2 cell-mediated allergic inflammation. However, most cases of AD are not associated with the atopic complex, including allergic rhinitis and asthma. Current opinion rather explains the generation of AD by an underlying defect in epidermal barrier function that leads to exposure to skin irritants inducing subsequent inflammation. In the acute phase, a predominant Th2 cell infiltrate influences inflammation. However, in the chronic phase of AD, Th1 cells as well as IL-17-producing cells are involved in the inflammatory response. Additionally, IL-22 facilitates keratinocyte proliferation and promotes epidermal thickening. Treatment of AD is largely symptomatic and is based on emollients against xerosis and corticosteroids to suppress inflammation. Biologics for therapy of AD are currently not available.

Alternative Indications

Mastocytosis: Mastocytosis is the uncontrolled amplification of mast cells. Mastocytosis is an orphan disease with fewer than 200,000 cases diagnosed each year in the United States. Mast cells are known to express c-kit and IgE receptors, and further contain inflammatory mediators such as histamine.

Mast cell degranulation causes allergic symptoms either locally (e.g., Urticaria pigmentosa) or systemically (e.g., affecting organs such as the gut). Mastocytosis is associated with skin lesions, allergic reactions, shock and enterocolitis, among others. The present treatment is symptomatic using medications such as antihistamines.

It has been shown that mast cells in mastocytosis express CD1a. Thus, it is also contemplated herein that mastocytosis can be treated using the methods and compositions described herein. Two CD1a-based therapeutic options are contemplated: (i) depletion of "neoplastic" mast cells using anti-CD1a antibody (normal mast cells are CD1a-negative and remain "untouched"), and (ii) blocking of CD1a-mediated T cell responses that provide growth signals for mast cells, using a small molecule inhibitor of CD1a.

Histiocytosis: Langerhans cell histiocytosis (LCH) is defined as the abnormal expansion of Langerhans cells, and has an incidence of approximately 1 in 200,000. There are three known clinical forms including (i) unifocal (Eosinophilic granuloma), (ii) multifocal (Hand-Schueller-Christian), and (iii) multisystem (Abt-Letterer-Siwe). Histiocytosis primarily affects the bone causing painful bone swelling and fractures, however it is also associated with skin lesions, lung inflammation, and endocrine disorders (e.g., diabetes insipidus). Current treatment for histiocytosis includes corticosteroids and chemotherapy.

Contemplated herein is the treatment of histiocytosis using the CD1a-based therapies described herein including, but not limited to, (i) depletion of neoplastic Langerhans cells using an anti-CD1a antibody, and (ii) small molecule inhibitor targeting CD1a to block CD1a-restricted inflammation.

Sarcoidosis: Sarcoidosis is a chronic inflammatory disease mainly affecting the lung. It has an incidence of 10-20 in 100,000 in the United States. Sarcoidosis comprises inflammation characterized by granuloma formation. The signs and symptoms of sarcoidosis include, but are not limited to, lung granuloma, lymphadenopathy, and skin lesions (e.g., erythema nodosum). Current therapies include corticosteroids and chemotherapy.

Sarcoidosis is known to be associated with psoriasis, and can develop as a secondary disease. Thus, the methods and compositions described herein are also contemplated for use in the treatment of sarcoidosis.

Antibodies

In one embodiment, a therapeutic antibody that binds to e.g., CD1a is used herein in the prophylaxis or treatment of an inflammatory skin disease.

An "antibody" that can be used according to the methods described herein includes complete immunoglobulins, antigen binding fragments of immunoglobulins, as well as antigen binding proteins that comprise antigen binding domains of immunoglobulins. Antigen binding fragments of immunoglobulins include, for example, Fab, Fab', F(ab')2, scFv and dAbs. Modified antibody formats have been developed which retain binding specificity, but have other characteristics that may be desirable, including for example, bispecificity, multivalence (more than two binding sites), and compact size (e.g., binding domains alone). Single chain antibodies lack some or all of the constant domains of the whole antibodies from which they are derived. Therefore, they can overcome some of the problems associated with the use of whole antibodies. For example, single-chain antibodies tend to be free of certain undesired interactions between heavy-chain constant regions and other biological molecules. Additionally, single-chain antibodies are considerably smaller than whole antibodies and can have greater permeability than whole antibodies, allowing single-chain antibodies to localize and bind to target antigen-binding sites more efficiently. Furthermore, the relatively small size of single-chain antibodies makes them less likely to provoke an unwanted immune response in a recipient than whole antibodies. Multiple single chain antibodies, each single chain having one VH and one VL domain covalently linked by a first peptide linker, can be covalently linked by at least one or more peptide linker to form multivalent single chain antibodies, which can be monospecific or multispecific. Each chain of a multivalent single chain antibody includes a variable light chain fragment and a variable heavy chain fragment, and is linked by a peptide linker to at least one other chain. The peptide linker is composed of at least fifteen amino acid residues. The maximum number of linker amino acid residues is approximately one hundred. Two single chain antibodies can be combined to form a diabody, also known as a bivalent dimer. Diabodies have two chains and two binding sites, and can be monospecific or bispecific. Each chain of the diabody includes a VH domain connected to a VL domain. The domains are connected with linkers that are short enough to prevent pairing between domains on the same chain, thus driving the pairing between complementary domains on different chains to recreate the two antigen-binding sites. Three single chain antibodies can be combined to form triabodies, also known as trivalent trimers. Triabodies are constructed with the amino acid terminus of a VL or VH domain directly fused to the carboxyl terminus of a VL or VH domain, i.e., without any linker sequence. The triabody has three Fv heads with the polypeptides arranged in a cyclic, head-to-tail fashion. A possible conformation of the triabody is planar with the three binding sites located in a plane at an angle of 120 degrees from one another. Triabodies can be monospecific, bispecific or trispecific. Thus, antibodies useful in the methods described herein include, but are not limited to, naturally occurring antibodies, bivalent fragments such as (Fab')2, monovalent fragments such as Fab, single chain antibodies, single chain Fv (scFv), single domain antibodies, multivalent single chain antibodies, diabodies, triabodies, and the like that bind specifically with an antigen.

Antibodies can also be raised against a polypeptide or portion of a polypeptide by methods known to those skilled in the art. Antibodies are readily raised in animals such as rabbits or mice by immunization with the gene product, or a fragment thereof. Immunized mice are particularly useful for providing sources of B cells for the manufacture of hybridomas, which in turn are cultured to produce large quantities of monoclonal antibodies. Antibody manufacture methods are described in detail, for example, in Harlow et al., 1988. While both polyclonal and monoclonal antibodies can be used in the methods described herein, it is preferred that a monoclonal antibody is used where conditions require increased specificity for a particular protein.

Useful monoclonal antibodies and fragments can be derived from any species (including humans) or can be formed as chimeric proteins which employ sequences from more than one species. Human monoclonal antibodies or "humanized" murine antibodies are also used in accordance with the methods and assays described herein. For example, a murine monoclonal antibody can be "humanized" by genetically recombining the nucleotide sequence encoding the murine Fv region (i.e., containing the antigen binding sites) or the complementarity determining regions thereof with the nucleotide sequence encoding a human constant domain region and an Fc region. Humanized targeting moieties are recognized to decrease the immunoreactivity of the antibody or polypeptide in the host recipient, permitting an increase in the half-life and a reduction of the possibly of adverse immune reactions. The murine monoclonal antibodies should preferably be employed in humanized form. Antigen binding activity is determined by the sequences and conformation of the amino acids of the six complementarity determining regions (CDRs) that are located (three each) on the light and heavy chains of the variable portion (Fv) of the antibody. The 25-kDa single-chain Fv (scFv) molecule is composed of a variable region (VL) of the light chain and a variable region (VH) of the heavy chain joined via a short peptide spacer sequence. Techniques have been developed to display scFv molecules on the surface of filamentous phage that contain the gene for the scFv. scFv molecules with a broad range of antigenic-specificities can be present in a single large pool of scFv-phage library.

Chimeric antibodies are immunoglobin molecules characterized by two or more segments or portions derived from different animal species. Generally, the variable region of the chimeric antibody is derived from a non-human mammalian antibody, such as a murine monoclonal antibody, and the immunoglobulin constant region is derived from a human immunoglobulin molecule. In some embodiments, both regions and the combination have low immunogenicity as routinely determined.

In one embodiment, the inhibitor of CD1a is a human binding molecule against CD1a as described in U.S. Pat. No. 7,968,092, the contents are incorporated here in reference in its entirety.

In one embodiment, the inhibitor of CD1a is a monoclonal antibody that binds to human CD1a as described in U.S. Pat. No. 7,968,092, wherein the monoclonal antibody comprises a heavy chain variable region and a light chain variable region.

In one embodiment, the inhibitor of CD1a is a monoclonal antibody that binds to human CD1a as described in U.S. Pat. No. 7,968,092 is an IgG1.

In one embodiment, the inhibitor of CD1a is a monoclonal antibody that binds to human CD1a as described in U.S. Pat. No. 7,968,092 has cytotoxic activity against a CD1a-expressing cell.

Nucleic Acid Inhibitors of CD1a Expression

A powerful approach for inhibiting the expression of selected target polypeptides is through the use of RNA interference agents. RNA interference (RNAi) uses small interfering RNA (siRNA) duplexes that target the messenger RNA encoding the target polypeptide for selective degradation. siRNA-dependent post-transcriptional silencing of gene expression involves cleaving the target messenger RNA molecule at a site guided by the siRNA. "RNA interference (RNAi)" is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) J. of Virology 76(18): 9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex (termed "RNA induced silencing complex," or "RISC") that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" includes any decrease in expression or protein activity or level of the target gene or protein encoded by the target gene as compared to a situation wherein no RNA interference has been induced. The decrease will be of at least 10%, 20%, 30%, 40%, 50%, 60%, 70%, 80%, 90%, 95% or 99% or more as compared to the expression of a target gene or the activity or level of the protein encoded by a target gene which has not been targeted by an RNA interfering agent.

The terms "RNA interference agent" and "RNA interference" as they are used herein are intended to encompass those forms of gene silencing mediated by double-stranded RNA, regardless of whether the RNA interfering agent comprises an siRNA, miRNA, shRNA or other double-stranded RNA molecule. "Short interfering RNA" (siRNA), also referred to herein as "small interfering RNA" is defined as an RNA agent which functions to inhibit expression of a target gene, e.g., by RNAi. An siRNA can be chemically synthesized, can be produced by in vitro transcription, or can be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and can contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand can precede the nucleotide loop structure and the antisense strand can follow. These shRNAs can be contained in plasmids, retroviruses, and lentiviruses and expressed from, for example, the pol III U6 promoter, or another promoter (see, e.g., Stewart, et al. (2003) RNA April; 9(4):493-501, incorporated by reference herein in its entirety). The target gene or sequence of the RNA interfering agent can be a cellular gene or genomic sequence, e.g. the CD1a sequence. An siRNA can be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence include RNA derivatives and analogs. Preferably, the siRNA is identical to its target. The siRNA preferably targets only one sequence. Each of the RNA interfering agents, such as siRNAs, can be screened for potential off-target effects by, for example, expression profiling. Such methods are known to one skilled in the art and are described, for example, in Jackson et al. Nature Biotechnology 6:635-637, 2003. In addition to expression profiling, one can also screen the potential target sequences for similar sequences in the sequence databases to identify potential sequences which can have off-target effects. For example, according to Jackson et al. (Id.), 15, or perhaps as few as 11 contiguous nucleotides, of sequence identity are sufficient to direct silencing of non-targeted transcripts. Therefore, one can initially screen the proposed siRNAs to avoid potential off-target silencing using the sequence identity analysis by any known sequence comparison methods, such as BLAST. siRNA sequences are chosen to maximize the uptake of the antisense (guide) strand of the siRNA into RISC and thereby maximize the ability of RISC to target human GGT mRNA for degradation. This can be accomplished by scanning for sequences that have the lowest free energy of binding at the 5'-terminus of the antisense strand. The lower free energy leads to an enhancement of the unwinding of the 5'-end of the antisense strand of the siRNA duplex, thereby ensuring that the antisense strand will be taken up by RISC and direct the sequence-specific cleavage of the mRNA. siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues can be used, such as a phosphorothioate linkage. The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatizes with a variety of groups. Other useful RNA derivatives incorporate nucleotides having modified carbohydrate moieties, such as 2'O-alkylated residues or 2'-O-methyl ribosyl derivatives and 2'-O-fluoro ribosyl derivatives. The RNA bases can also be modified. Any modified base useful for inhibiting or interfering with the expression of a target sequence can be used. For example, halogenated bases, such as 5-bromouracil and 5-iodouracil can be incorporated. The bases can also be alkylated, for example, 7-methylguanosine can be incorporated in place of a guanosine residue. Non-natural bases that yield successful inhibition can also be incorporated. The most preferred siRNA modifications include 2'-deoxy-2'-fluorouridine or locked nucleic acid (LAN) nucleotides and RNA duplexes containing either phosphodiester or varying numbers of phosphorothioate linkages. Such modifications are known to one skilled in the art and are described, for example, in Braasch et al., Biochemistry, 42: 7967-7975, 2003. Most of the useful modifications to the siRNA molecules can be introduced using chemistries established for antisense oligonucleotide technology. Preferably, the modifications involve minimal 2'-O-methyl modification, preferably excluding such modification. Modifications also preferably exclude modifications of the free 5'-hydroxyl groups of the siRNA.

In a preferred embodiment, the RNA interference agent is delivered or administered in a pharmaceutically acceptable carrier. Additional carrier agents, such as liposomes, can be added to the pharmaceutically acceptable carrier. In another embodiment, the RNA interference agent is delivered by a vector encoding small hairpin RNA (shRNA) in a pharmaceutically acceptable carrier to the cells in an organ of an individual. The shRNA is converted by the cells after transcription into siRNA capable of targeting, for example, CD1a.

In one embodiment, the vector is a regulatable vector, such as a tetracycline inducible vector. Methods described, for example, in Wang et al. Proc. Natl. Acad. Sci. 100: 5103-5106, using pTet-On vectors (BD Biosciences Clontech, Palo Alto, Calif.) can be used. In one embodiment, the RNA interference agents used in the methods described herein are taken up actively by cells in vivo following intravenous injection, e.g., hydrodynamic injection, without the use of a vector, illustrating efficient in vivo delivery of the RNA interfering agents. One method to deliver the siRNAs is by topical administration in an appropriate pharmaceutically acceptable carrier. Other strategies for delivery of the RNA interference agents, e.g., the siRNAs or shRNAs used in the methods of the invention, can also be employed, such as, for example, delivery by a vector, e.g., a plasmid or viral vector, e.g., a lentiviral vector. Such vectors can be used as described, for example, in Xiao-Feng Qin et al. Proc. Natl. Acad. Sci. U.S.A., 100: 183-188. Other delivery methods include delivery of the RNA interfering agents, e.g., the siRNAs or shRNAs of the invention, using a basic peptide by conjugating or mixing the RNA interfering agent with a basic peptide, e.g., a fragment of a TAT peptide, mixing with cationic lipids or formulating into particles. The RNA interference agents, e.g., the siRNAs targeting CD1a mRNA, can be delivered singly, or in combination with other RNA interference agents, e.g., siRNAs, such as, for example siRNAs directed to other cellular genes. siRNAs can also be administered in combination with other pharmaceutical agents which are used to treat or prevent diseases or disorders comprising inflammation of the skin. Synthetic siRNA molecules, including shRNA molecules, can be obtained using a number of techniques known to those of skill in the art. For example, the siRNA molecule can be chemically synthesized or recombinantly produced using methods known in the art, such as using appropriately protected ribonucleoside phosphoramidites and a conventional DNA/RNA synthesizer (see, e.g., Elbashir, S. M. et al. (2001) Nature 411:494-498; Elbashir, S. M., W. Lendeckel and T. Tuschl (2001) Genes & Development 15:188-200; Harborth, J. et al. (2001) J. Cell Science 114:4557-4565; Masters, J. R. et al. (2001) Proc. Natl. Acad. Sci., USA 98:8012-8017; and Tuschl, T. et al. (1999) Genes & Development 13:3191-3197). Alternatively, several commercial RNA synthesis suppliers are available including, but not limited to, Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). As such, siRNA molecules are not overly difficult to synthesize and are readily provided in a quality suitable for RNAi. In addition, dsRNAs can be expressed as stem loop structures encoded by plasmid vectors, retroviruses and lentiviruses (Paddison, P. J. et al. (2002) Genes Dev. 16:948-958; McManus, M. T. et al. (2002) RNA 8:842-850; Paul, C. P. et al. (2002) Nat. Biotechnol. 20:505-508; Miyagishi, M. et al. (2002) Nat. Biotechnol. 20:497-500; Sui, G. et al. (2002) Proc. Natl. Acad. Sci., USA 99:5515-5520; Brummelkamp, T. et al. (2002) Cancer Cell 2:243; Lee, N. S., et al. (2002) Nat. Biotechnol. 20:500-505; Yu, J. Y., et al. (2002) Proc. Natl. Acad. Sci., USA 99:6047-6052; Zeng, Y., et al. (2002) Mol. Cell 9:1327-1333; Rubinson, D. A., et al. (2003) Nat. Genet. 33:401-406; Stewart, S. A., et al. (2003) RNA 9:493-501). These vectors generally have a polIII promoter upstream of the dsRNA and can express sense and antisense RNA strands separately and/or as a hairpin structure. Within cells, Dicer processes the short hairpin RNA (shRNA) into effective siRNA. The targeted region of the siRNA molecule of the present invention can be selected from a given target gene sequence, e.g., a CD1a coding sequence, beginning from about 25 to 50 nucleotides, from about 50 to 75 nucleotides, or from about 75 to 100 nucleotides downstream of the start codon. Nucleotide sequences can contain 5' or 3' UTRs and regions nearby the start codon. One method of designing a siRNA molecule of the present invention involves identifying the 23 nucleotide sequence motif AA(N19)TT (where N can be any nucleotide) and selecting hits with at least 25%, 30%, 35%, 40%, 45%, 50%, 55%, 60%, 65%, 70% or 75% G/C content. The "TT" portion of the sequence is optional. Alternatively, if no such sequence is found, the search can be extended using the motif NA(N21), where N can be any nucleotide. In this situation, the 3' end of the sense siRNA can be converted to TT to allow for the generation of a symmetric duplex with respect to the sequence composition of the sense and antisense 3' overhangs. The antisense siRNA molecule can then be synthesized as the complement to nucleotide positions 1 to 21 of the 23 nucleotide sequence motif. The use of symmetric 3' TT overhangs can be advantageous to ensure that the small interfering ribonucleoprotein particles (siRNPs) are formed with approximately equal ratios of sense and antisense target RNA-cleaving siRNPs (Elbashir et al., (2001) supra and Elbashir et al., 2001 supra). Analysis of sequence databases, including but not limited to the NCBI, BLAST, Derwent and GenSeq as well as commercially available oligosynthesis companies such as Oligoengine®, can also be used to select siRNA sequences against EST libraries to ensure that only one gene is targeted.

siRNA sequences to target CD1a can also be obtained commercially from e.g., INVITROGEN™, THERMO SCIENTIFIC™, ORIGENE™, among others.

Delivery of RNA Interfering Agents

Methods of delivering RNA interference agents, e.g., an siRNA, or vectors containing an RNA interference agent, to the target cells, e.g., Langerhans cells, skin cells, or other desired target cells, for uptake include topical administration or injection of a composition containing the RNA interference agent, e.g., an siRNA, or directly contacting the cell, e.g., a Langerhans cell, with a composition comprising an RNA interference agent, e.g., an siRNA. In another embodiment, RNA interference agent, e.g., an siRNA can be injected directly into any blood vessel, such as vein, artery, venule or arteriole, via, e.g., hydrodynamic injection or catheterization. Administration can be by a single injection or by two or more injections. The RNA interference agent is delivered in a pharmaceutically acceptable carrier. One or more RNA interference agents can be used simultaneously. In one embodiment, a single siRNA that targets human CD1a is used. In one embodiment, specific cells are targeted with RNA interference, limiting potential side effects of RNA interference caused by non-specific targeting of RNA interference. The method can use, for example, a complex or a fusion molecule comprising a cell targeting moiety and an RNA interference binding moiety that is used to deliver RNA interference effectively into cells. For example, an antibody-protamine fusion protein when mixed with siRNA, binds siRNA and selectively delivers the siRNA into cells expressing an antigen recognized by the antibody, resulting in silencing of gene expression only in those cells that express the antigen. The siRNA or RNA interference-inducing molecule binding moiety is a protein or a nucleic acid binding domain or fragment of a protein, and the binding moiety is fused to a portion of the targeting moiety. The location of the targeting moiety can be either in the carboxyl-terminal or amino-terminal end of the construct or in the middle of the fusion protein. A viral-mediated delivery mechanism can also be employed to deliver siRNAs to cells in vitro and in vivo as described in Xia, H. et al. (2002) Nat Biotechnol 20(10):1006). Plasmid- or viral-mediated delivery mechanisms of shRNA can also be employed to deliver shRNAs to cells in vitro and in vivo as described in Rubinson, D. A., et al. ((2003) Nat. Genet. 33:401-406) and Stewart, S. A., et al. ((2003) RNA 9:493-501). The RNA interference agents, e.g., the siRNAs or shRNAs, can be introduced along with components that perform one or more of the following activities: enhance uptake of the RNA interfering agents, e.g., siRNA, by the cell, e.g., lymphocytes or other cells, inhibit annealing of single strands, stabilize single strands, or otherwise facilitate delivery to the target cell and increase inhibition of the target gene, e.g., CD1a. The dose of the particular RNA interfering agent will be in an amount necessary to effect RNA interference, e.g., post translational gene silencing (PTGS), of the particular target gene, thereby leading to inhibition of target gene expression or inhibition of activity or level of the protein encoded by the target gene.

Small Molecule Inhibition of CD1a Activity or Expression

As used herein, the term "small molecule" refers to a chemical agent including, but not limited to, peptides, peptidomimetics, amino acids, amino acid analogs, polynucleotides, polynucleotide analogs, aptamers, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Essentially any small molecule inhibitor of CD1a expression and/or activity can be used in the treatment of an inflammatory skin disease using the methods described herein. Screening assays are provided herein for identifying candidate small molecule agents that inhibit CD1a expression and/or activity.

Dosage and Administration

In one aspect, the methods described herein provide a method for treating an inflammatory skin disease (e.g., urushiol-induced contact dermatitis, psoriasis, among others) in a subject. In one embodiment, the subject can be a mammal. In another embodiment, the mammal can be a human, although the approach is effective with respect to all mammals. The method comprises administering to the subject an effective amount of a pharmaceutical composition comprising an inhibitor that binds CD1a, in a pharmaceutically acceptable carrier. In some embodiments, the inhibitor of CD1a comprises a binding protein, such as an antibody or a peptide. In other embodiments, the inhibitor of CD1a comprises a small molecule or an RNA interference molecule (e.g., siRNA, shRNA etc).

The dosage range for the agent depends upon the potency, and includes amounts large enough to produce the desired effect, e.g., immune response modulation. The dosage should not be so large as to cause unacceptable adverse side effects. Generally, the dosage will vary with the type of inhibitor (e.g., an antibody or fragment, small molecule, siRNA, etc.), and with the age, condition, and sex of the patient. The dosage can be determined by one of skill in the art and can also be adjusted by the individual physician in the event of any complication. Typically, the dosage ranges from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 □g/kg body weight to 30 □g/kg body weight. Alternatively, the dose range will be titrated to maintain serum levels between 5 □g/mL and 30 □g/mL.

Administration of the doses recited above can be repeated for a limited period of time. In some embodiments, the doses are given once a day, or multiple times a day, for example but not limited to three times a day. In a preferred embodiment, the doses recited above are administered daily for several weeks or months. The duration of treatment depends upon the subject's clinical progress and responsiveness to therapy. Continuous, relatively low maintenance doses are contemplated after an initial higher therapeutic dose.

A therapeutically effective amount is an amount of an agent that is sufficient to produce a statistically significant, measurable change in immune response (see "Efficacy Measurement" below). Such effective amounts can be gauged in clinical trials as well as animal studies for a given agent.

Agents useful in the methods and compositions described herein can be administered topically, intravenously (by bolus or continuous infusion), orally, by inhalation, intraperitoneally, intramuscularly, subcutaneously, intracavity, and can be delivered by peristaltic means, if desired, or by other means known by those skilled in the art. In one embodiment it is preferred that the agents for the methods described herein are administered directly to a lesion (e.g., during surgery or by direct injection). The agent can be administered systemically, if so desired.

Therapeutic compositions containing at least one agent can be conventionally administered in a unit dose. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. An agent can be targeted by means of a targeting moiety, such as e.g., an antibody or targeted liposome technology. In some embodiments, an agent can be targeted to a tissue by using bispecific antibodies, for example produced by chemical linkage of an anti-ligand antibody (Ab) and an Ab directed toward a specific target. To avoid the limitations of chemical conjugates, molecular conjugates of antibodies can be used for production of recombinant bispecific single-chain Abs directing ligands and/or chimeric inhibitors at cell surface molecules. The addition of an antibody to an agent permits the agent to accumulate additively at the desired target site (e.g., lesion). Antibody-based or non-antibody-based targeting moieties can be employed to deliver a ligand or the inhibitor to a target site. Preferably, a natural binding agent for an unregulated or disease associated antigen is used for this purpose.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more intervals by a subsequent injection or other administration. Alternatively, continuous intravenous infusion sufficient to maintain concentrations in the blood in the ranges specified for in vivo therapies are contemplated.

Pharmaceutical Compositions

The present invention includes, but is not limited to, therapeutic compositions useful for practicing the therapeutic methods described herein. Therapeutic compositions contain a physiologically tolerable carrier together with an active agent as described herein, dissolved or dispersed therein as an active ingredient. In a preferred embodiment, the therapeutic composition is not immunogenic when administered to a mammal or human patient for therapeutic purposes. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically, such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the methods described herein that will be effective in the treatment of a particular disorder or condition will depend on the nature of the disorder or condition, and can be determined by standard clinical techniques.

In one embodiment, the composition comprises an inhibitor of CD1a that is a human binding molecule against CD1a as described in U.S. Pat. No. 7,968,092.

In one embodiment, the composition comprises an inhibitor of CD1a that is a monoclonal antibody that binds to human CD1a as described in U.S. Pat. No. 7,968,092, wherein the monoclonal antibody comprises a heavy chain variable region and a light chain variable region.

In one embodiment, the composition comprises an inhibitor of CD1a that is an IgG1 monoclonal antibody that binds to human CD1a as described in U.S. Pat. No. 7,968,092.

In one embodiment, the composition comprises an inhibitor of CD1a that is a monoclonal antibody that binds to human CD1a that has cytotoxic activity against a CD1a-expressing cell as described in U.S. Pat. No. 7,968,092.

Efficacy Measurement

The efficacy of a given treatment for an inflammatory skin disease (e.g., urushiol-induced contact dermatitis, psoriasis, among others) can be determined by the skilled clinician. However, a treatment is considered "effective treatment," as the term is used herein, if any one or all of the signs or symptoms of the immune disease is/are altered in a beneficial manner, other clinically accepted symptoms or markers of disease are improved, or even ameliorated, e.g., by at least 10% following treatment with an agent that comprises an inhibitor that binds CD1a or interferes with CD1a antigen-presenting activity. Efficacy can also be measured by failure of an individual to worsen as assessed by stabilization of the immune disease, hospitalization or need for medical interventions (i.e., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing progression of the immune disease; or (2) relieving the disease, e.g., causing regression of symptoms; and (3) preventing or reducing the likelihood of the development of the inflammatory skin disease, or preventing secondary diseases/disorders associated with the inflammatory disease (e.g., scarring, secondary bacterial infections such as *Staphylococcus aureus*, etc).

An effective amount for the treatment of a disease means that amount which, when administered to a mammal in need thereof, is sufficient to result in effective treatment as that term is defined herein, for that disease. Efficacy of an agent can be determined by assessing physical indicators of the inflammatory skin disease, such as e.g., redness, pain, inflammation, size of lesions, degree of oozing or pus formation, itchiness, etc.

Screening Assays

Screening assays as contemplated herein can be used to identify modulators, i.e., candidate or test compounds or agents (e.g., peptides, antibodies, peptidomimetics, small molecules (organic or inorganic) or other drugs) which modulate CD1a expression and/or activity. These assays are designed to identify compounds, for example, that interfere with the interaction of CD1a with a ligand such as urushiol or that prevent T-cell activation by CD1a.

The term "candidate agent" is used herein to mean any agent that is being examined for ability to modulate the interaction of CD1a with a ligand. Although the method generally is used as a screening assay to identify previously unknown molecules that can act as a therapeutic agent, the screening described herein can also be used to confirm that an agent known to have such activity, in fact has the activity, for example, in standardizing the activity of the therapeutic agent. A candidate agent can be any type of molecule, including, for example, a peptide, a peptidomimetic, a polynucleotide, or a small organic molecule, that one wishes to examine for the ability to modulate a desired activity, such as, for example, reducing CD1a expression and/or activity. It will be recognized that the methods described herein are readily adaptable to a high throughput format and, therefore, the methods are convenient for screening a plurality of test agents either serially or in parallel. The plurality of test agents can be, for example, a library of test agents produced by a combinatorial method library of test agents. Methods for preparing a combinatorial library of molecules that can be tested for therapeutic activity are well known in the art and include, for example, methods of making a phage display library of peptides, which can be constrained peptides (see, for example, U.S. Pat. Nos. 5,622,699; 5,206,347; Scott and Smith, Science 249:386-390, 1992; Markland et al., Gene 109:1319, 1991; each of which is incorporated herein by reference in their entireties); a peptide library (U.S. Pat. No. 5,264,563, which is incorporated herein by reference); a peptidomimetic library (Blondelle et al., Trends Anal. Chem. 14:8392, 1995; a nucleic acid library (O'Connell et al., supra, 1996; Tuerk and Gold, supra, 1990; Gold et al., supra, 1995; each of which is incorporated herein by reference in their entireties); an oligosaccharide library (York et al., Carb. Res., 285:99128, 1996; Liang et al., Science, 274:1520-1522, 1996; Ding et al., Adv. Expt. Med. Biol., 376:261-269, 1995; each of which is incorporated herein by reference in their entireties); a lipoprotein library (de Kruif et al., FEBS Lett., 399:232-236, 1996, which is incorporated herein by reference in their entireties); a glycoprotein or glycolipid library (Karaoglu et al., J. Cell Biol., 130:567-577, 1995, which is incorporated herein by reference); or a chemical library containing, for example, drugs or other pharmaceutical agents (Gordon et al., J. Med. Chem., 37:1385-1401, 1994; Ecker and Crooke, Bio/Technology, 13:351-360, 1995; each of which is incorporated herein by reference in their entireties).

Accordingly, the term "agent" as used herein means any compound or substance such as, but not limited to, a small molecule, nucleic acid, polypeptide, peptide, drug, ion, etc. An "agent" can be any chemical, entity or moiety, including without limitation synthetic and naturally-occurring proteinaceous and non-proteinaceous entities. In some embodiments, an agent is nucleic acid, nucleic acid analogues, proteins, antibodies, peptides, aptamers, oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof etc. In some embodiments, the nucleic acid is DNA or RNA, and nucleic acid analogues, for example can be PNA, pcPNA and LNA. A nucleic acid may be single or double stranded, and can be selected from a group comprising; nucleic acid encoding a protein of interest, oligonucleotides, PNA, etc. Such nucleic acid sequences include, for example, but not limited to, nucleic acid sequence encoding proteins that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide agent or fragment thereof, can be any protein of interest, for example, but not limited to; mutated proteins; therapeutic proteins; truncated proteins, wherein the protein is normally absent or expressed at lower levels in the cell. Proteins of interest can be selected from a group comprising; mutated proteins, genetically engineered proteins, peptides, synthetic peptides, recombinant proteins, chimeric proteins, antibodies, humanized proteins, humanized antibodies, chimeric antibodies, modified proteins and fragments thereof.

A candidate agent also includes any chemical, entity or moiety, including without limitation synthetic and naturally-occurring non-proteinaceous entities. In certain embodiments, the candidate agent is a small molecule having a chemical moiety. Such chemical moieties can include, for example, unsubstituted or substituted alkyl, aromatic, or heterocyclyl moieties and typically include at least an amine, carbonyl, hydroxyl or carboxyl group, frequently at least two of the functional chemical groups, including macrolides, leptomycins and related natural products or analogues thereof. Candidate agents can be known to have a desired activity and/or property, or can be selected from a library of diverse compounds. Also included as candidate agents are pharmacologically active drugs, genetically active molecules, etc. Such candidate agents of interest include, for example, chemotherapeutic agents, hormones or hormone antagonists, growth factors or recombinant growth factors and fragments and variants thereof. Exemplary of pharmaceutical agents suitable for use with the screening methods described herein are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all of which are incorporated herein by reference in their entireties. Also included are toxins, and biological and chemical warfare agents, for example see Somani, S. M. (Ed.), "Chemical Warfare Agents," Academic Press, New York, 1992), the contents of which is herein incorporated in its entirety by reference. Candidate agents, such as chemical compounds, can be obtained from a wide variety of sources including libraries of synthetic or natural compounds, such as small molecule compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Synthetic chemistry transformations and protecting group methodologies (protection and deprotection) useful in synthesizing the candidate compounds for use in the screening methods described herein are known in the art and include, for example, those such as described in R. Larock (1989) Comprehensive Organic Transformations, VCH Publishers; T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof, the contents of each of which are herein incorporated in their entireties by reference. Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carell et al (1994) Angew. Chem. Int. Ed. Engl. 33:2061; and Gallop et al. (1994) J. Med. Chem. 37:1233, the contents of each of which are herein incorporated in their entireties by reference. Libraries of candidate agents can also, in some embodiments, be presented in solution (e.g. Houghten (1992), Biotechniques 13:412-421), or on beads (Lam (1991), Nature 354:82-84), chips (Fodor (1993) Nature 364:555-556), bacteria (Ladner, U.S. Pat. No. 5,223,409), spores (Ladner U.S. Pat. No. 5,223,409), plasmids (Cull et al. (1992) Proc Natl Acad Sci USA 89:1865-1869) or on phage (Scott and Smith (1990) Science 249: 386-390; Devlin (1990) Science 249:404-406; Cwirla et al. (1990) Proc. Natl. Acad. Sci. 87:6378-6382; Felici (1991) J. Mol. Biol. 222:301-310; Ladner supra.), the contents of each of which are herein incorporated in their entireties by reference. The test compounds or candidate agents can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:145). Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233. Libraries of compounds can be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull et al. (1992) Proc Natl Acad Sci USA 89:1865-1869) or on phage (Scott and Smith (1990) Science 249:386-390); (Devlin (1990) Science 249: 404-406); (Cwirla et al. (1990) Proc. Natl. Acad. Sci. 87:6378-6382); (Felici (1991) J. Mol. Biol. 222:301-310); (Ladner supra.). The methods described herein further pertain to novel agents identified by the above-described screening assays. With regard to intervention, any treatments which modulate CD1a expression and/or activity should be considered as candidates for human therapeutic intervention.

In one embodiment, an assay is a cell-based assay comprising contacting a skin cell (e.g., Langerhans cell(s)) in culture with a candidate agent and determining the ability of the candidate agent to modulate (e.g., induce or inhibit) antigen presenting activity, CD1a ligand binding activity or T-cell activation.

In one embodiment, the screening assay is an in vitro assay designed to measure the degree of molecular interaction between CD1a and lipid ligands. Recombinant CD1a molecules are coupled to a detectable moiety and incubated with a known lipid ligand (e.g., sulfatide) in the presence or absence of one or more candidate agents. The detectable moiety permits one to measure whether a candidate agent is able to inhibit the interaction between CD1a and its ligand. As used herein, the term "reporter moiety" or "detectable moiety" refers to a molecule, or moiety of a molecule, capable of producing a detectable signal such as e.g., fluorescence, chemiluminescence, a colorimetric signal etc.

Alternatively, in another embodiment, the screening assay uses a label-free technology such as "bio-layer interferometry," which is an optical analytical technique that analyzes the interference pattern of white light reflected from two surfaces: a layer of immobilized protein on the biosensor tip, and an internal reference layer. Any change in the number of molecules bound to the biosensor tip causes a shift in the interference pattern that can be measured in real-time. The binding between a ligand immobilized on the biosensor tip surface and an analyte in solution produces an increase in optical thickness at the biosensor tip, which results in a wavelength shift, $\Delta\lambda$, which is a direct measure of the change in thickness of the biological layer. Interactions are measured in real time, providing the ability to monitor binding specificity, rates of association and dissociation, or concentration, with precision and accuracy. Bio-layer interferometric systems are available commercially from e.g., FORTEBIO. The OCTET system from FORTEBIO permits one to measure sensitive and specific binding curves that reflect the molecular interaction between recombinant CD1a and a lipid ligand (e.g., sulfatide), in the presence or absence of one or more (e.g., a plurality) of candidate agents.

In another embodiment, the screening assay uses a label-free technology such as "surface plasmon resonance." Surface plasmon resonance," as used herein, refers to the physical phenomenon in which incident light is converted strongly into electron currents at the metal surface for planar surfaces, and the term "localized surface plasmon resonance (LSPR)" can also be used for surface plasmon resonance of nanometer-sized structures. The oscillating currents produce strong electric fields in the (non-conducting) ambient medium near the surface of the metal. The electric fields, in turn, induce electric polarization in the ambient medium. Electric polarization is well known to cause the emission of light at wavelengths characteristic of the medium, i.e., the "Raman wavelengths." Additional background information regarding this phenomenon may be found in Surface Enhanced Raman Scattering, ed. Chang & Furtak, Plenum Press, NY (1982), the entire disclosure of which is incorporated herein by reference. As used herein, the term "Raman scattering" is intended to encompass all related physical phenomena where an optical wave interacts with the polarizability of the material, such as Brillouin scattering or polariton scattering.

As used herein, "surface plasmons," "surface plasmon polaritons," or "plasmons" refer to the collective oscillations of free electrons at plasmonic surfaces, such as metals. These oscillations result in self-sustaining, surface electromagnetic waves that propagate in a direction parallel to the metal/dielectric (or metal/vacuum) interface. Since the wave is on the boundary of the metal and the external medium (air or water for example), these oscillations are very sensitive to any change of this boundary, such as, for example, the adsorption of a biomolecular target to the metal surface. Subsequently, the oscillating electrons radiate electromagnetic radiation with the same frequency as the oscillating electrons. It is this re-radiation of light at the same incident wavelength that is referred to as "plasmon scatter." These oscillations can also give rise to the intense colors of solutions of plasmonic nanoparticles and/or intense scattering. In the case of metallic plasmonic nanoparticles, excitation by light results in localized collective electron charge oscillations, i.e., "localized surface plasmon polaritions" (LSPRs). They exhibit enhanced near-field amplitude at the resonance wavelength. This field is highly localized at the nanoparticle and decays rapidly away from the plasmonic nanoparticle/dieletric interface into the dielectric background, though far-field scattering by the particle can also enhanced by the resonance. LSPR has very high spatial resolution at a subwavelength level, and is determined by the size of plasmonic nanoparticles. "Plasmon absorption," as used herein, refers to the extinction of light (by absorption and scattering) caused by metal surface plasmons. Surface plasmon resonance can be used with the methods and assays described herein for measuring the interaction between CD1a and a ligand that binds CD1a, in the presence or absence of a candidate agent to determine if the candidate agent disrupts or inhibits the interaction between CD1a and its ligand.

Also contemplated herein are screening assays utilizing functional T-cell experiments. In one embodiment, the functional T-cell experiment is performed in conjunction with at least one other screening assay as described herein, for example, to further test a candidate agent identified through bio-layer interferometry or surface plasmon resonance. In another embodiment, the functional T-cell experiment is performed independently of other screening assays described herein. The functional T-cell assay is an in vitro assay comprising CD1a-expressing antigen-presenting cells (APCs) in co-culture with CD1a-restricted T cells. The T-cells are responsive to CD1a and any interference with the proper display of CD1a on the cell surface of APCs hampers T-cell stimulation. The T-cell co-culture is incubated in the presence of absence of at least one candidate agent to be tested. T-cell activation, T-cell proliferation and cytokine production can be measured, alone or in combination, using ELISA. Specific cytokines contemplated include, but are not limited to, IFN-γ and IL-17. Inhibition of CD1a-mediated T-cell activation indicates that candidate agent is efficacious for inhibiting CD1a-mediated inflammation.

Also contemplated herein is an in vitro screening assay utilizing CD1a-transgenic mice as described herein. For example, inflammatory skin disease is induced using the urushiol-mediated contact dermatitis model of psoriasis model described herein. Candidate agents are administered to the animals and the degree of inflammatory skin disease is assessed as described herein. One of skill in the art can design such screening assays to include dose-response curves of each candidate agent.

The screening assays described herein can be used alone, or in combination with at least one other screening assay as described herein.

Also contemplated herein are screening kits for use in research or development of therapeutics for the treatment of psoriasis, urushiol-mediated inflammation, or other inflammatory skin diseases. Such kits can include one or more of the following agents: recombinant CD1a, a lipid ligand, a CD1a-expressing antigen presenting cell, a CD1a-restricted T-cell, CD1a-transgenic mouse model, a positive control, various buffers, reagents etc., and instructions for use.

It is understood that the foregoing description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

Some embodiments of the present invention can be defined as any of the following paragraphs:

[1] A method for treating or preventing an inflammatory skin disease, the method comprising: administering a therapeutically effective amount of an inhibitor of CD1a to a subject having an inflammatory skin disease, thereby treating or preventing the inflammatory skin disease.

[2] The method of paragraph 1, wherein the inhibitor of CD1a inhibits CD1a expression and/or activity.

[3] The method of paragraph 2, wherein the inhibitor of CD1a expression is an RNA interference molecule or a small molecule.

[4] The method of paragraph 2, wherein the inhibitor of CD1a activity is a small molecule, an antibody or fragment thereof, or a peptide.

[5] The method of paragraph 1, wherein the inflammatory skin disease is a T-cell mediated skin disease or disorder.

[6] The method of paragraph 1, wherein the inflammatory skin disease is urushiol-induced contact dermatitis.

[7] The method of paragraph 1, wherein the inflammatory skin disease is psoriasis and/or atopic dermatitis.

[8] The method of paragraph 2 or 4, wherein the inhibitor of CD1a activity inhibits binding of a ligand to CD1a or CD1a-mediated antigen presenting activity.

[9] The method of paragraph 8, wherein the ligand is urushiol.

[10] The method of paragraph 2 or 4, wherein the inhibitor of CD1a activity inhibits antigen-presenting activity of a Langerhans cell.

[11] A pharmaceutical composition for treating an inflammatory skin disease, the composition comprising a therapeutically effective amount of an inhibitor of CD1a and a pharmaceutically acceptable carrier.

[12] The composition of paragraph 11, wherein the inhibitor of CD1a is selected from the group consisting of: an RNA interference molecule, a small molecule, a peptide, and an antibody or fragment thereof.

[13] The composition of paragraph 11, wherein the inhibitor of CD1a inhibits CD1a expression and/or activity.

[14] The composition of paragraph 13, wherein the inhibitor of CD1a expression is an RNA interference molecule or a small molecule.

[15] The composition of paragraph 13, wherein the inhibitor of CD1a activity is a small molecule, an antibody or fragment thereof, or a peptide.

[16] The composition of paragraph 11, wherein the inflammatory skin disease is a T-cell mediated skin disease or disorder.

[17] The composition of paragraph 11, wherein the inflammatory skin disease is urushiol-induced contact dermatitis.

[18] The composition of paragraph 11, wherein the inflammatory skin disease is psoriasis and/or atopic dermatitis.

[19] The composition of paragraph 13 or 15, wherein the inhibitor of CD1a activity inhibits binding of a ligand to CD1a or CD1a-mediated antigen presenting activity.

[20] The composition of paragraph 19, wherein the ligand is urushiol.

[21] The composition of paragraph 13 or 15, wherein the inhibitor of CD1a activity inhibits antigen-presenting activity of a Langerhans cell.

[22] The composition of any one of paragraphs 11-21, wherein the composition is formulated for systemic delivery.

[23] The composition of any one of paragraphs 11-21, wherein the composition is formulated for topical delivery.

[24] A method for screening a candidate agent for treating an inflammatory skin disease, the method comprising:
a. contacting a Langerhans cell or population of Langerhans cells with an agent,
b. measuring expression and/or activity of CD1a in the cell or population of cells, wherein a decrease in expression and/or activity of CD1a indicates that the agent is a candidate agent for the treatment of an inflammatory skin disease.

[25] The method of paragraph 24, wherein the candidate agent is selected from the group consisting of: an RNA interference molecule, a small molecule, a peptide, and an antibody or fragment thereof.

[26] An assay comprising:
a. contacting a population of Langerhans cells with a candidate agent, b. contacting the cells of step (a) with a labeled CD1a ligand,
c. measuring the intensity of the signal from the bound, detectable ligand,
d. comparing the measured intensity of the signal with a reference value and if the measured intensity is decreased relative to the reference value,
e. identifying the candidate agent as an inhibitor of CD1a expression and/or activity in the cell.

[27] The method of paragraph 26, wherein the CD1a ligand is urushiol.

[28] An inhibitor of CD1a for use in the treatment or prevention of an inflammatory skin disease.

[29] Use of an inhibitor of CD1a for the manufacture of a medicament for the treatment or prevention of an inflammatory skin disease.

[30] Use of paragraphs 28 or 29, wherein the inhibitor of CD1a inhibits CD1a expression and/or activity.

[31] Use of paragraph 30, wherein the inhibitor of CD1a expression is an RNA interference molecule or a small molecule.

[32] Use of paragraph 30, wherein the inhibitor of CD1a activity is a small molecule, an antibody or fragment thereof, or a peptide.

[33] Use of paragraph 30 or 32, wherein the inhibitor of CD1a activity inhibits binding of a ligand to CD1a or CD1a-mediated antigen presenting activity.

[34] Use of paragraph 33, wherein the ligand is urushiol.

[35] Use of paragraph 30 or 32, wherein the inhibitor of CD1a activity inhibits antigen-presenting activity of a Langerhans cell.

[36] Use of any one of paragraphs 28-35, wherein the inflammatory skin disease is a T-cell mediated skin disease or disorder.

[37] Use of any one of paragraphs 28-36, wherein the inflammatory skin disease is urushiol-induced contact dermatitis.

[38] Use of any one of paragraphs 28-37, wherein the inflammatory skin disease is psoriasis and/or atopic dermatitis.

[39] Use of any one of paragraphs 28-38, wherein the inhibitor of CD1a is formulated for systemic and/or topical delivery.

EXAMPLES

Example 1

We discovered the function of the molecule CD1a expressed on Langerhans cells in the skin in the generation of inflammatory skin diseases. These conditions include contact dermatitis to Poison Ivy as well as psoriasis. Our research demonstrates that CD1a mediates an inflammatory T-cell response that is characterized by the prominent production of cytokines like IL-17. Importantly, treatment with an experimental antibody against CD1a totally abrogates skin inflammation. This forms the basis for a therapeutic treatment to target CD1a with specific antibodies, small molecule inhibitors, or RNAi to prevent, treat or even cure skin disease. Current treatment options for psoriasis, such as biologics blocking cytokines, are limited due to restricted efficacy and substantial side effects. Therefore, due to the highly specific, mechanistic nature of treatment, CD1a-based therapy has great potential to improve outcomes of inflammatory skin diseases while minimizing side effects.

Figure 1B:
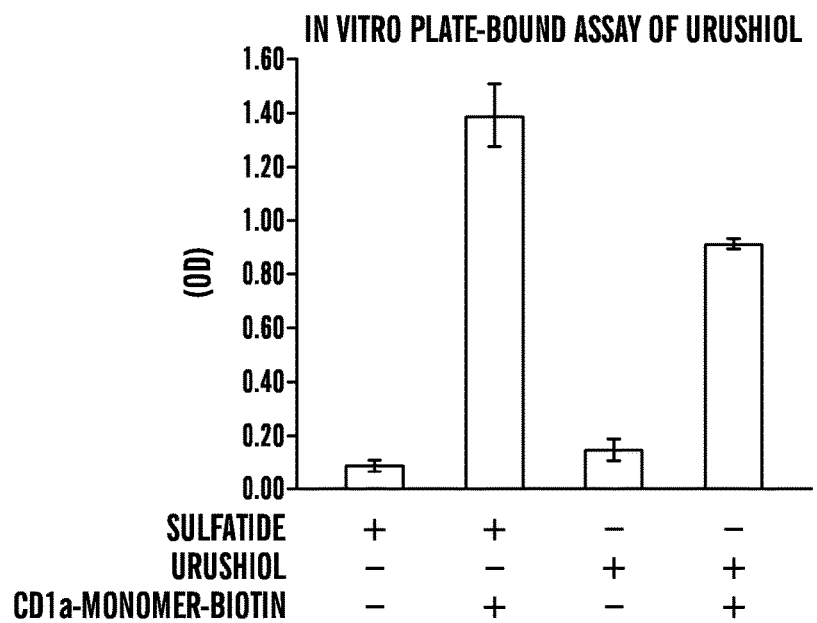

Central to our invention is the discovery that CD1a expressed on Langerhans cells is able to mediate skin inflammation through the induction of CD1a-restricted T cells. Accordingly, T cells stimulated by CD1a produce inflammatory cytokines such as interferon (IFN) gamma and IL-17 that facilitate the development of inflammatory skin disease (FIG. 1A). The CD1a-mediated mechanism holds true for diverse skin diseases, including poison ivy contact dermatitis as well as psoriasis. To demonstrate the importance of CD1a in the immune response to poison ivy, we tested first whether the poison ivy-derived lipid molecule called urushiol represents a ligand for CD1a. For this purpose, we performed a plate-bound binding assay, using purified urushiol and recombinant CD1a. After coating the microtiter plates with urushiol or the known CD1a ligand sulfatide as positive control, plates were washed and subsequently incubated with biotinylated CD1a. Following incubation with streptavidin-peroxidase and the respective chromogenic enzyme substrate, optical density was measured indicating binding efficiency. When compared to the positive control sulfatide, urushiol clearly showed specific binding to CD1a (FIG. 1B). Thus, urushiol from poison ivy is a ligand for CD1a.

Figure 2A:
FIGS. 2A-2D shows the effect of urushiol on inflammation in CD1a-transgenic mice.
Figure 2B:
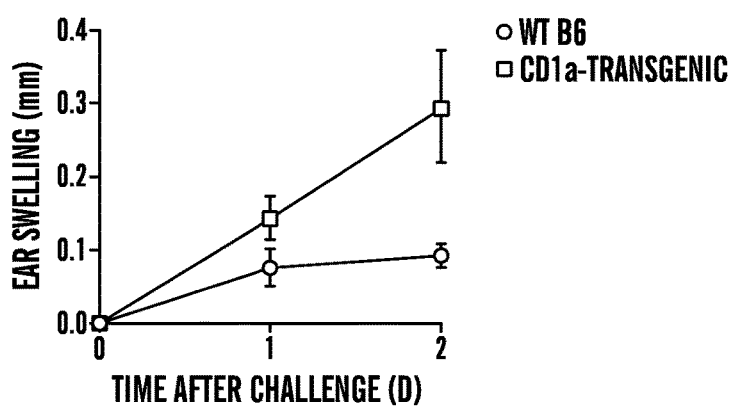
Figure 2C:
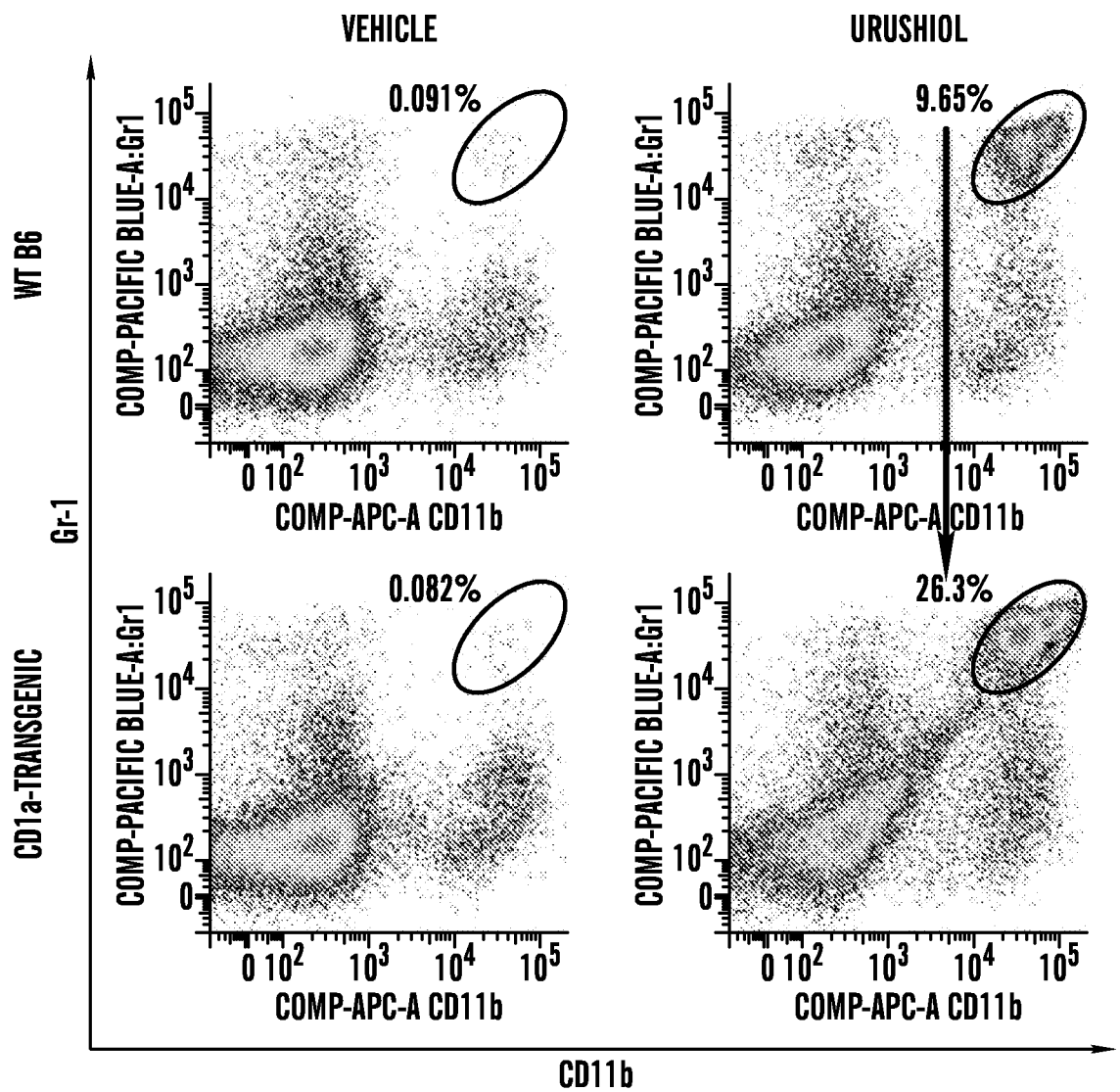
Figure 2D:
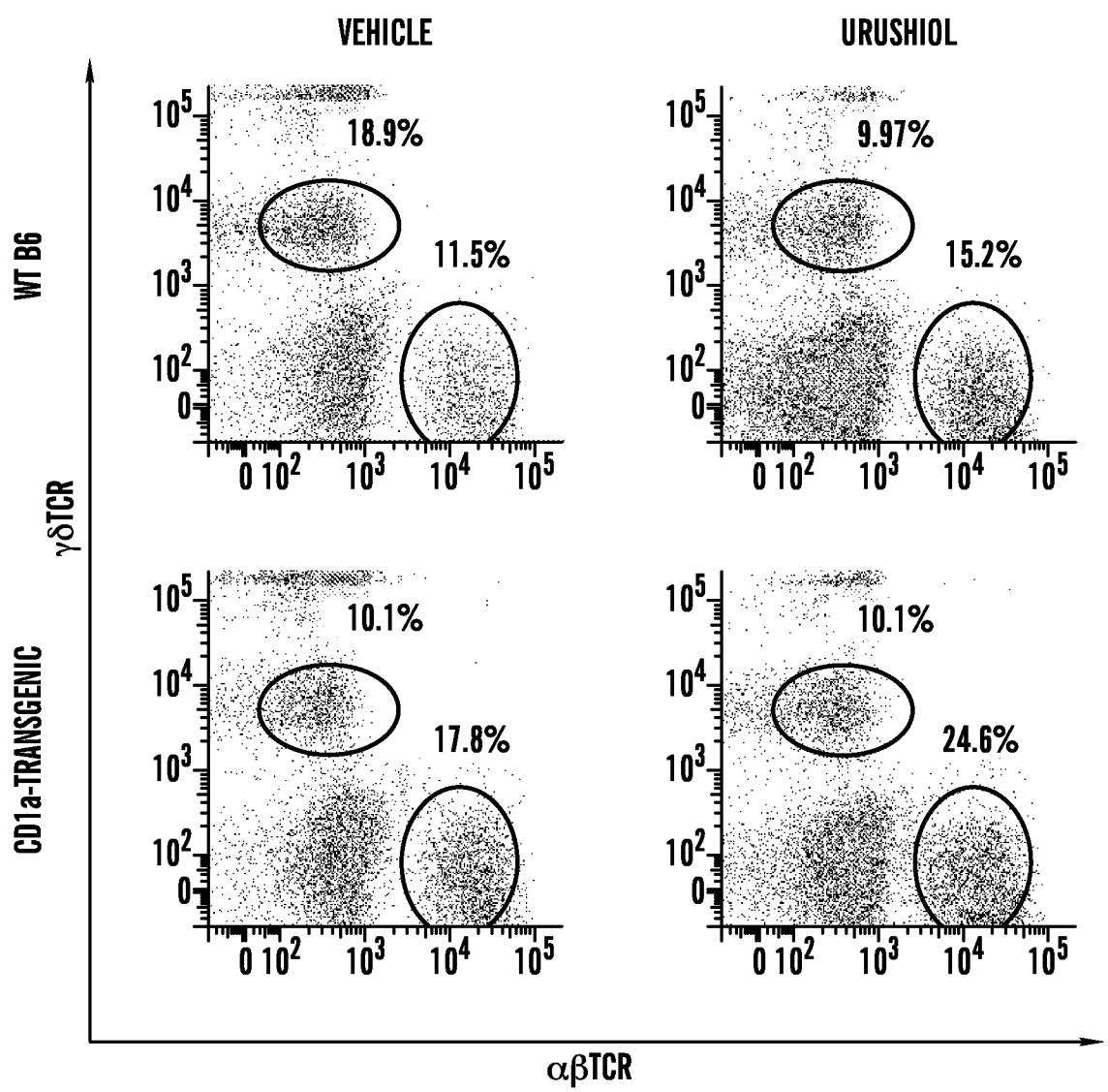
Figure 3A:
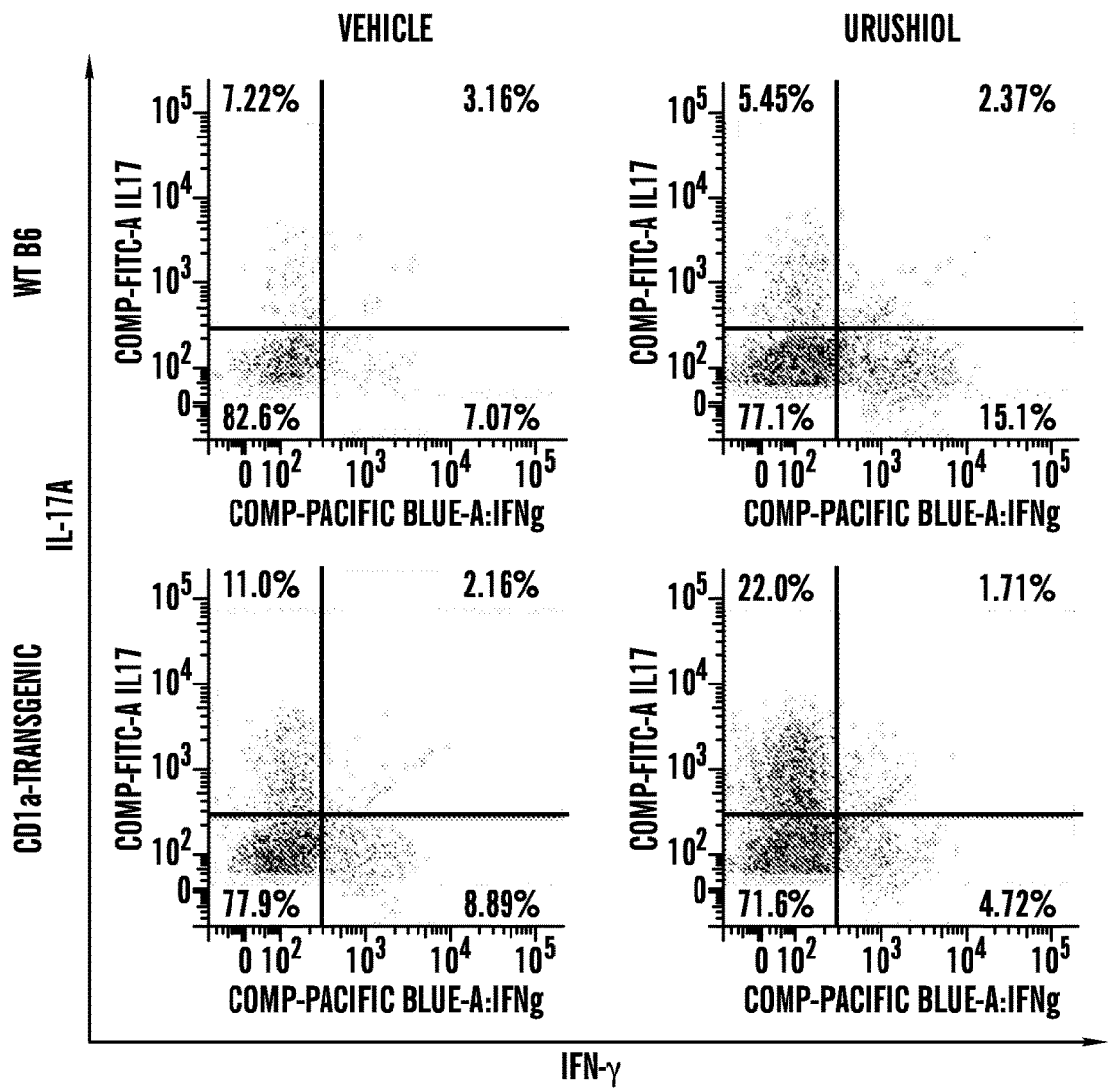
FIGS. 3A-3D show a CD1a-mediated cytokine profile in urushiol-induced dermatitis.
Figure 3B:
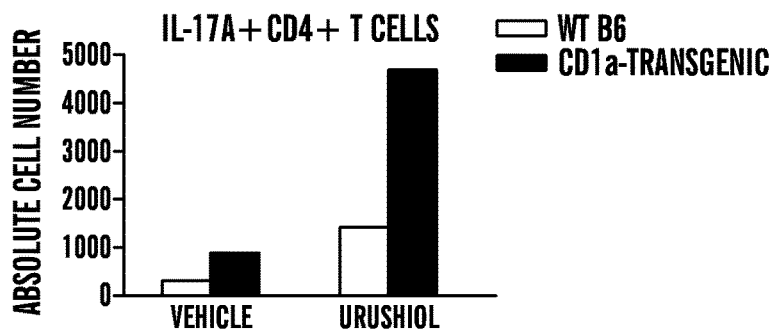
Figure 3C:
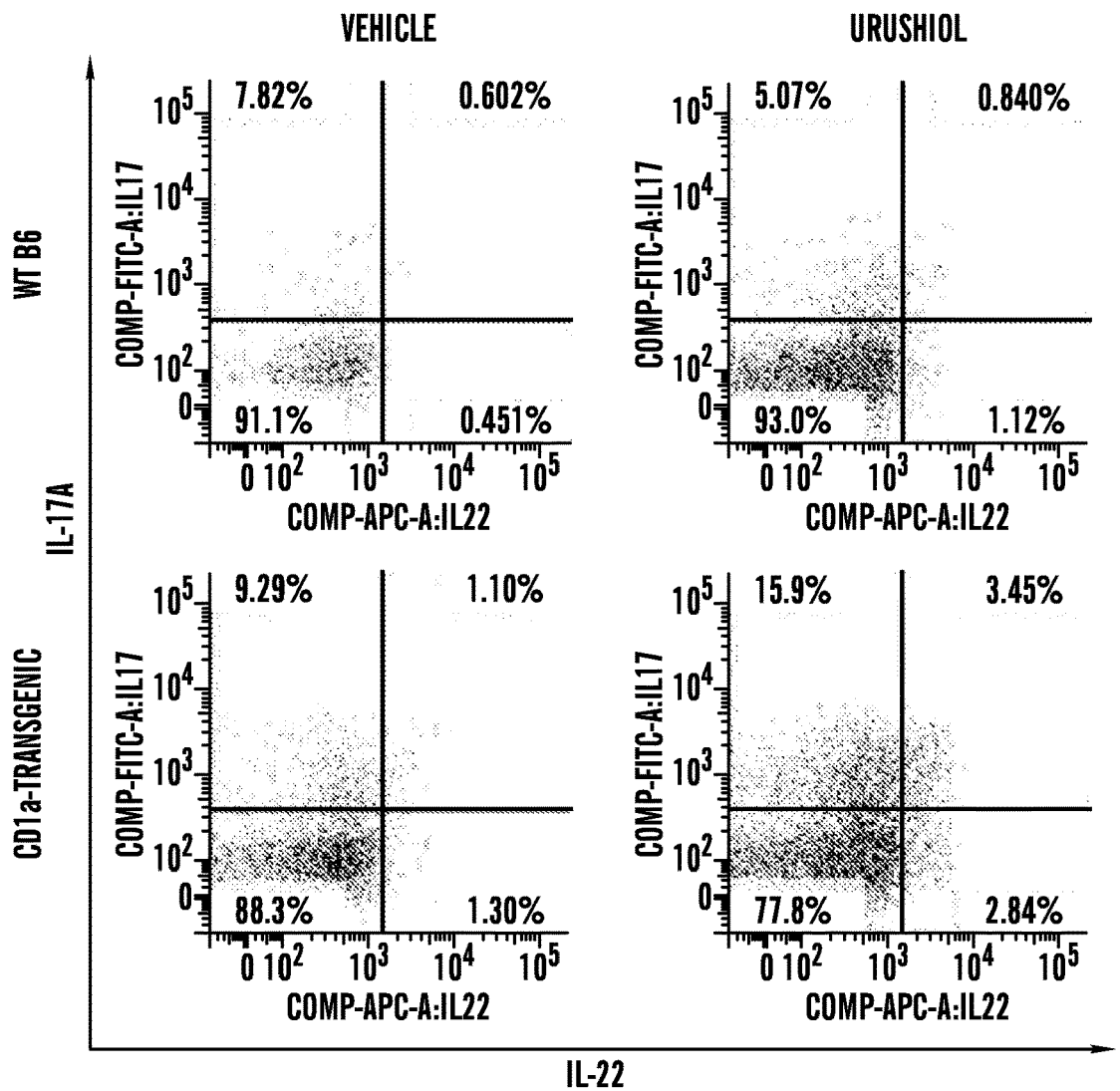
Figure 3D:
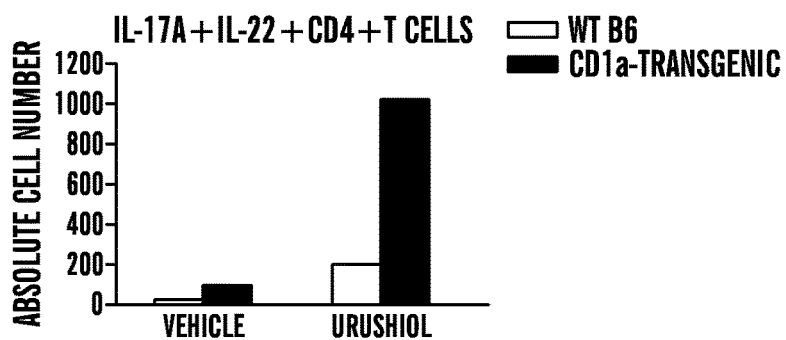

Next, we wanted to explore the function of CD1a in the in vivo response to urushiol. However, CD1a is mainly expressed in humans, and absent in experimental mice. Therefore, in vivo studies investigating CD1a function were not possible in the past. Therefore, we used mice transgenic for human CD1a to overcome that obstacle. FIG. 2A depicts the experimental set-up to investigate the skin immune response to poison ivy. Accordingly, CD1a-transgenic mice compared to wild-type (WT) mice were sensitized with urushiol on the abdomen following the epicutaneous route. Five days later, mice were challenged on the ear skin, prior to harvesting of inflamed ears and draining lymph nodes 48 h after challenge. Measuring the ear thickness 2 days after urushiol challenge revealed drastically increased ear swelling in CD1a-transgenic mice when compared to WT controls, indicating strongly amplified inflammation in the presence of CD1a (FIG. 2B). Subsequently, we isolated the inflammatory cells from the ears, using in vitro enzyme digestion of ear tissues, prior to staining for neutrophils and T lymphocyte subsets. Accordingly, we stained neutrophils for the marker molecules Gr-1 and CD11b, and observed a striking increase of neutrophil infiltration in CD1a-transgenic mice using analysis by flow cytometry (FIG. 2C). Moreover, we analyzed the proportions of γδ and αβ T cells in the skin and found that specifically CD4+αβ T cells expanded in urushiol-challenged skin in a CD1a-dependent fashion (FIG. 2D).

In parallel, we also determined the cytokine profile of the T cells infiltrating the inflamed skin. Accordingly, we performed intracellular cytokine staining for IFN-γ, IL-17, and IL-22, prior to analysis by flow cytometry. Surprisingly, poison ivy failed to induce an IFN-γ response, a cytokine normally predominant in inflammation and delayed type hypersensitivity (DTH). By contrast, T cells responding to urushiol challenge mainly produced the cytokines IL-17 and IL-22 (FIGS. 3A-3D). IL-17 is known to mediate the recruitment of neutrophils, and IL-22 acts on epithelial cells to trigger their hyperproliferation, both cardinal features of skin inflammation.

Figure 4A:
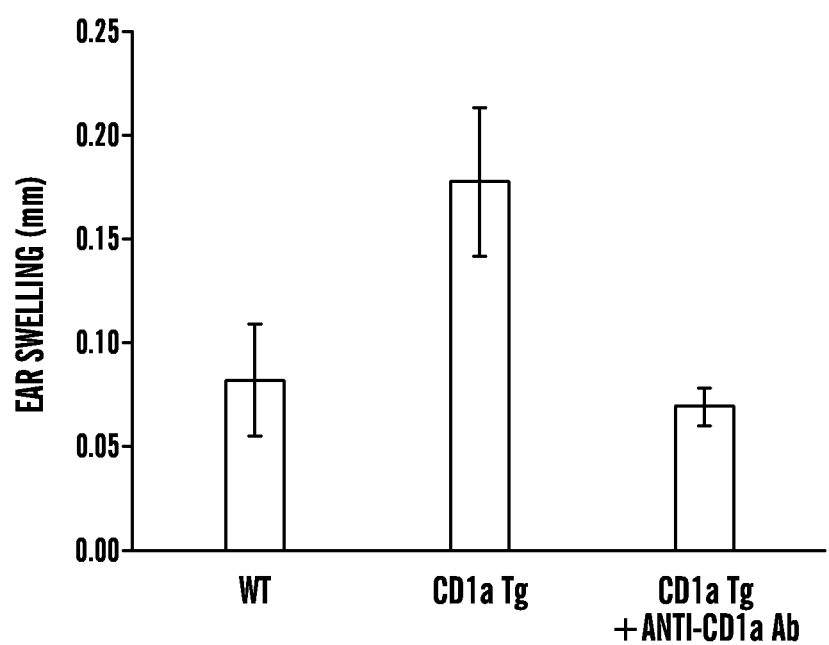
FIGS. 4A-4D show the reductive effect of an anti-CD1a blocking antibody in urushiol-treated mice.
Figure 4B:
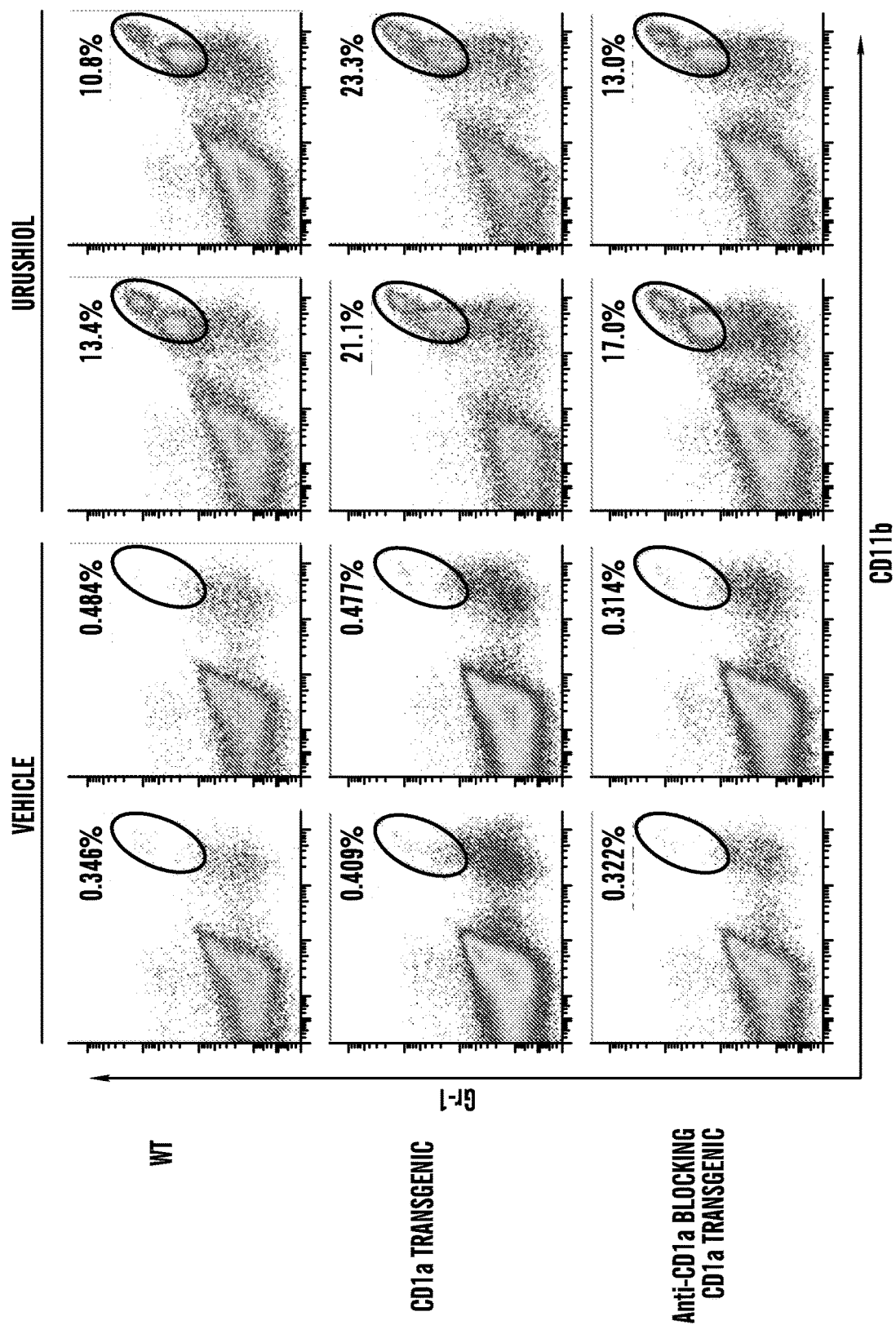
Figure 4C:
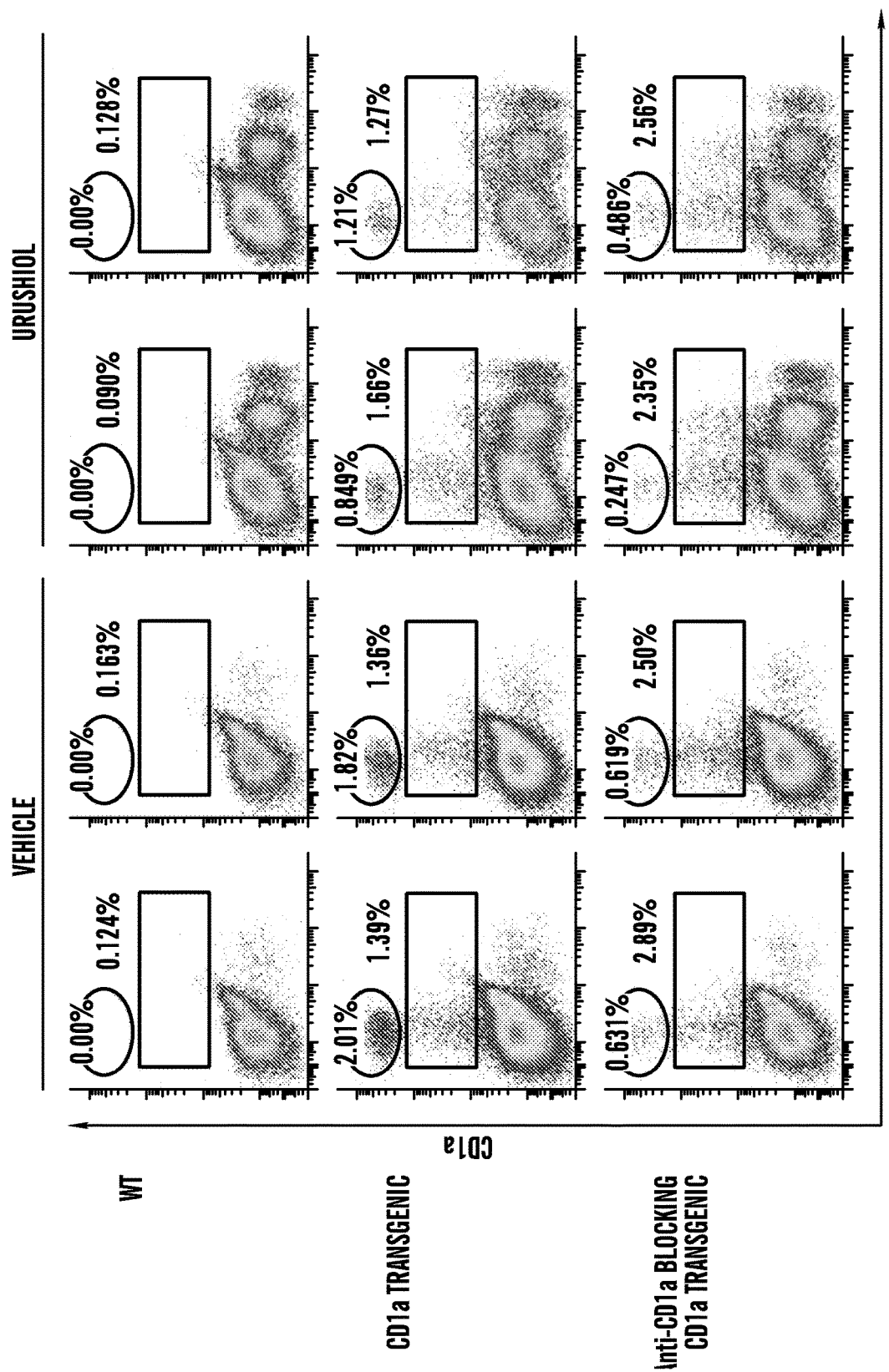
Figure 4D:
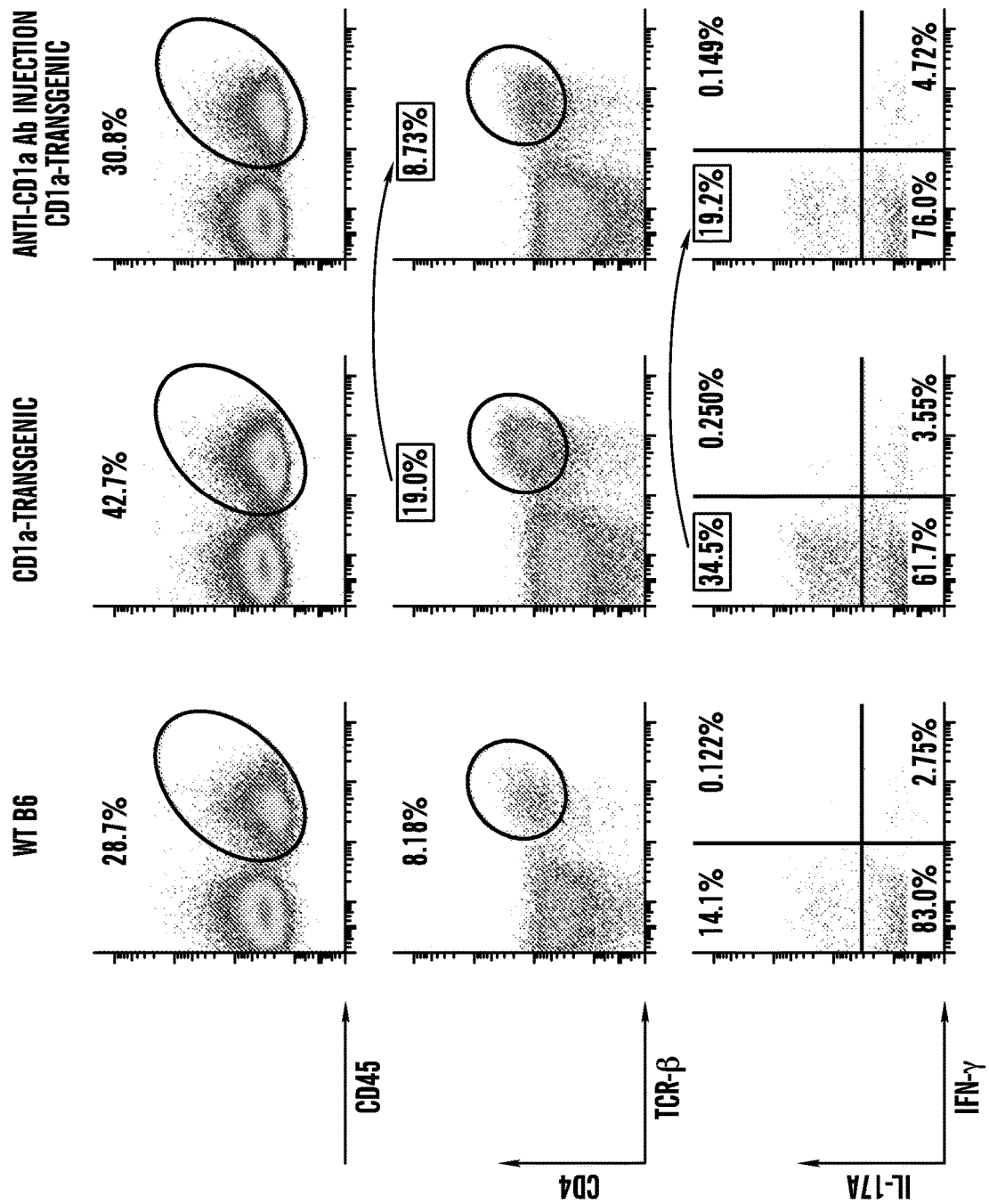

Based on our findings that CD1a promotes skin inflammation, we next aimed at developing a therapeutic strategy to target CD1a in order to abrogate skin disease. To this end, we used an experimental blocking antibody to CD1a for intraperitoneal injection of mice. The treatment schedule included five injections of 100 μg anti-CD1a starting one day prior to sensitization with urushiol and followed by injections every other day until challenge and tissue harvest. When measuring ear swelling as indicator of inflammation, we observed a striking reduction in ear thickness upon treatment with CD1a blocking antibody (FIG. 4A). This therapeutic impact on skin inflammation corresponded to the markedly reduced infiltration of neutrophils, as reflected by the reduced population of Gr-1+CD11b+ cells in anti-CD1a-treated mice measured by flow cytometry (FIG. 4B). To control for the efficiency of antibody treatment, we stained ear cells for CD1a, the crucial surface marker of Langerhans cells. Flow cytometrical analysis revealed that anti-CD1a treatment allowed for the efficient depletion of the CD1a+ cell population (FIG. 4C). Moreover, we investigated the impact of anti-CD1a treatment on the abundance of IL-17-producing CD4 T cells (also called Th17 cells). The frequency of Th17 cells was drastically increased in CD1a-transgenic mice challenged with urushiol. However, anti-CD1a treatment reduced the abundance of Th17 cells as well as their cytokine production to the levels seen in WT control animals (FIG. 4D). Taken together, we provide the proof of principle that anti-CD1a therapy abrogates skin inflammation.

Figure 5A:
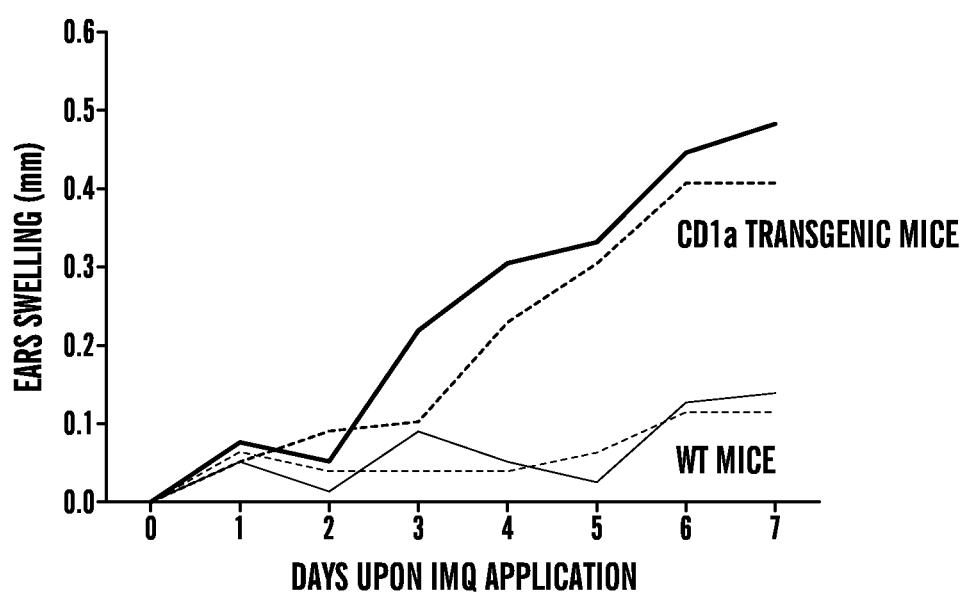
FIGS. 5A-5C show the contribution of CD1a in psoriasis.
Figure 5B:
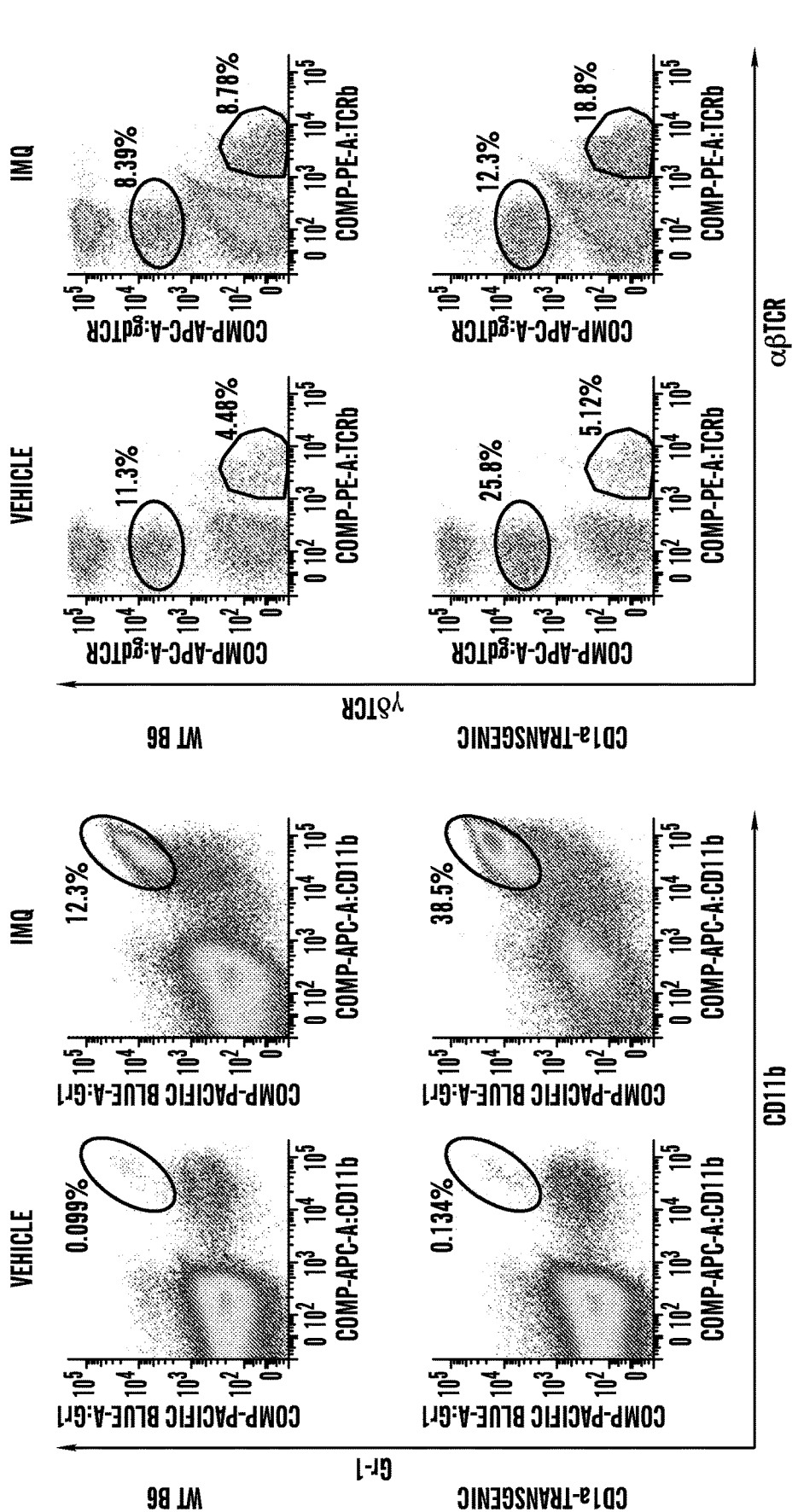
Figure 5C:
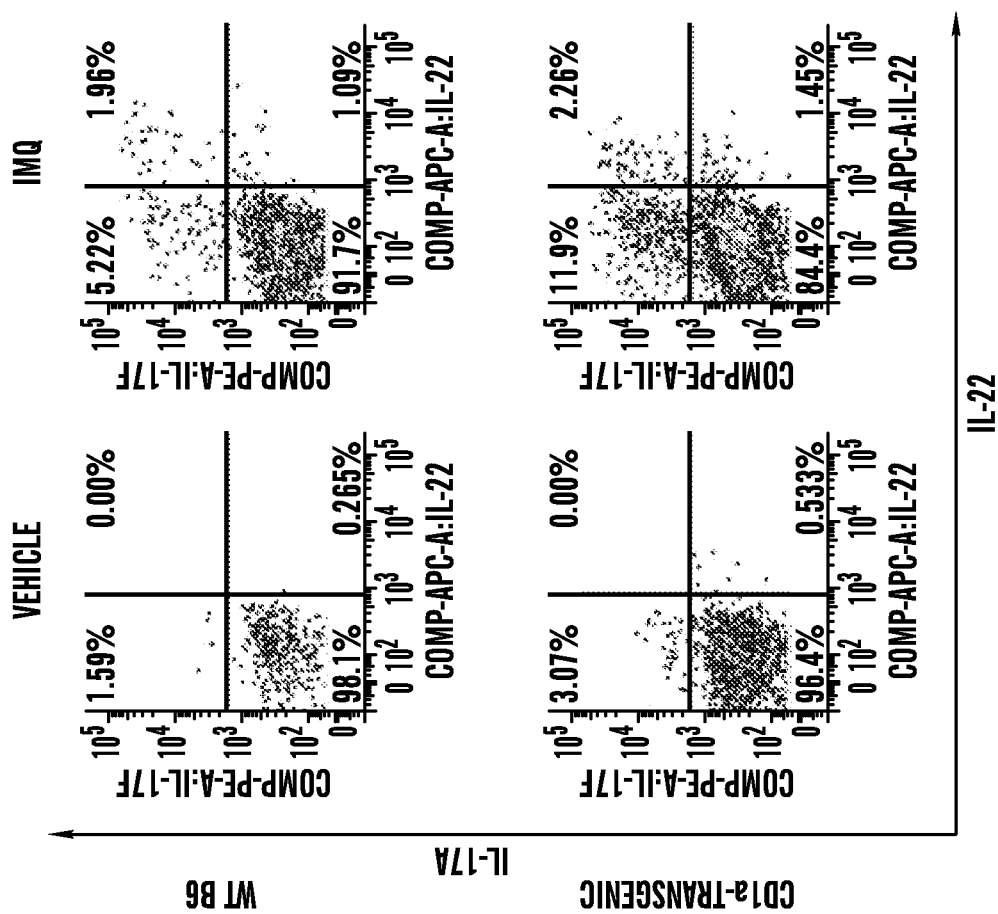

Notably, the Th17 cell phenotype that we observed in urushiol-induced contact dermatitis resembles the inflammatory process described in psoriasis. Therefore, we subsequently investigated whether CD1a also plays an important role in psoriasis. For this purpose, we used a well-established model applying the small molecule imiquimod (IMQ) to the skin of mice, which induces psoriasis-like pathology after 3-6 days of daily administration. Strikingly, CD1a-transgenic mice responded with extensive ear swelling when compared to WT controls (FIG. 5A). When analyzing the infiltrating leukocyte subsets in the ear performing flow cytometry, we observed a dramatic increase in Gr-1+CD11b+ neutrophils as well as αβ T cells in the skin of CD1a-transgenic mice (FIG. 5B). Furthermore, the inflammatory T cells mainly consisted of CD4 T cells producing IL-17 and IL-22 (FIG. 5C). These findings demonstrate that CD1a also plays an important role in psoriasis-like pathology, and that the immunological phenotype observed in CD1a-transgenic mice corresponds to what is known in psoriasis patients.

Figure 6A:
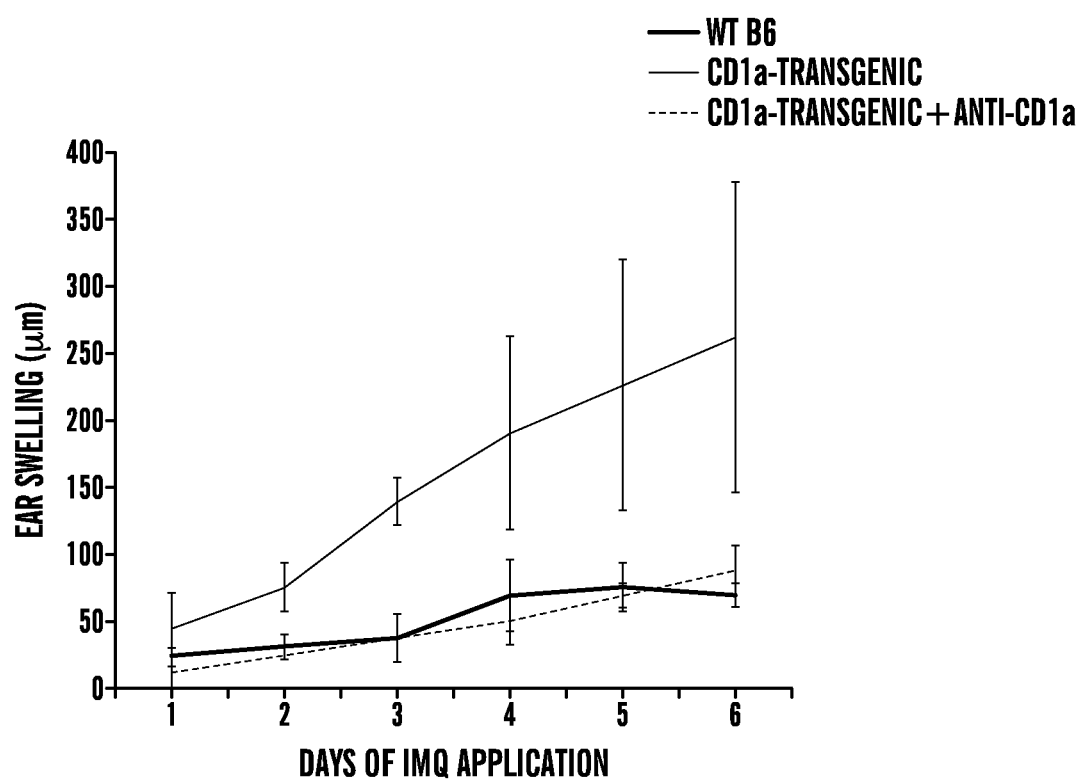
FIGS. 6A-6C show the reductive effect of anti-CD1a treatment in a psoriasis model.
Figure 6B:
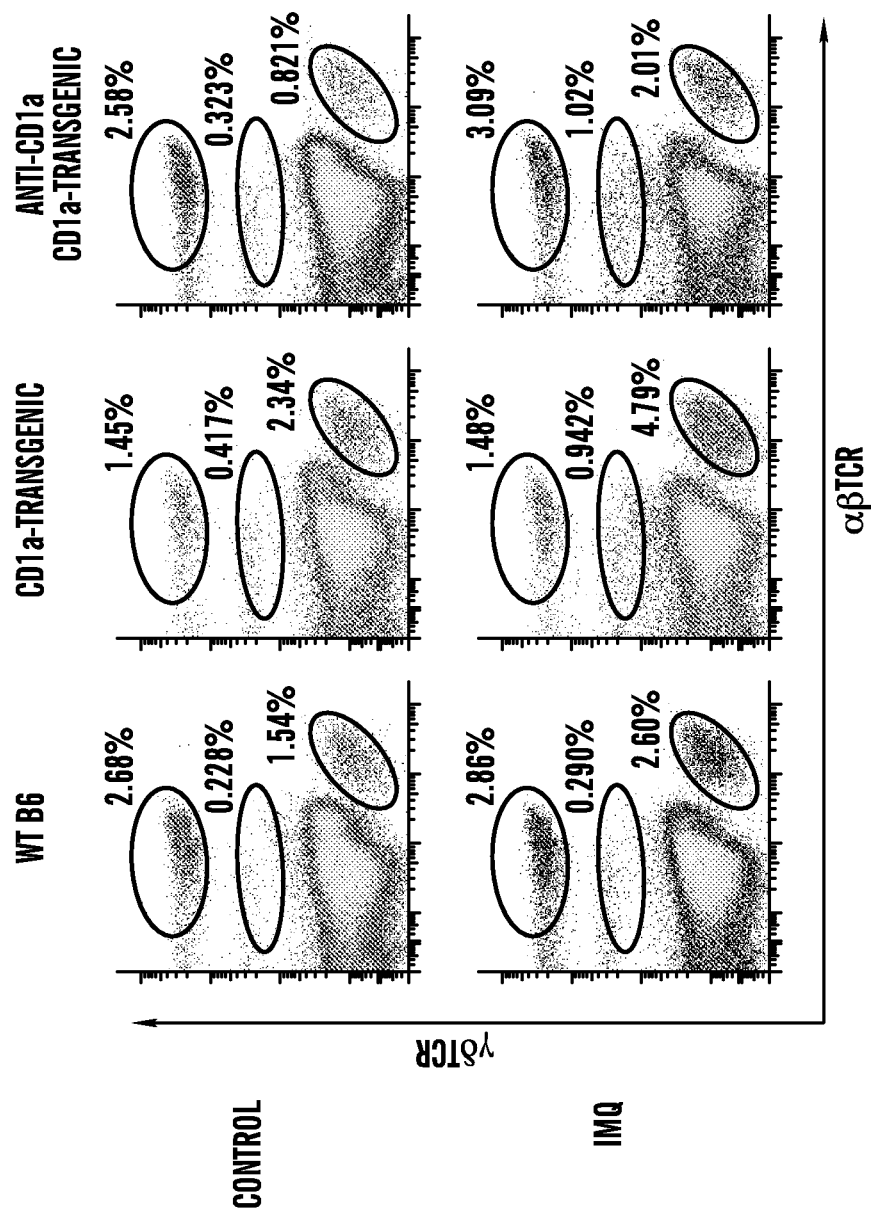
Figure 6C:
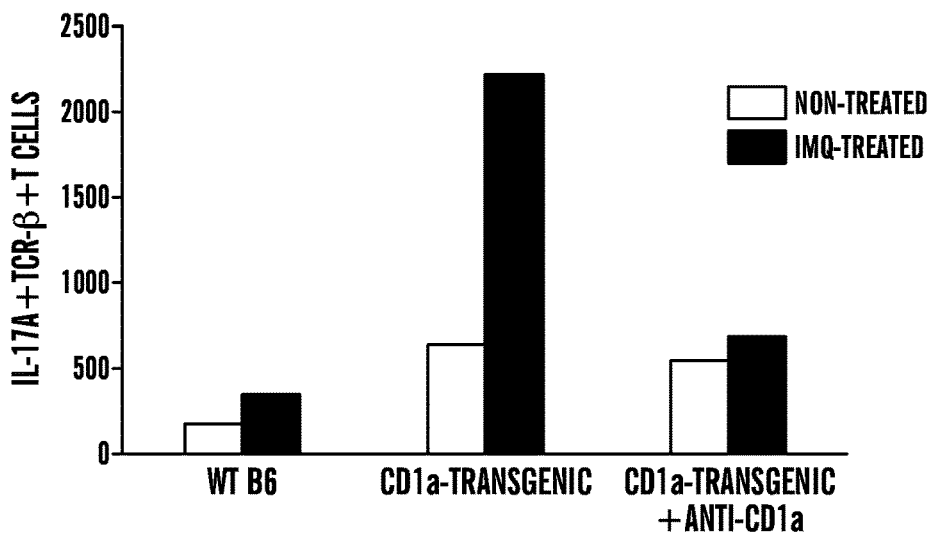

In order to test whether anti-CD1a therapy is able to abrogate skin inflammation in psoriasis, we performed IMQ treatment of mice and administered anti-CD1a antibody in parallel as described above. Ear swelling as a measure of inflammation was totally abrogated upon treatment of CD1a-transgenic mice with anti-CD1a antibody (FIG. 6A). Correspondingly, the expansion of CD4+αβ T cells in the skin was reduced to background levels as measured by flow cytometry (FIG. 6B). Of note, anti-CD1a therapy blocked the infiltration of IL-17 producing CD4 T cells. To conclude, we demonstrate that CD1a-based therapy abrogates a Th17 cell phenotype and inflammatory skin disease such as psoriasis.

Figure 7A:
FIGS. 7A-7D show that CD1a suppresses the immune response to 2, 4,-dinitro-1-fluorobenzene (DNFB).
Figure 7B:
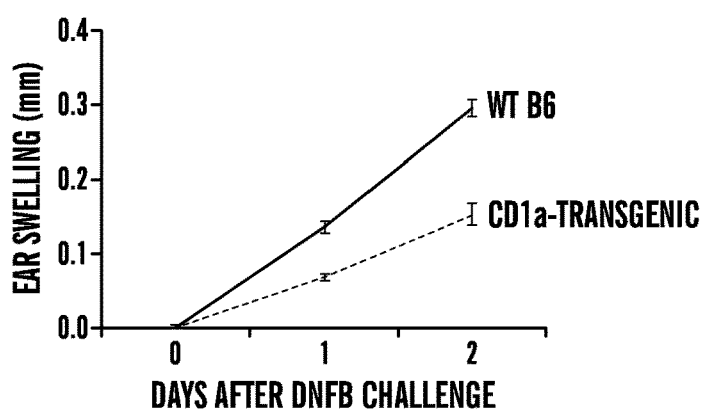
Figure 7C:
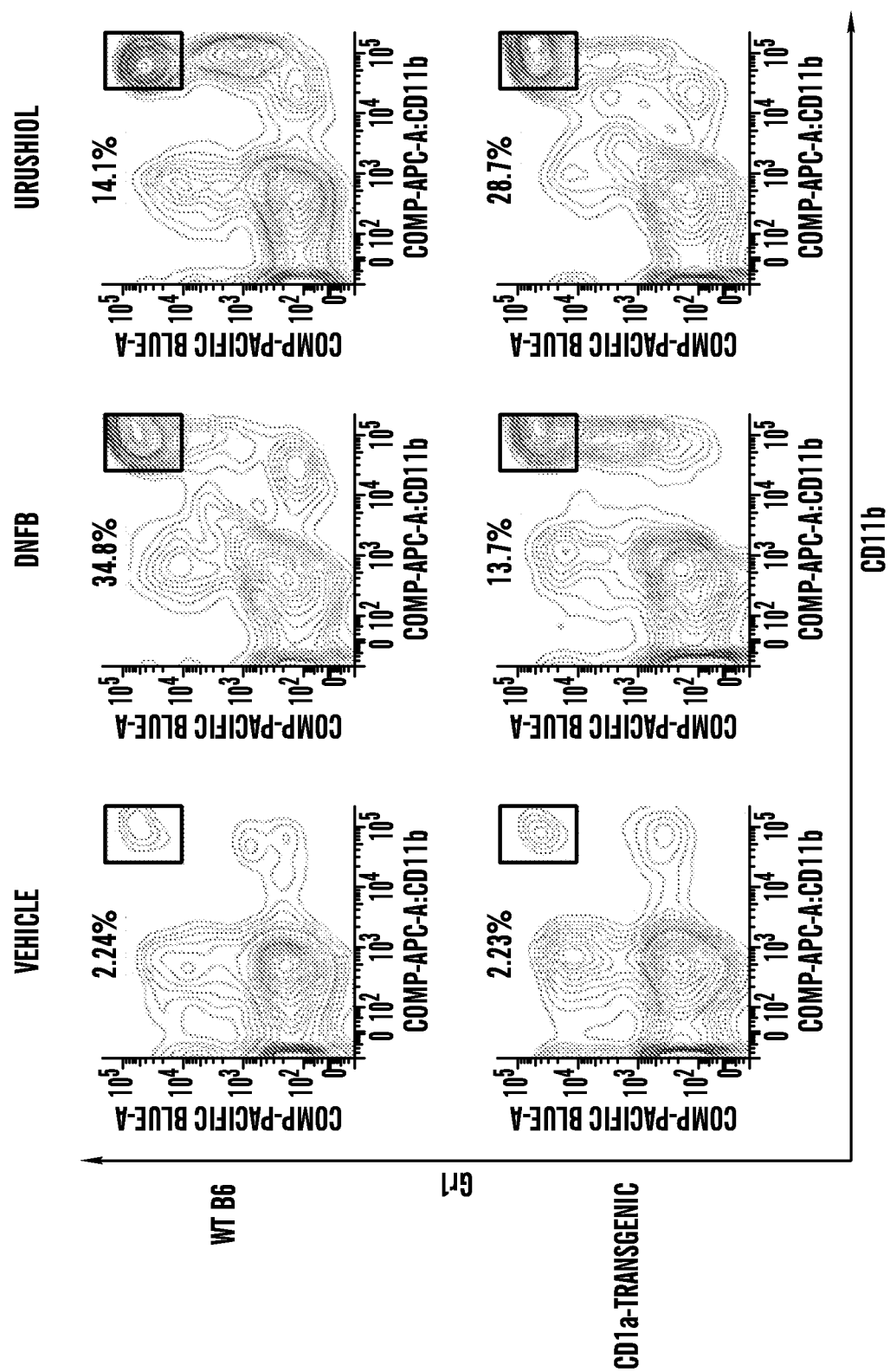
Figure 7D:
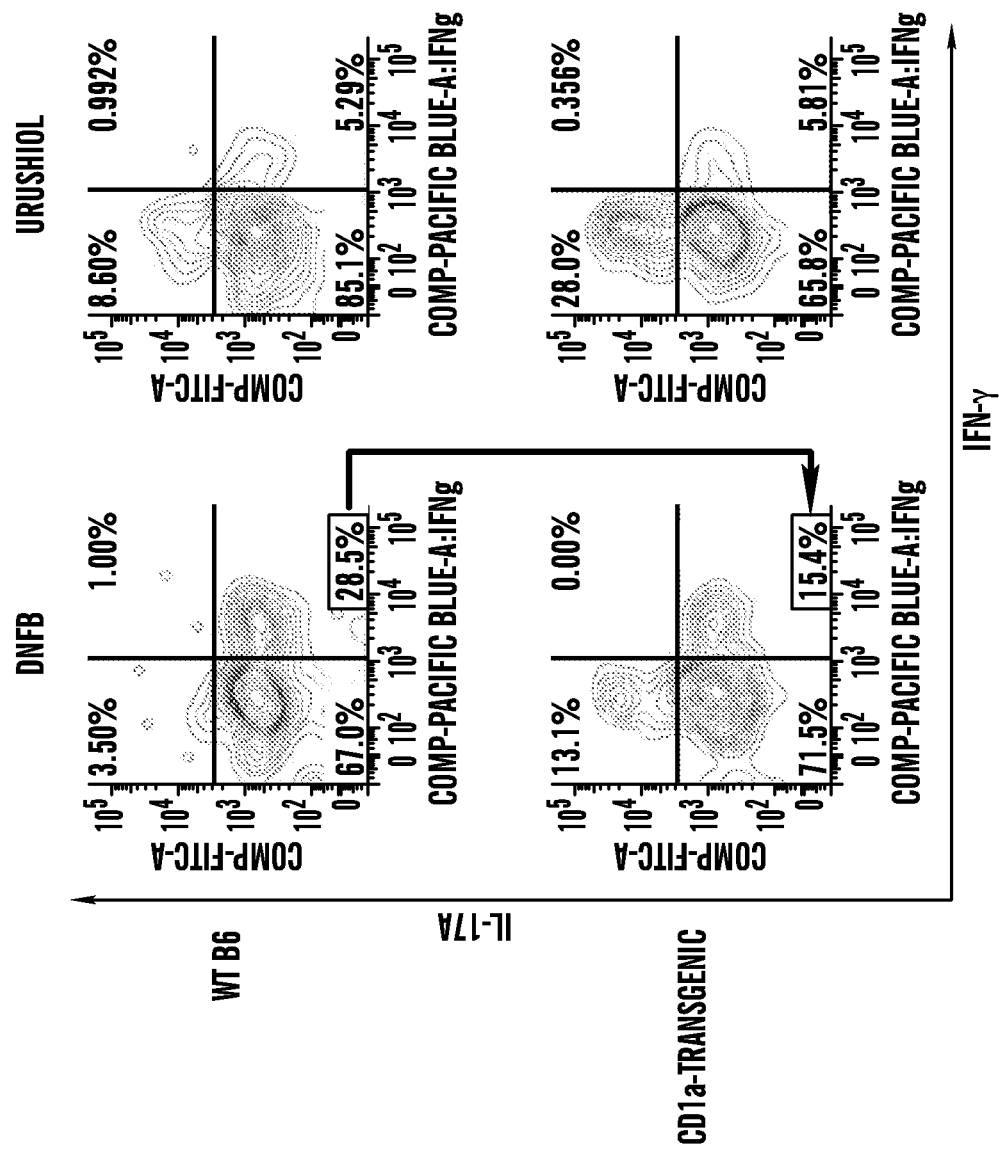

Finally, we wanted to examine whether CD1a-transgenic mice are generally prone to increased inflammatory responses. To this end, we treated mice with the well-established hapten DNFB (dinitrofluorobenzene). FIG. 7A depicts the skin sensitization and challenge schedule used for DNFB and urushiol application. Surprisingly, in contrast to poison ivy challenge, CD1a-transgenic mice responded with less inflammation to DNFB as indicated by reduction in ear swelling (FIG. 7B). Congruently, although urushiol amplified neutrophil infiltration in CD1a-transgenic mice, the abundance of inflammatory granulocytes was strikingly reduced in response to DNFB as measured by flow cytometry (FIG. 7C). It is well known that haptens like DNFB induce a prominent IFN-γ response, as we observed in WT mice (FIG. 7D). However, T cell-derived IFN-γ was significantly reduced in CD1a-transgenic animals, and the cytokine response was rather biased towards IL-17 (FIG. 7D). In conclusion, these data show that CD1a-transgenic mice are not characterized by a general increase in inflammatory responses to a variety of triggers. By contrast, the classical delayed type hypersensitivity (DTH) response to DNFB was rather decreased in the presence of CD1a. This underlines the specific nature of CD1a function in urushiol-induced contact dermatitis and psoriasis.

Figures 8A, 8B:
FIGS. 8A-8B show that CD1a mainly facilitates the expansion of CD4 T cells.

Moreover, the T cell infiltration in the skin was predominantly mediated by CD4 T cells in response to poison ivy (FIG. 8). This is in contrast to the known phenomena of CD8 T cell participation in DTH to substances like DNFB, and shows again that CD1a-mediated skin inflammation represents a distinct mechanism beyond known allergic pathways.

Furthermore, we extended the scope of possible indications for a CD1a-based drug by testing the role of CD1a in atopic dermatitis (AD). Accordingly, we treated CD1a-transgenic mice with calcipotriol (MC903), a well-established mouse model for AD. Notably, CD1a strikingly increased skin inflammation, and treatment with a CD1a-blocking antibody reduced inflammatory skin disease in this AD model.

Atopic dermatitis is an inflammatory skin disease characterized by itchy and relapsing eczematous skin lesions. It affects approximately 30% of children and 10% of adults, costing up to $3.8 billion annually in the United States. The cause of atopic dermatitis remains unclear, and there is no cure available. Recently, it has been reported that IL-22-producing CD4 T cells are associated with initiation and progression of atopic dermatitis. Therefore, it is worthwhile to test whether anti-CD1a therapy can be extended to atopic dermatitis. For this purpose, we set up a mouse model of atopic dermatitis applying MC903 (calcipotriol, Vitamin D analogue) daily on the ears of experimental mice, which triggers atopic dermatitis-like skin inflammation characterized by red, scaly, and eczematous lesions. Inflammation indicated by ear swelling and Gr1+CD11b+ granulocyte infiltration was significantly amplified in CD1a-transgenic mice when compared to WT B6 controls. Furthermore, anti-CD1a Ab injection suppressed ear swelling and granulocyte infiltration in CD1a-transgenic mice. These results suggest that CD1a promotes skin inflammation in an atopic dermatitis model, and thus could represent a novel therapeutic target for future treatment of atopic dermatitis.

Figure 9A:
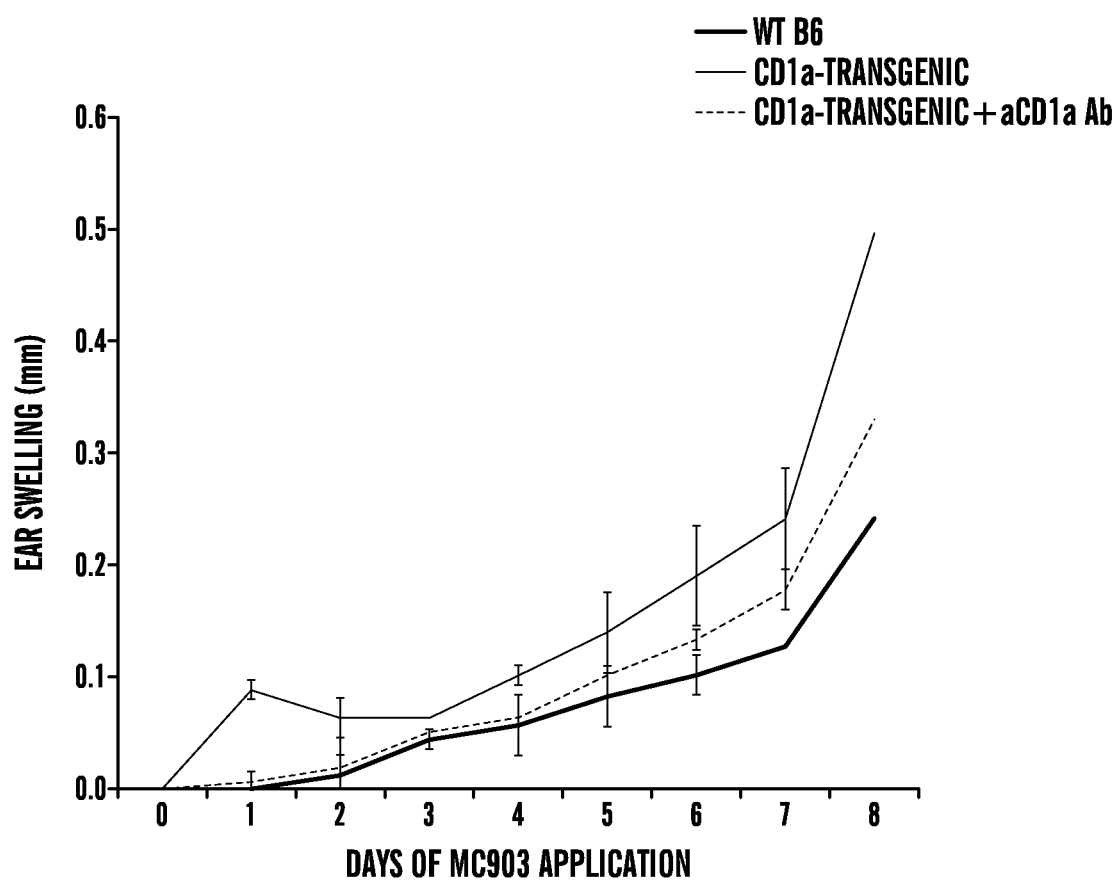
FIG. 9A-9B show that skin inflammation after MC903 application is aggravated in the presence of CD1a. The vitamin D3 analogue MC903 was used to induce atopic dermatitis-like symptoms in mice.
Figure 9B:
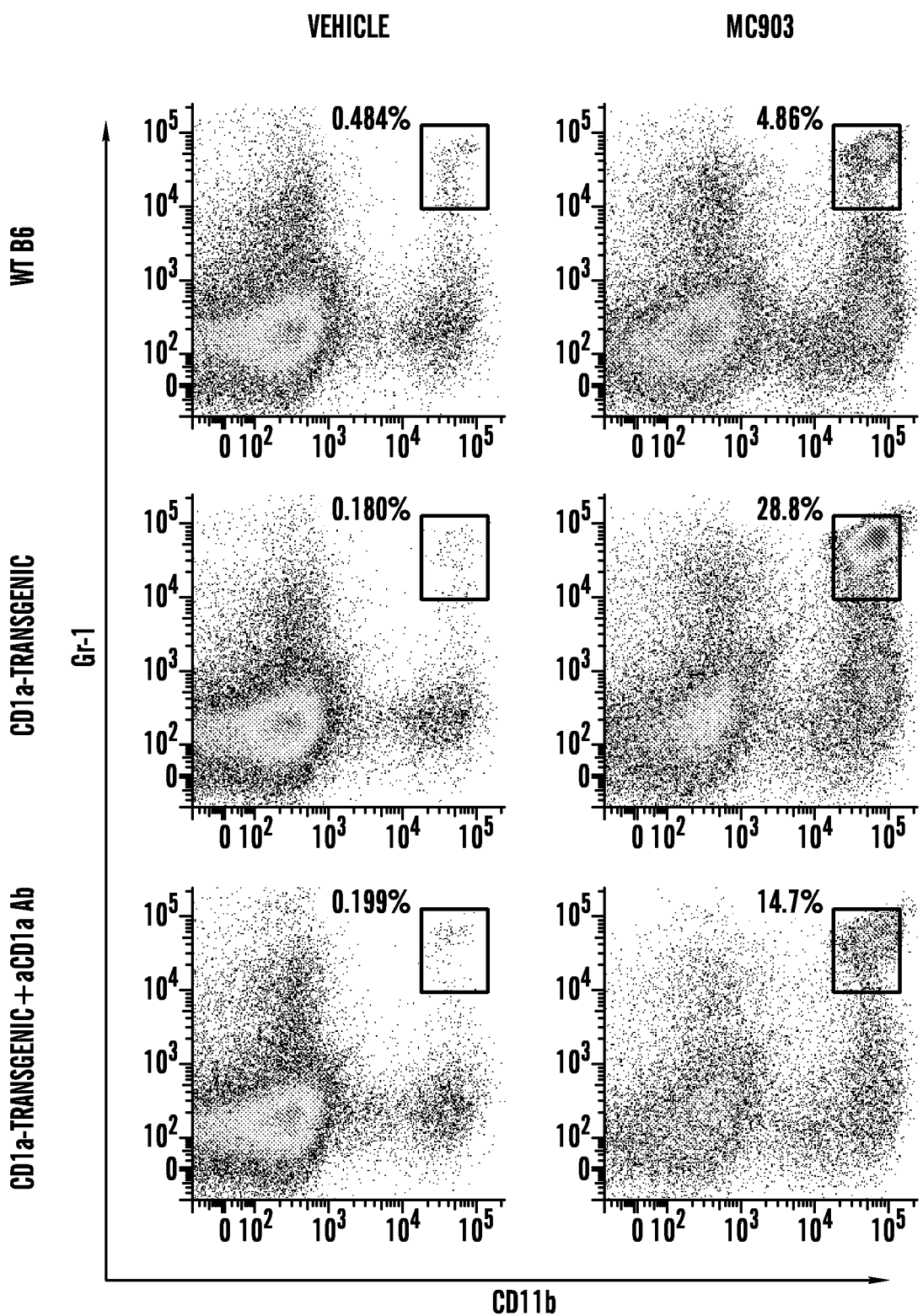

The inventors tested the contribution of CD1a presence in MC903-induced atopic dermatitis. The vitamin D3 analogue MC903 was used to induce AD-like symptoms in wild-type (WT-B6) mice, CD1a transgenic mice, and CD1a transgenic mice that were treated with an anti-CD1a Ab. For CD1a blocking, 200 μg of anti-CD1a Ab was intraperitoneally injected into CD1a-transgenic mice every other day (−1, +1, +3, +5, and +7 days before and after MC903 treatment). FIGS. 9A and 9B show that skin inflammation after MC903 application is aggravated in the presence of CD1a. FIG. 9A shows increased ear swelling in CD1a-transgenic mice that is abrogated by anti-CD1a injection. FIG. 9B shows reduction of CD11b+Gr-1+ inflammatory granulocytes in inflamed ear tissues by anti-CD1a Ab injection.

Translational Studies Using T Cells from Psoriasis Patients:

In order to investigate whether CD1a-based therapy can work in the human system, we will demonstrate the activation of CD1a-restricted T cells in psoriasis patients. Moreover, we will aim at blocking the inflammatory T cell response from psoriasis patients using an anti-CD1a antibody. These experiments will confirm that CD1a plays an important role in psoriasis patients, and that targeting of CD1a is a vital option for CD1a-based drug development against human disease. For this purpose, peripheral blood from patients suffering from moderate to severe psoriasis as well as healthy donors will be used for these tests. The T cells are isolated from the blood and subsequently co-cultured with antigen presenting cells (APCs) expressing CD1a. After incubation of APCs with T cells, cell culture supernatants are analyzed for the amount of inflammatory cytokines such as IFN-γ, IL-17, and IL-22 using ELISA. In parallel, co-cultures will be treated with an anti-CD1a antibody to block CD1a-mediated T cell stimulation. We predict that CD1a-restricted T cells expand in psoriasis patients since they are important effectors of the inflammatory response. Accordingly, we predict that cytokine responses of T cells from psoriasis patients will be increased compared to healthy donors. We further predict that CD1a blocking will abrogate inflammatory T cell responses derived from psoriasis patients. These experiments will provide confirmation of that CD1a is a vital target for treatment of inflammatory skin diseases in humans, similar to our results observed in mice.

Exemplary Screening Assays

Provided herein are exemplary screening assays contemplated for use with the methods and assays described herein. Modifications to the screening assays described herein are well within the skill set of one of ordinary skill in the art and are contemplated herein.

In order to develop a small molecule inhibitor against CD1a, a CD1a binding assay as a platform can be used to test potential inhibitors from a chemical compound library. For this purpose, we have already established a read-out using the OCTET machine (from FORTEBIO) to measure the molecular interaction between CD1a and lipid ligands with high sensitivity. The measurement principle of the OCTET is based on a technology called Bio-Layer Interferometry (BLI), which is able to determine kinetics between two binding partners comparable to surface plasmon resonance (BIACORE). However, the great advantage of the OCTET is its straightforward assay set-up, and that it is amenable to high throughput screening using a 384-well plate format. Accordingly, we use recombinant CD1a molecules coupled to a biosensor, prior to incubation with the known lipid ligand sulfatide. This experimental set-up yields sensitive and specific binding curves that reflect the molecular interaction between CD1a and sulfatide. In a next step, use pools of small organic molecules derived from a chemical compound library are tested by adding them to the CD1a-sulfatide binding assay. Subsequently, one can measure whether a small molecule candidate is able to inhibit the interaction between CD1a and its ligand.

Once small molecule candidates that block binding of CD1a to its ligand are identified, one can determine whether these inhibitors are also able to prevent T cell activation by CD1a. To this end, we can perform functional T cell experiments in vitro, using CD1a-expressing antigen-presenting cells (APCs) in co-culture with CD1a-restricted T cells. Of note, the T cells used are responsive to CD1a, and any interference with the proper display of CD1a on the cell surface of APCs hampers T cell stimulation. Subsequently, T cell co-cultures are incubated with the small molecule inhibitors from the primary screen. As indicators of T cell activation, T cell proliferation and cytokine production are measured by ELISA, including IFN-γ and IL-17. A potent small molecule inhibitor will likely totally abrogate CD1a-mediated T cell activation. This secondary screen is designed to identify a small molecule inhibitor that is also capable of shutting down T cell responses which drive the development of inflammatory skin disease.

In a third step, the potent inhibitors identified in the secondary screen are tested in vivo, using the CD1a-transgenic mice described herein. For this purpose, inflammatory skin disease is induced using our models of urushiol-mediated contact dermatitis as well as psoriasis. Accordingly, candidate inhibitors testing a variety of application schedules are administered to determine their ability to abrogate inflammatory skin disease. The small molecules with the highest potency in vivo can be tested further for toxicity and safety towards clinical development.

We claim:

1. A method for treating inflammatory skin disease, the method comprising: administering a therapeutically effective amount of a monoclonal CD1a antibody or fragment thereof to a subject having uroshiol-induced contact dermatitis, atopic dermatitis or psoriasis,
   wherein the CD1a antibody comprises:
   (i) a heavy chain complementarity determining region (HCDR) 3 consisting of the amino acid sequence of SEQ ID NO: 1,
   (ii) a HCDR2 consisting of the amino acid sequence of SEQ ID NO: 67,
   (iii) a HCDR1 consisting of the amino acid sequence of SEQ ID NO: 66,
   (iv) a light chain complementarity determining region (LCDR) 1 consisting of the amino acid sequence of SEQ ID NO: 68,
   (v) a LCDR2 consisting of the amino acid sequence of SEQ ID NO: 69, and
   (vi) a LCDR3 consisting of the amino acid sequence of SEQ ID NO: 70, thereby treating the uroshiol-induced contact dermatitis, atopic dermatitis, or psoriasis.

2. The method of claim 1, wherein the CD1a antibody is a human or humanized antibody.

* * * * *

SEQUENCE LISTING

```
<160> NUMBER OF SEQ ID NOS: 72

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized - HCDR3 of SC02-113

<400> SEQUENCE: 1

Ala Pro Tyr Met Met Tyr Phe Asp Ser
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

-continued

<223> OTHER INFORMATION: Chemically synthesized - HCDR3 of SC02-114

<400> SEQUENCE: 2

Glu Thr Trp Trp Gln Ser Phe Asp Tyr
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized - HCDR3 of SC02-115

<400> SEQUENCE: 3

Ser Gln Met Pro Ser Tyr Phe Asp Tyr
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized - HCDR3 of SC02-116

<400> SEQUENCE: 4

Asp Ala Leu Trp Leu Ala Phe Asp Tyr
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized - HCDR3 of SC02-117

<400> SEQUENCE: 5

Ser Thr Pro Trp Phe Ser Phe Asp Tyr
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized - HCDR3 of SC02-118

<400> SEQUENCE: 6

Ser Ala Trp Trp Leu Ser Phe Asp Ser
1               5

<210> SEQ ID NO 7
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

```
<220> FEATURE:
<223> OTHER INFORMATION: Chemically synthesized - Variable region of
      heavy chain of 02-113
<220> FEATURE:
<221> NAME/KEY: CDS
<222> LOCATION: (1)..(351)

<400> SEQUENCE: 7 cag gtg cag ctg cag gag tcc ggc gca gga ctg ttg aag cct tcg gag      48
Gln Val Gln Leu Gln Glu Ser Gly Ala Gly Leu Leu Lys Pro Ser Glu
1               5                   10                  15 acc ctg tcc ctc acc tgc gct gtc tat ggt ggg tct ttc agt ggc tac      96
Thr Leu Ser Leu Thr Cys Ala Val Tyr Gly Gly Ser Phe Ser Gly Tyr
            20                  25                  30 tac tgg agc tgg atc cgg cag ccc cca ggg aag gga ctg gag tgg att     144
Tyr Trp Ser Trp Ile Arg Gln Pro Pro Gly Lys Gly Leu Glu Trp Ile
        35                  40                  45 ggg tat atc tat tac agt ggg agc acc aac tac aac ccc tcc ctc aag     192
Gly Tyr Ile Tyr Tyr Ser Gly Ser Thr Asn Tyr Asn Pro Ser Leu Lys
    50                  55                  60 agt cga gtc acc ata tca gta gac acg tcc aag aac cag ttc tcc ctg     240
Ser Arg Val Thr Ile Ser Val Asp Thr Ser Lys Asn Gln Phe Ser Leu
65                  70                  75                  80 aag ctg agc tct gtg acc gct gcg gac acg gcc gtg tat tac tgt gca     288
Lys Leu Ser Ser Val Thr Ala Ala Asp Thr Ala Val Tyr Tyr Cys Ala
                85                  90                  95 aag gcc cct tat atg atg tat ttt gac tcc tgg ggc cag ggc acc ctg     336
Lys Ala Pro Tyr Met Met Tyr Phe Asp Ser Trp Gly Gln Gly Thr Leu
            100                 105                 110 gtg acc gtc tcc agc                                                 351
Val Thr Val Ser Ser
        115

<210> SEQ ID NO 8
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chemically synthesized - Variable region of
      heavy chain of 02-113

<400> SEQUENCE: 8

Gln Val Gln Leu Gln Glu Ser Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Lys Ala Pro Tyr Met Met Tyr Phe Asp Ser Trp Gly Gln Gly Thr Leu
            100                 105                 110

Val Thr Val Ser Ser
        115
```

<210> SEQ ID NO 9
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Chemically synthesized - Variable region of
      heavy chain of 02-114
<220> FEATURE:
<221> NAME/KEY: CDS
<222> LOCATION: (1)..(354)

<400> SEQUENCE: 9

```
gag gtg cag ctg gtg gag tct ggg gga ggc ttg gta cag cct ggg ggg       48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttc agt agc tat       96
Ser Leu Arg Leu Ser Cys Ala Ala Ser Gly Phe Thr Phe Ser Ser Tyr
            20                  25                  30 agc atg aac tgg gtc cgc cag gct cca ggg aag ggc ctg gag tgg gtt      144
Ser Met Asn Trp Val Arg Gln Ala Pro Gly Lys Gly Leu Glu Trp Val
        35                  40                  45 tca tac att agt agt agt agt agt acc ata tac tac gca gac tct gtg      192
Ser Tyr Ile Ser Ser Ser Ser Ser Thr Ile Tyr Tyr Ala Asp Ser Val
    50                  55                  60 aag ggc cga ttc acc atc tcc aga gac aat gcc aag aac tca ctg tat      240
Lys Gly Arg Phe Thr Ile Ser Arg Asp Asn Ala Lys Asn Ser Leu Tyr
65                  70                  75                  80 ctg caa atg aac agc ctg aga gac gag gac acg gcc gtg tat tac tgt      288
Leu Gln Met Asn Ser Leu Arg Asp Glu Asp Thr Ala Val Tyr Tyr Cys
                85                  90                  95 gca aag gag act tgg tgg cag tcc ttt gac tac tgg ggc cag ggc acc      336
Ala Lys Glu Thr Trp Trp Gln Ser Phe Asp Tyr Trp Gly Gln Gly Thr
            100                 105                 110 ctg gtg acc gtc tcc agc                                              354
Leu Val Thr Val Ser Ser
        115
```

<210> SEQ ID NO 10
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chemically synthesized - Variable region of
      heavy chain of 02-114

<400> SEQUENCE: 10

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
```

```
                    85                  90                  95
Ala Lys Glu Thr Trp Trp Gln Ser Phe Asp Tyr Trp Gly Gln Gly Thr
                100                 105                 110

Leu Val Thr Val Ser Ser
        115

<210> SEQ ID NO 11
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Chemically synthesized - Variable region of
      heavy chain of 02-115
<220> FEATURE:
<221> NAME/KEY: CDS
<222> LOCATION: (1)..(354)

<400> SEQUENCE: 11 cag gtg cag ctg gtg cag tct ggg gct gag gcg aag aag cct ggg gcc        48
Gln Val Gln Leu Val Gln Ser Gly Ala Glu Ala Lys Lys Pro Gly Ala
1               5                   10                  15 tca gtg aag gtc tcc tgc aag gct tct gga tac acc ttc acc ggc tac        96
Ser Val Lys Val Ser Cys Lys Ala Ser Gly Tyr Thr Phe Thr Gly Tyr
            20                  25                  30 tat atg cac tgg gtg cga cag gcc cct gga caa ggg ctt gag tgg atg       144
Tyr Met His Trp Val Arg Gln Ala Pro Gly Gln Gly Leu Glu Trp Met
        35                  40                  45 gga tgg atc agc gct tac aat ggt aac aca aac tat gca cag aag ctc       192
Gly Trp Ile Ser Ala Tyr Asn Gly Asn Thr Asn Tyr Ala Gln Lys Leu
    50                  55                  60 cag ggc aga gtc acc atg acc aca gac aca tcc acg agc aca gcc tac       240
Gln Gly Arg Val Thr Met Thr Thr Asp Thr Ser Thr Ser Thr Ala Tyr
65                  70                  75                  80 atg gag ctg agg agc ctg aga tct gac gac acg gcc gtg tat tac tgt       288
Met Glu Leu Arg Ser Leu Arg Ser Asp Asp Thr Ala Val Tyr Tyr Cys
                85                  90                  95 gca agg tcg cag atg ccg agt tac ttt gac tac tgg ggc cag ggc acc       336
Ala Arg Ser Gln Met Pro Ser Tyr Phe Asp Tyr Trp Gly Gln Gly Thr
                100                 105                 110 ctg gtg acc gtc tcc agc                                               354
Leu Val Thr Val Ser Ser
        115

<210> SEQ ID NO 12
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chemically synthesized - Variable region of
      heavy chain of 02-115

<400> SEQUENCE: 12

Gln Val Gln Leu Val Gln Ser Gly Ala Glu Ala Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45
```

```
Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Gln Met Pro Ser Tyr Phe Asp Tyr Trp Gly Gln Gly Thr
            100                 105                 110

Leu Val Thr Val Ser Ser
            115

<210> SEQ ID NO 13
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Chemically synthesized - Variable region of
      heavy chain of 02-116
<220> FEATURE:
<221> NAME/KEY: CDS
<222> LOCATION: (1)..(354)

<400> SEQUENCE: 13 gag gtg cag ctg gtg gag tct ggg gga ggc ttg gta cag cct ggg ggg        48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttt agc agc tat        96
Ser Leu Arg Leu Ser Cys Ala Ala Ser Gly Phe Thr Phe Ser Ser Tyr
                20                  25                  30 gcc atg agc tgg gtc cgc cag gct cca ggg aag ggg ctg gag tgg gtc       144
Ala Met Ser Trp Val Arg Gln Ala Pro Gly Lys Gly Leu Glu Trp Val
            35                  40                  45 tca gct att agt ggt agt ggt ggt agc aca tac tac gca gac tcc gtg       192
Ser Ala Ile Ser Gly Ser Gly Gly Ser Thr Tyr Tyr Ala Asp Ser Val
        50                  55                  60 aag ggc cgg ttc acc atc tcc aga gac aat tcc aag aac acg ctg tat       240
Lys Gly Arg Phe Thr Ile Ser Arg Asp Asn Ser Lys Asn Thr Leu Tyr
65                  70                  75                  80 ctg caa atg aac agc cta aga gcc gag gac acg gcc gtg tat tac tgt       288
Leu Gln Met Asn Ser Leu Arg Ala Glu Asp Thr Ala Val Tyr Tyr Cys
                85                  90                  95 gca aag gac gct ctt tgg ctg tct ttt gac tac tgg ggc cag ggc acc       336
Ala Lys Asp Ala Leu Trp Leu Ser Phe Asp Tyr Trp Gly Gln Gly Thr
            100                 105                 110 ctg gtg acc gtc tcc agc                                                354
Leu Val Thr Val Ser Ser
            115

<210> SEQ ID NO 14
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chemically synthesized - Variable region of
      heavy chain of 02-116

<400> SEQUENCE: 14
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ala Leu Trp Leu Ala Phe Asp Tyr Trp Gly Gln Gly Thr
            100                 105                 110

Leu Val Thr Val Ser Ser
            115
```

<210> SEQ ID NO 15
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Chemically synthesized - Variable region of
      heavy chain of 02-117
<220> FEATURE:
<221> NAME/KEY: CDS
<222> LOCATION: (1)..(351)

<400> SEQUENCE: 15

```
gag gtg cag ctg gtg gag tct ggg gga ggc ttg gta cat cct ggg ggg         48
Glu Val Gln Leu Val Glu Ser Gly Gly Gly Leu Val His Pro Gly Gly
1               5                   10                  15 tcc ctg aga ctc tcc tgt gca ggc tct gga ttc acc ttc agt agc tat         96
Ser Leu Arg Leu Ser Cys Ala Gly Ser Gly Phe Thr Phe Ser Ser Tyr
            20                  25                  30 gct atg cac tgg gtt cgc cag gct cca gga aaa ggt ctg gag tgg gta        144
Ala Met His Trp Val Arg Gln Ala Pro Gly Lys Gly Leu Glu Trp Val
        35                  40                  45 tca gct att ggt act ggt ggt ggc aca tac tat gca gac tcc gtg aag        192
Ser Ala Ile Gly Thr Gly Gly Gly Thr Tyr Tyr Ala Asp Ser Val Lys
50                  55                  60 ggc cga ttc acc atc tcc aga gac aat gcc aag aac tcc ttg tat ctt        240
Gly Arg Phe Thr Ile Ser Arg Asp Asn Ala Lys Asn Ser Leu Tyr Leu
65                  70                  75                  80 caa atg aac agc ctg aga gcc gag gac acg gcc gtg tat tac tgt gca        288
Gln Met Asn Ser Leu Arg Ala Glu Asp Thr Ala Val Tyr Tyr Cys Ala
                85                  90                  95 agg tct acg cct tgg ttt tcc ttt gac tac tgg ggc cag ggc acc ctg        336
Arg Ser Thr Pro Trp Phe Ser Phe Asp Tyr Trp Gly Gln Gly Thr Leu
            100                 105                 110 gtg acc gtc tcc agc                                                    351
Val Thr Val Ser Ser
            115
```

<210> SEQ ID NO 16
<211> LENGTH: 117
<212> TYPE: PRT
<213> ORGANISM: Artificial Sequence
<220> FEATURE:

<223> OTHER INFORMATION: Description of Artificial Sequence: Synthetic
polypeptide
<220> FEATURE:
<223> OTHER INFORMATION: Chemically synthesized - Variable region of
heavy chain of 02-117

<400> SEQUENCE: 16

```
Glu Val Gln Leu Val Glu Ser Gly Gly Gly Leu Val His Pro Gly Gly
1               5                   10                  15

Ser Leu Arg Leu Ser Cys Ala Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Gly Thr Gly Gly Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
            85                  90                  95

Arg Ser Thr Pro Trp Phe Ser Phe Asp Tyr Trp Gly Gln Gly Thr Leu
            100                 105                 110

Val Thr Val Ser Ser
        115
```

<210> SEQ ID NO 17
<211> LENGTH: 351
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Chemically synthesized - Variable region of
heavy chain of 02-118
<220> FEATURE:
<221> NAME/KEY: CDS
<222> LOCATION: (1)..(351)

<400> SEQUENCE: 17

```
gag gtg cag ctg gtg gag tct ggg gga ggc ttg gta cat cct ggg ggg     48
Glu Val Gln Leu Val Glu Ser Gly Gly Gly Leu Val His Pro Gly Gly
1               5                   10                  15 tcc ctg aga ctc tcc tgt gca ggc tct gga ttc acc ttc agt agc tat     96
Ser Leu Arg Leu Ser Cys Ala Gly Ser Gly Phe Thr Phe Ser Ser Tyr
            20                  25                  30 gct atg cac tgg gtt cgc cag gct cca gga aaa ggt ctg gag tgg gta    144
Ala Met His Trp Val Arg Gln Ala Pro Gly Lys Gly Leu Glu Trp Val
        35                  40                  45 tca gct att agt act ggt ggt ggc aca tac tat gca gac tcc gtg aag    192
Ser Ala Ile Ser Thr Gly Gly Gly Thr Tyr Tyr Ala Asp Ser Val Lys
    50                  55                  60 ggc cga ttc acc atc tcc aga gac aat gcc aag aac tcc ttg tat ctt    240
Gly Arg Phe Thr Ile Ser Arg Asp Asn Ala Lys Asn Ser Leu Tyr Leu
65                  70                  75                  80 caa atg aac agc ctg aga gcc gag gac acg gcc gtg tat tac tgt gca    288
Gln Met Asn Ser Leu Arg Ala Glu Asp Thr Ala Val Tyr Tyr Cys Ala
            85                  90                  95 agg agt gct tgg tgg ctg tcc ttt gac tcc tgg ggc cag ggc acc ctg    336
Arg Ser Ala Trp Trp Leu Ser Phe Asp Ser Trp Gly Gln Gly Thr Leu
            100                 105                 110 gtg acc gtc tcc agc                                                351
Val Thr Val Ser Ser
```

<210> SEQ ID NO 18
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Chemically synthesized - Variable region of
heavy chain of 02-118

<400> SEQUENCE: 18

```
Glu Val Gln Leu Val Glu Ser Gly Gly Gly Leu Val His Pro Gly Gly
1               5                   10                  15

Ser Leu Arg Leu Ser Cys Ala Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Ser Thr Gly Gly Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Ser Ala Trp Trp Leu Ser Phe Asp Ser Trp Gly Gln Gly Thr Leu
            100                 105                 110

Val Thr Val Ser Ser
        115
```

<210> SEQ ID NO 19
<211> LENGTH: 330
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Chemically synthesized - Variable region of
light chain of 02-113, 02-114, 02-116, 02-117 and 02-118
<220> FEATURE:
<221> NAME/KEY: CDS
<222> LOCATION: (1)..(330)

<400> SEQUENCE: 19

```
gac att cag atg acc cag tct cca tcc tcc ctg tct gca tct gta gga       48
Asp Ile Gln Met Thr Gln Ser Pro Ser Ser Leu Ser Ala Ser Val Gly
1               5                   10                  15 gac aga gtc acc atc act tgc cgg gca agt cag agc att agc agc tac       96
Asp Arg Val Thr Ile Thr Cys Arg Ala Ser Gln Ser Ile Ser Ser Tyr
            20                  25                  30 tta aat tgg tat cag cag aaa cca ggg aaa gcc cct aag ctc ctg atc     144
Leu Asn Trp Tyr Gln Gln Lys Pro Gly Lys Ala Pro Lys Leu Leu Ile
        35                  40                  45 tat gct gca tcc agt ttg caa agt ggg gtc cca tca agg ttc agt ggc     192
Tyr Ala Ala Ser Ser Leu Gln Ser Gly Val Pro Ser Arg Phe Ser Gly
    50                  55                  60 agt gga tct ggg aca gat ttc act ctc acc atc agc agt ctg caa cct     240
Ser Gly Ser Gly Thr Asp Phe Thr Leu Thr Ile Ser Ser Leu Gln Pro
65                  70                  75                  80 gaa gat ttt gca act tac tac tgt caa cag agt tac agt acc cct cca     288
Glu Asp Phe Ala Thr Tyr Tyr Cys Gln Gln Ser Tyr Ser Thr Pro Pro
```

```
                     85                  90                  95
acg ttc ggc caa ggg acc aag gtg gag atc aaa cgg acc gtg              330
Thr Phe Gly Gln Gly Thr Lys Val Glu Ile Lys Arg Thr Val
                100                 105                 110

<210> SEQ ID NO 20
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chemically synthesized - Variable region of
      light chain of 02-113, 02-114, 02-116, 02-117 and 02-118

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys Arg Thr Val
            100                 105                 110

<210> SEQ ID NO 21
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Chemically synthesized - Variable region of
      light chain of 02-115
<220> FEATURE:
<221> NAME/KEY: CDS
<222> LOCATION: (1)..(354)

<400> SEQUENCE: 21 tcc tcc gag ctg acc cag gac cct gct gtg tct gtg gcc ttg gga cag       48
Ser Ser Glu Leu Thr Gln Asp Pro Ala Val Ser Val Ala Leu Gly Gln
1               5                   10                  15 aca gtc agg atc aca tgc caa gga gac agc ctc aga agc tat tat gca       96
Thr Val Arg Ile Thr Cys Gln Gly Asp Ser Leu Arg Ser Tyr Tyr Ala
            20                  25                  30 agc tgg tac cag cag aag cca gga cag gcc cct gta ctt gtc atc tat      144
Ser Trp Tyr Gln Gln Lys Pro Gly Gln Ala Pro Val Leu Val Ile Tyr
        35                  40                  45 ggt aaa aac aac cgg ccc tca ggg atc cca gac cga ttc tct ggc tcc      192
Gly Lys Asn Asn Arg Pro Ser Gly Ile Pro Asp Arg Phe Ser Gly Ser
    50                  55                  60 agc tca gga aac aca gct tcc ttg acc atc act ggg gct cag gcg gaa      240
Ser Ser Gly Asn Thr Ala Ser Leu Thr Ile Thr Gly Ala Gln Ala Glu
65                  70                  75                  80 gat gag gct gac tat tac tgt aac tcc cgg gac agc agt ggt aac cat      288
Asp Glu Ala Asp Tyr Tyr Cys Asn Ser Arg Asp Ser Ser Gly Asn His
```

```
Asp Glu Ala Asp Tyr Tyr Cys Asn Ser Arg Asp Ser Gly Asn His
            85                  90                  95 gtg gta ttc ggc gga ggg acc aag ctg acc gtc cta ggt gag tcg cgg    336
Val Val Phe Gly Gly Gly Thr Lys Leu Thr Val Leu Gly Glu Ser Arg
            100                 105                 110 ccg caa gct tac cgt gct                                             354
Pro Gln Ala Tyr Arg Ala
        115
```

<210> SEQ ID NO 22
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chemically synthesized - Variable region of
      light chain of 02-115

<400> SEQUENCE: 22

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Gly Asn His
                85                  90                  95

Val Val Phe Gly Gly Gly Thr Lys Leu Thr Val Leu Gly Glu Ser Arg
            100                 105                 110

Pro Gln Ala Tyr Arg Ala
        115
```

<210> SEQ ID NO 23
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized - Primer M13rev

<400> SEQUENCE: 23
aacagctatg accatg                                                   16

<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized - Primer fdSeq

<400> SEQUENCE: 24
gaattttctg tatgagg                                                  17

<210> SEQ ID NO 25
<211> LENGTH: 720
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Chemically synthesized - Sequence of scFv SC02-113
<220> FEATURE:
<221> NAME/KEY: CDS
<222> LOCATION: (1)..(720)

<400> SEQUENCE: 25

| cag | gtg | cag | ctg | cag | gag | tcg | ggc | gca | gga | ctg | ttg | aag | cct | tcg | gag | 48 |
| Gln | Val | Gln | Leu | Gln | Glu | Ser | Gly | Ala | Gly | Leu | Leu | Lys | Pro | Ser | Glu | |
| 1 | | | | 5 | | | | | 10 | | | | | 15 | | |

| acc | ctg | tcc | ctc | acc | tgc | gct | gtc | tat | ggt | ggg | tct | ttc | agt | ggc | tac | 96 |
| Thr | Leu | Ser | Leu | Thr | Cys | Ala | Val | Tyr | Gly | Gly | Ser | Phe | Ser | Gly | Tyr | |
| | | | 20 | | | | | 25 | | | | | 30 | | | |

| tac | tgg | agc | tgg | atc | cgg | cag | ccc | cca | ggg | aag | gga | ctg | gag | tgg | att | 144 |
| Tyr | Trp | Ser | Trp | Ile | Arg | Gln | Pro | Pro | Gly | Lys | Gly | Leu | Glu | Trp | Ile | |
| | | 35 | | | | | 40 | | | | | 45 | | | | |

| ggg | tat | atc | tat | tac | agt | ggg | agc | acc | aac | tac | aac | ccc | tcc | ctc | aag | 192 |
| Gly | Tyr | Ile | Tyr | Tyr | Ser | Gly | Ser | Thr | Asn | Tyr | Asn | Pro | Ser | Leu | Lys | |
| 50 | | | | | 55 | | | | | 60 | | | | | | |

| agt | cga | gtc | acc | ata | tca | gta | gac | acg | tcc | aag | aac | cag | ttc | tcc | ctg | 240 |
| Ser | Arg | Val | Thr | Ile | Ser | Val | Asp | Thr | Ser | Lys | Asn | Gln | Phe | Ser | Leu | |
| 65 | | | | 70 | | | | | 75 | | | | | 80 | | |

| aag | ctg | agc | tct | gtg | acc | gct | gcg | gac | acg | gcc | gtg | tat | tac | tgt | gca | 288 |
| Lys | Leu | Ser | Ser | Val | Thr | Ala | Ala | Asp | Thr | Ala | Val | Tyr | Tyr | Cys | Ala | |
| | | | 85 | | | | | 90 | | | | | 95 | | | |

| aag | gcc | cct | tat | atg | atg | tat | ttt | gac | tcc | tgg | ggc | caa | ggt | acc | ctg | 336 |
| Lys | Ala | Pro | Tyr | Met | Met | Tyr | Phe | Asp | Ser | Trp | Gly | Gln | Gly | Thr | Leu | |
| | | 100 | | | | | 105 | | | | | 110 | | | | |

| gtc | acc | gtc | tcg | agt | ggt | gga | ggc | ggt | tca | ggc | gga | ggt | ggc | tct | ggc | 384 |
| Val | Thr | Val | Ser | Ser | Gly | Gly | Gly | Gly | Ser | Gly | Gly | Gly | Gly | Ser | Gly | |
| | | 115 | | | | | 120 | | | | | 125 | | | | |

| ggt | ggc | gga | tcg | gaa | att | gag | ctc | acc | cag | tct | cca | tcc | tcc | ctg | tct | 432 |
| Gly | Gly | Gly | Ser | Glu | Ile | Glu | Leu | Thr | Gln | Ser | Pro | Ser | Ser | Leu | Ser | |
| 130 | | | | | 135 | | | | | 140 | | | | | | |

| gca | tct | gta | gga | gac | aga | gtc | acc | atc | act | tgc | cgg | gca | agt | cag | agc | 480 |
| Ala | Ser | Val | Gly | Asp | Arg | Val | Thr | Ile | Thr | Cys | Arg | Ala | Ser | Gln | Ser | |
| 145 | | | | | 150 | | | | | 155 | | | | | 160 | |

| att | agc | agc | tac | tta | aat | tgg | tat | cag | cag | aaa | cca | ggg | aaa | gcc | cct | 528 |
| Ile | Ser | Ser | Tyr | Leu | Asn | Trp | Tyr | Gln | Gln | Lys | Pro | Gly | Lys | Ala | Pro | |
| | | | 165 | | | | | 170 | | | | | 175 | | | |

| aag | ctc | ctg | atc | tat | gct | gca | tcc | agt | ttg | caa | agt | ggg | gtc | cca | tca | 576 |
| Lys | Leu | Leu | Ile | Tyr | Ala | Ala | Ser | Ser | Leu | Gln | Ser | Gly | Val | Pro | Ser | |
| | | 180 | | | | | 185 | | | | | 190 | | | | |

| agg | ttc | agt | ggc | agt | gga | tct | ggg | aca | gat | ttc | act | ctc | acc | atc | agc | 624 |
| Arg | Phe | Ser | Gly | Ser | Gly | Ser | Gly | Thr | Asp | Phe | Thr | Leu | Thr | Ile | Ser | |
| | | 195 | | | | | 200 | | | | | 205 | | | | |

| agt | ctg | caa | cct | gaa | gat | ttt | gca | act | tac | tac | tgt | caa | cag | agt | tac | 672 |
| Ser | Leu | Gln | Pro | Glu | Asp | Phe | Ala | Thr | Tyr | Tyr | Cys | Gln | Gln | Ser | Tyr | |
| | 210 | | | | | 215 | | | | | 220 | | | | | |

| agt | acc | cct | cca | acg | ttc | ggc | caa | ggg | acc | aag | gtg | gag | atc | aaa | cgt | 720 |
| Ser | Thr | Pro | Pro | Thr | Phe | Gly | Gln | Gly | Thr | Lys | Val | Glu | Ile | Lys | Arg | |
| 225 | | | | | 230 | | | | | 235 | | | | | 240 | |

<210> SEQ ID NO 26

<211> LENGTH: 240
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Chemically synthesized - Sequence of scFv SC02-113

<400> SEQUENCE: 26

```
Gln Val Gln Leu Gln Glu Ser Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Lys Ala Pro Tyr Met Met Tyr Phe Asp Ser Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Glu Ile Glu Leu Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Ala Ala Ser Ser Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ser Tyr
    210                 215                 220

Ser Thr Pro Pro Thr Phe Gly Gln Gly Thr Lys Val Glu Ile Lys Arg
225                 230                 235                 240
```

<210> SEQ ID NO 27
<211> LENGTH: 723
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Chemically synthesized - Sequence of scFv SC02-114
<220> FEATURE:
<221> NAME/KEY: CDS
<222> LOCATION: (1)..(723)

<400> SEQUENCE: 27

```
gag gtg cag ctg gtg gag tct ggg gga ggc ttg gta cag cct ggg ggg      48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttc agt agc tat      96
```

```
                                                                   -continued Ser Leu Arg Leu Ser Cys Ala Ala Ser Gly Phe Thr Phe Ser Ser Tyr
            20                  25                  30 agc atg aac tgg gtc cgc cag gct cca ggg aag ggg ctg gag tgg gtt      144
Ser Met Asn Trp Val Arg Gln Ala Pro Gly Lys Gly Leu Glu Trp Val
        35                  40                  45 tca tac att agt agt agt agt acc ata tac tac gca gac tct gtg          192
Ser Tyr Ile Ser Ser Ser Ser Thr Ile Tyr Tyr Ala Asp Ser Val
    50                  55                  60 aag ggc cga ttc acc atc tcc aga gac aat gcc aag aac tca ctg tat      240
Lys Gly Arg Phe Thr Ile Ser Arg Asp Asn Ala Lys Asn Ser Leu Tyr
65                  70                  75                  80 ctg caa atg aac agc ctg aga gac gag gac acg gcc gtg tat tac tgt      288
Leu Gln Met Asn Ser Leu Arg Asp Glu Asp Thr Ala Val Tyr Tyr Cys
                85                  90                  95 gca aag gag act tgg tgg cag tcc ttt gac tac tgg ggc caa ggt acc      336
Ala Lys Glu Thr Trp Trp Gln Ser Phe Asp Tyr Trp Gly Gln Gly Thr
            100                 105                 110 ctg gtc acc gtc tcg agt ggt gga ggc ggt tca ggc gga ggt ggc tct      384
Leu Val Thr Val Ser Ser Gly Gly Gly Gly Ser Gly Gly Gly Gly Ser
        115                 120                 125 ggc ggt ggc gga tcg gaa att gag ctc acc cag tct cca tcc tcc ctg      432
Gly Gly Gly Gly Ser Glu Ile Glu Leu Thr Gln Ser Pro Ser Ser Leu
    130                 135                 140 tct gca tct gta gga gac aga gtc acc atc act tgc cgg gca agt cag      480
Ser Ala Ser Val Gly Asp Arg Val Thr Ile Thr Cys Arg Ala Ser Gln
145                 150                 155                 160 agc att agc agc tac tta aat tgg tat cag cag aaa cca ggg aaa gcc      528
Ser Ile Ser Ser Tyr Leu Asn Trp Tyr Gln Gln Lys Pro Gly Lys Ala
                165                 170                 175 cct aag ctc ctg atc tat gct gca tcc agt ttg caa agt ggg gtc cca      576
Pro Lys Leu Leu Ile Tyr Ala Ala Ser Ser Leu Gln Ser Gly Val Pro
            180                 185                 190 tca agg ttc agt ggc agt gga tct ggg aca gat ttc act ctc acc atc      624
Ser Arg Phe Ser Gly Ser Gly Ser Gly Thr Asp Phe Thr Leu Thr Ile
        195                 200                 205 agc agt ctg caa cct gaa gat ttt gca act tac tac tgt caa cag agt      672
Ser Ser Leu Gln Pro Glu Asp Phe Ala Thr Tyr Tyr Cys Gln Gln Ser
    210                 215                 220 tac agt acc cct cca acg ttc ggc caa ggg acc aag gtg gag atc aaa      720
Tyr Ser Thr Pro Pro Thr Phe Gly Gln Gly Thr Lys Val Glu Ile Lys
225                 230                 235                 240 cgt                                                                  723
Arg

<210> SEQ ID NO 28
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chemically synthesized - Sequence of scFv
      SC02-114

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
```

```
                35                  40                  45
Ser Tyr Ile Ser Ser Ser Ser Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                 85                  90                  95

Ala Lys Glu Thr Trp Trp Gln Ser Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Ser Glu Ile Glu Leu Thr Gln Ser Pro Ser Ser Leu
    130                 135                 140

Ser Ala Ser Val Gly Asp Arg Val Thr Ile Thr Cys Arg Ala Ser Gln
145                 150                 155                 160

Ser Ile Ser Ser Tyr Leu Asn Trp Tyr Gln Gln Lys Pro Gly Lys Ala
                165                 170                 175

Pro Lys Leu Leu Ile Tyr Ala Ala Ser Ser Leu Gln Ser Gly Val Pro
            180                 185                 190

Ser Arg Phe Ser Gly Ser Gly Ser Gly Thr Asp Phe Thr Leu Thr Ile
        195                 200                 205

Ser Ser Leu Gln Pro Glu Asp Phe Ala Thr Tyr Tyr Cys Gln Gln Ser
    210                 215                 220

Tyr Ser Thr Pro Pro Thr Phe Gly Gln Gly Thr Lys Val Glu Ile Lys
225                 230                 235                 240

Arg

<210> SEQ ID NO 29
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Chemically synthesized - Sequence of scFv
      SC02-115

<400> SEQUENCE: 29
caggtgcagc tggtgcagtc tggggctgag gcgaagaagc tggggcctc  agtgaaggtc     60 tcctgcaagg cttctggata caccttcacc ggctactata tgcactgggt gcgacaggcc    120
cctggacaag gcttgagtg gatgggatgg atcagcgctt acaatggtaa cacaaactat    180
gcacagaagc tccagggcag agtcaccatg accacagaca catccacgag cacagcctac    240
atggagctga ggagcctgag atctgacgac acggccgtgt attactgtgc aaggtcgtag    300
atgccgagtt actttgacta ctgggggccaa ggtaccctgg tcaccgtctc gagaggtgga    360
ggcggttcag gcggaggtgg ctctggcggt ggcggatcgt ctgagctgac tcaggaccct    420
gctgtgtctg tggccttggg acagacagtc aggatcacat gccaaggaga cagcctcaga    480
agctattatg caagctggta ccagcagaag ccaggacagg cccctgtact tgtcatctat    540
ggtaaaaaca accggccctc agggatccca gaccgattct ctggctccag ctcaggaaac    600
acagcttcct tgaccatcac tggggctcag gcggaagatg aggctgacta ttactgtaac    660
tcccgggaca gcagtggtaa ccatgtggta ttcggcggag ggaccaagct gaccgtccta    720
ggt                                                                 723
```

<210> SEQ ID NO 30
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chemically synthesized - Sequence of scFv
      SC02-115

<400> SEQUENCE: 30

Gln Val Gln Leu Val Gln Ser Gly Ala Glu Ala Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Gln Met Pro Ser Tyr Phe Asp Tyr Trp Gly Gln Gly Thr
            100                 105                 110

Leu Val Thr Val Ser Arg Gly Gly Gly Gly Ser Gly Gly Gly Gly Ser
        115                 120                 125

Gly Gly Gly Gly Ser Ser Glu Leu Thr Gln Asp Pro Ala Val Ser Val
    130                 135                 140

Ala Leu Gly Gln Thr Val Arg Ile Thr Cys Gln Gly Asp Ser Leu Arg
145                 150                 155                 160

Ser Tyr Tyr Ala Ser Trp Tyr Gln Gln Lys Pro Gly Gln Ala Pro Val
                165                 170                 175

Leu Val Ile Tyr Gly Lys Asn Asn Arg Pro Ser Gly Ile Pro Asp Arg
            180                 185                 190

Phe Ser Gly Ser Ser Ser Gly Asn Thr Ala Ser Leu Thr Ile Thr Gly
        195                 200                 205

Ala Gln Ala Glu Asp Glu Ala Asp Tyr Tyr Cys Asn Ser Arg Asp Ser
    210                 215                 220

Ser Gly Asn His Val Val Phe Gly Gly Gly Thr Lys Leu Thr Val Leu
225                 230                 235                 240

Gly

<210> SEQ ID NO 31
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Chemically synthesized - Sequence of scFv
      SC02-116
<220> FEATURE:
<221> NAME/KEY: CDS
<222> LOCATION: (1)..(723)

<400> SEQUENCE: 31

```
gag gtg cag ctg gtg gag tct ggg gga ggc ttg gta cag cct ggg ggg      48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttt agc agc tat      96
Ser Leu Arg Leu Ser Cys Ala Ala Ser Gly Phe Thr Phe Ser Ser Tyr
            20                  25                  30 gcc atg agc tgg gtc cgc cag gct cca ggg aag ggg ctg gag tgg gtc     144
Ala Met Ser Trp Val Arg Gln Ala Pro Gly Lys Gly Leu Glu Trp Val
        35                  40                  45 tca gct att agt ggt agt ggt ggt agc aca tac tac gca gac tcc gtg     192
Ser Ala Ile Ser Gly Ser Gly Gly Ser Thr Tyr Tyr Ala Asp Ser Val
    50                  55                  60 aag ggc cgg ttc acc atc tcc aga gac aat tcc aag aac acg ctg tat     240
Lys Gly Arg Phe Thr Ile Ser Arg Asp Asn Ser Lys Asn Thr Leu Tyr
65                  70                  75                  80 ctg caa atg aac agc cta aga gcc gag gac acg gcc gtg tat tac tgt     288
Leu Gln Met Asn Ser Leu Arg Ala Glu Asp Thr Ala Val Tyr Tyr Cys
                85                  90                  95 gca aag gac gct ctt tgg ctg gct ttt gac tac tgg ggc caa ggt acc     336
Ala Lys Asp Ala Leu Trp Leu Ala Phe Asp Tyr Trp Gly Gln Gly Thr
            100                 105                 110 ctg gtc acc gtc tcg agt ggt gga ggc ggt tca ggc gga ggt ggc tct     384
Leu Val Thr Val Ser Ser Gly Gly Gly Gly Ser Gly Gly Gly Gly Ser
        115                 120                 125 ggc ggt ggc gga tcg gaa att gag ctc acc cag tct cca tcc tcc ctg     432
Gly Gly Gly Gly Ser Glu Ile Glu Leu Thr Gln Ser Pro Ser Ser Leu
    130                 135                 140 tct gca tct gta gga gac aga gtc acc atc act tgc cgg gca agt cag     480
Ser Ala Ser Val Gly Asp Arg Val Thr Ile Thr Cys Arg Ala Ser Gln
145                 150                 155                 160 agc att agc agc tat tta aat tgg tat cag cag aaa cca ggg aaa gcc     528
Ser Ile Ser Ser Tyr Leu Asn Trp Tyr Gln Gln Lys Pro Gly Lys Ala
                165                 170                 175 cct aag ctc ctg atc tat gct gca tcc agt ttg caa agt ggg gtc cca     576
Pro Lys Leu Leu Ile Tyr Ala Ala Ser Ser Leu Gln Ser Gly Val Pro
            180                 185                 190 tca agg ttc agt ggc agt gga tct ggg aca gat ttc act ctc acc atc     624
Ser Arg Phe Ser Gly Ser Gly Ser Gly Thr Asp Phe Thr Leu Thr Ile
        195                 200                 205 agc agt ctg caa cct gaa gat ttt gca act tac tac tgt gct cag agg     672
Ser Ser Leu Gln Pro Glu Asp Phe Ala Thr Tyr Tyr Cys Ala Gln Arg
    210                 215                 220 agt tat ccg cct cct aag ttc ggc caa ggg acc aag gtg gat atc aaa     720
Ser Tyr Pro Pro Pro Lys Phe Gly Gln Gly Thr Lys Val Asp Ile Lys
225                 230                 235                 240 cgt                                                                 723
Arg

<210> SEQ ID NO 32
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chemically synthesized - Sequence of scFv
      SC02-116

<400> SEQUENCE: 32

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ala Leu Trp Leu Ala Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Glu Ile Glu Leu Thr Gln Ser Pro Ser Ser Leu
130                 135                 140

Ser Ala Ser Val Gly Asp Arg Val Thr Ile Thr Cys Arg Ala Ser Gln
145                 150                 155                 160

Ser Ile Ser Ser Tyr Leu Asn Trp Tyr Gln Gln Lys Pro Gly Lys Ala
                165                 170                 175

Pro Lys Leu Leu Ile Tyr Ala Ala Ser Ser Leu Gln Ser Gly Val Pro
            180                 185                 190

Ser Arg Phe Ser Gly Ser Gly Ser Gly Thr Asp Phe Thr Leu Thr Ile
        195                 200                 205

Ser Ser Leu Gln Pro Glu Asp Phe Ala Thr Tyr Tyr Cys Ala Gln Arg
210                 215                 220

Ser Tyr Pro Pro Lys Phe Gly Gln Gly Thr Lys Val Asp Ile Lys
225                 230                 235                 240

Arg

<210> SEQ ID NO 33
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Chemically synthesized - Sequence of scFv
      SC02-117
<220> FEATURE:
<221> NAME/KEY: CDS
<222> LOCATION: (1)..(720)

<400> SEQUENCE: 33 gag gtg cag ctg gtg gag tct ggg gga ggc ttg gta cat cct ggg ggg        48
Glu Val Gln Leu Val Glu Ser Gly Gly Gly Leu Val His Pro Gly Gly
1               5                   10                  15 tcc ctg aga ctc tcc tgt gca ggc tct gga ttc acc ttc agt agc tat        96
Ser Leu Arg Leu Ser Cys Ala Gly Ser Gly Phe Thr Phe Ser Ser Tyr
            20                  25                  30 gct atg cac tgg gtt cgc cag gct cca gga aaa ggt ctg gag tgg gta       144
Ala Met His Trp Val Arg Gln Ala Pro Gly Lys Gly Leu Glu Trp Val
        35                  40                  45 tca gct att ggt act ggt ggt ggc aca tac tat gca gac tcc gtg aag       192
Ser Ala Ile Gly Thr Gly Gly Gly Thr Tyr Tyr Ala Asp Ser Val Lys
50                  55                  60 ggc cga ttc acc atc tcc aga gac aat gcc aag aac tcc ttg tat ctt       240
```

```
                                                                                        -continued Gly Arg Phe Thr Ile Ser Arg Asp Asn Ala Lys Asn Ser Leu Tyr Leu
 65                  70                  75                  80 caa atg aac agc ctg aga gcc gag gac acg gcc gtg tat tac tgt gca       288
Gln Met Asn Ser Leu Arg Ala Glu Asp Thr Ala Val Tyr Tyr Cys Ala
                 85                  90                  95 agg tct acg cct tgg ttt tcc ttt gac tac tgg ggc caa ggt acc ctg       336
Arg Ser Thr Pro Trp Phe Ser Phe Asp Tyr Trp Gly Gln Gly Thr Leu
            100                 105                 110 gtc acc gtc tcg agt ggt gga ggc ggt tca ggc gga ggt ggc tct ggc       384
Val Thr Val Ser Ser Gly Gly Gly Gly Ser Gly Gly Gly Gly Ser Gly
        115                 120                 125 ggt ggc gga tcg gaa att gag ctc acc cag tct cca tcc tcc ctg tct       432
Gly Gly Gly Ser Glu Ile Glu Leu Thr Gln Ser Pro Ser Ser Leu Ser
    130                 135                 140 gca tct gta gga gac aga gtc acc atc act tgc cgg gca agt cag agc       480
Ala Ser Val Gly Asp Arg Val Thr Ile Thr Cys Arg Ala Ser Gln Ser
145                 150                 155                 160 att agc agc tac tta aat tgg tat cag cag aaa cca ggg aaa gcc cct       528
Ile Ser Ser Tyr Leu Asn Trp Tyr Gln Gln Lys Pro Gly Lys Ala Pro
                165                 170                 175 aag ctc ctg atc tat gct gca tcc agt ttg caa agt ggg gtc cca tca       576
Lys Leu Leu Ile Tyr Ala Ala Ser Ser Leu Gln Ser Gly Val Pro Ser
            180                 185                 190 agg ttc agt ggc agt gga tct ggg aca gat ttc act ctc acc atc agc       624
Arg Phe Ser Gly Ser Gly Ser Gly Thr Asp Phe Thr Leu Thr Ile Ser
        195                 200                 205 agt ctg caa cct gaa gat ttt gca act tac tac tgt caa cag agt tac       672
Ser Leu Gln Pro Glu Asp Phe Ala Thr Tyr Tyr Cys Gln Gln Ser Tyr
    210                 215                 220 agt acc cct cca acg ttc ggc caa ggg acc aag gtg gag atc aaa cgt       720
Ser Thr Pro Pro Thr Phe Gly Gln Gly Thr Lys Val Glu Ile Lys Arg
225                 230                 235                 240
```

<210> SEQ ID NO 34
<211> LENGTH: 240
<212> TYPE: PRT
<213> ORGANISM: Artificial Sequence
<220> FEATURE:
<223> OTHER INFORMATION: Description of Artificial Sequence: Synthetic
       polypeptide
<220> FEATURE:
<223> OTHER INFORMATION: Chemically synthesized - Sequence of scFv
       SC02-117

<400> SEQUENCE: 34

```
Glu Val Gln Leu Val Glu Ser Gly Gly Gly Leu Val His Pro Gly Gly
 1               5                  10                  15

Ser Leu Arg Leu Ser Cys Ala Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Gly Thr Gly Gly Gly Thr Tyr Tyr Ala Asp Ser Val Lys
    50                  55                  60

Gly Arg Phe Thr Ile Ser Arg Asp Asn Ala Lys Asn Ser Leu Tyr Leu
 65                  70                  75                  80

Gln Met Asn Ser Leu Arg Ala Glu Asp Thr Ala Val Tyr Tyr Cys Ala
                 85                  90                  95

Arg Ser Thr Pro Trp Phe Ser Phe Asp Tyr Trp Gly Gln Gly Thr Leu
            100                 105                 110

Val Thr Val Ser Ser Gly Gly Gly Gly Ser Gly Gly Gly Gly Ser Gly
```

```
                115             120                 125
Gly Gly Gly Ser Glu Ile Glu Leu Thr Gln Ser Pro Ser Ser Leu Ser
        130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Ala Ala Ser Ser Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ser Tyr
    210                 215                 220

Ser Thr Pro Pro Thr Phe Gly Gln Gly Thr Lys Val Glu Ile Lys Arg
225                 230                 235                 240
```

<210> SEQ ID NO 35
<211> LENGTH: 720
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: Chemically synthesized - Sequence of scFv
    SC02-118

<400> SEQUENCE: 35

```
gaggtgcagc tggtggagtc tgggggaggc taggtacatc ctgggggtc cctgagactc     60 tcctgtgcag gctctggatt caccttcagt agctatgcta tgcactgggt cgccaggct    120 ccaggaaaag gtctggagtg ggtatcagct attagtactg gtggtggcac atactatgca   180
gactccgtga aggccgatt caccatctcc agagacaatg ccaagaactc cttgtatctt    240
caaatgaaca gcctgagagc cgaggacacg gccgtgtatt actgtgcaag gagtgcttgg   300
tggctgtcct ttgactcctg gggccaaggt accctggtca ccgtctcgag tggtggaggc   360
ggttcaggcg gaggtggctc tggcggtggc ggatcggaaa ttgagctcac ccagtctcca   420 tcctcctgt ctgcatctgt aggagacaga gtcaccatca cttgccgggc aagtcagagc    480
attagcagct acttaaattg gtatcagcag aaaccaggga agcccctaa gctcctgatc    540 tatgctgcat ccagtttgca aagtggggtc ccatcaaggt tcagtggcag tggatctggg   600
acagatttca ctctcaccat cagcagtctg caacctgaag attttgcaac ttactactgt   660
caacagagtt acagtacccc tccaacgttc ggccaaggga ccaaggtgga gatcaaacgt   720
```

<210> SEQ ID NO 36
<211> LENGTH: 240
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Chemically synthesized - Sequence of scFv
    SC02-118

<400> SEQUENCE: 36

```
Glu Val Gln Leu Val Glu Ser Gly Gly Gly Gln Val His Pro Gly Gly
1               5                   10                  15

Ser Leu Arg Leu Ser Cys Ala Gly Ser Gly Phe Thr Phe Ser Ser Tyr
```

```
            20                  25                  30
Ala Met His Trp Val Arg Gln Ala Pro Gly Lys Gly Leu Glu Trp Val
            35                  40                  45

Ser Ala Ile Ser Thr Gly Gly Thr Tyr Tyr Ala Asp Ser Val Lys
        50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Ser Ala Trp Trp Leu Ser Phe Asp Ser Trp Gly Gln Gly Thr Leu
                100                 105                 110

Val Thr Val Ser Ser Gly Gly Gly Gly Ser Gly Gly Gly Gly Ser Gly
            115                 120                 125

Gly Gly Gly Ser Glu Ile Glu Leu Thr Gln Ser Pro Ser Ser Leu Ser
        130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Ala Ala Ser Ser Leu Gln Ser Gly Val Pro Ser
                180                 185                 190

Arg Phe Ser Gly Ser Gly Ser Gly Thr Asp Phe Thr Leu Thr Ile Ser
                195                 200                 205

Ser Leu Gln Pro Glu Asp Phe Ala Thr Tyr Tyr Cys Gln Gln Ser Tyr
        210                 215                 220

Ser Thr Pro Pro Thr Phe Gly Gln Gly Thr Lys Val Glu Ile Lys Arg
225                 230                 235                 240

<210> SEQ ID NO 37
<211> LENGTH: 6778
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Chemically synthesized - pSyn-C03-HCgamma1

<400> SEQUENCE: 37
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgct aggtggtcaa tattggccat agccatatt      240 attcattggt tatatagcat aaatcaatat tggctattgg ccattgcata cgttgtatcc     300
atatcataat atgtacattt atattggctc atgtccaaca ttaccgccat gttgacattg     360
attattgact agttattaat agtaatcaat tacggggtca ttagttcata gcccatatat     420
ggagttccgc gttacataac ttacggtaaa tggcccgcct ggctgaccgc ccaacgaccc     480
ccgcccattg acgtcaataa tgacgtatgt tcccatagta acgccaatag ggactttcca     540
ttgacgtcaa tgggtggagt atttacggta aactgcccac ttggcagtac atcaagtgta     600
tcatatgcca gtacgccccc tattgacgtc aatgacggt aaatggcccg cctggcatta     660
tgcccagtac atgaccttat gggactttcc tacttggcag tacatctacg tattagtcat     720
cgctattacc atggtgatgc ggttttggca gtacatcaat gggcgtggat agcggtttga     780
```

```
ctcacgggga tttccaagtc tccaccccat tgacgtcaat gggagtttgt tttggcacca      840
aaatcaacgg actttccaa aatgtcgtaa caactccgcc ccattgacgc aaatgggcgg       900
taggcgtgta cggtgggagg tctatataag cagagctcgt ttagtgaacc gtcagatcgc      960
ctggagacgc catccacgct gttttgacct ccatagaaga caccgggacc gatccagcct     1020
ccgcggccgg gaacggtgca ttggaagctg gcctggatgg cctgactctc ttaggtagcc     1080
ttgcagaagt tggtcgtgag gcactgggca ggtaagtatc aaggttacaa gacaggttta     1140
aggagatcaa tagaaactgg gcttgtcgag acagagaaga ctcttgcgtt tctgataggc     1200
acctattggt cttactgaca tccactttgc ctttctctcc acaggtgtcc actcccagtt     1260
caattacagc tcgccaccat ggcctgcccc ggcttcctgt gggccctggt gatcagcacc     1320
tgcctggaat tcagcatgag cagcgctagc accaagggcc ccagcgtgtt cccctggcc     1380 cccagcagca agagcaccag cggcggcaca gccgccctgg gctgctggt gaaggactac      1440 ttccccgagc ccgtgaccgt gagctggaac agcggcgcct tgaccagcgg cgtgcacacc     1500
ttccccgccg tgctgcagag cagcggcctg tacagcctga gcagcgtggt gaccgtgccc     1560
agcagcagcc tgggcaccca gacctacatc tgcaacgtga accacaagcc cagcaacacc     1620
aaggtggaca aacgcgtgga gcccaagagc tgcgacaaga cccacacctg ccccccctgc     1680
cctgcccccg agctgctggg cggaccctcc gtgttcctgt tcccccccaa gcccaaggac     1740
accctcatga tcagccggac ccccgaggtg acctgcgtgg tggtggacgt gagccacgag     1800
gaccccgagg tgaagttcaa ctggtacgtg gacggcgtgg aggtgcacaa cgccaagacc     1860
aagccccggg aggagcagta caacagcacc taccgggtgg tgagcgtgct caccgtgctg     1920
caccaggact ggctgaacgg caaggagtac aagtgcaagg tgagcaacaa ggccctgcct     1980
gcccccatcg agaagaccat cagcaaggcc aagggccagc ccgggagcc ccaggtgtac      2040 accctgcccc ccagccggga ggagatgacc aagaaccagg tgtccctcac ctgtctggtg     2100
aagggcttct accccagcga catcgccgtg gagtgggaga gcaacggcca gcccgagaac     2160
aactacaaga ccacccccc tgtgctggac agcgacggca gcttcttcct gtacagcaag     2220
ctcaccgtgg acaagagccg gtggcagcag ggcaacgtgt tcagctgcag cgtgatgcac     2280 gaggcccctgc acaaccacta cacccagaag agcctgagcc tgagcccgg caagtgataa    2340 tctagagggc ccgtttaaac ccgctgatca gcctcgactg tgccttctag ttgccagcca     2400
tctgttgttt gcccctcccc cgtgccttcc ttgaccctgg aaggtgccac tcccactgtc    2460
ctttcctaat aaaatgagga aattgcatcg cattgtctga gtaggtgtca ttctattctg    2520
gggggtgggg tggggcagga cagcaagggg gaggattggg aagacaatag caggcatgct    2580
ggggatgcgg tgggctctat ggcttctgag gcggaaagaa ccagctgggg ctctaggggg    2640
tatccccacg cgccctgtag cggcgcatta agcgcggcgg gtgtggtggt tacgcgcagc    2700
gtgaccgcta cacttgccag cgccctagcg cccgctcctt tcgctttctt cccttccttt    2760
ctcgccacgt tcgccggctt tccccgtcaa gctctaaatc gggggctccc tttagggttc    2820
cgatttagtg ctttacggca cctcgacccc aaaaaacttg attagggtga tggttcacgt    2880
agtgggccat cgccctgata cggttttt cgccctttga cgttggagtc cacgttcttt      2940
aatagtggac tcttgttcca aactggaaca acactcaacc ctatctcggt ctattctttt    3000
gatttataag ggattttgcc gatttcggcc tattggttaa aaaatgagct gatttaacaa    3060
aaatttaacg cgaattaatt ctgtggaatg tgtgtcagtt agggtgtgga aagtccccag    3120
```

```
gctccccagc aggcagaagt atgcaaagca tgcatctcaa ttagtcagca accaggtgtg    3180
gaaagtcccc aggctcccca gcaggcagaa gtatgcaaag catgcatctc aattagtcag    3240
caaccatagt cccgcccta actccgccca tcccgcccct aactccgccc agttccgccc     3300
attctccgcc ccatggctga ctaatttttt ttatttatgc agaggccgag gccgcctctg    3360
cctctgagct attccagaag tagtgaggag cttttttgg aggcctaggc ttttgcaaaa     3420
agctcccggg agcttgtata tccatttttcg gatctgatca agagacagga tgaggatcgt   3480
ttcgcatgat tgaacaagat ggattgcacg caggttctcc ggccgcttgg gtggagaggc    3540
tattcggcta tgactgggca acagacaa tcggctgctc tgatgccgcc gtgttccggc      3600
tgtcagcgca ggggcgcccg gttcttttg tcaagaccga cctgtccggt gccctgaatg     3660
aactgcagga cgaggcagcg cggctatcgt ggctggccac gacgggcgtt ccttgcgcag    3720
ctgtgctcga cgttgtcact gaagcgggaa gggactggct gctattgggc gaagtgccgg    3780
ggcaggatct cctgtcatct caccttgctc ctgccgagaa agtatccatc atggctgatg    3840
caatgcggcg gctgcatacg cttgatccgg ctacctgccc attcgaccac caagcgaaac    3900
atcgcatcga gcgagcacgt actcggatgg aagccggtct tgtcgatcag gatgatctgg    3960
acgaagagca tcagggctc gcgccagccg aactgttcgc caggctcaag gcgcgcatgc      4020
ccgacggcga ggatctcgtc gtgacccatg gcgatgcctg cttgccgaat atcatggtgg    4080
aaaatggccg cttttctgga ttcatcgact gtggccggct gggtgtggcg gatcgctatc    4140
aggacatagc gttggctacc cgtgatattg ctgaagagct tggcggcgaa tgggctgacc    4200
gcttcctcgt gctttacggt atcgccgctc ccgattcgca gcgcatcgcc ttctatcgcc    4260
ttcttgacga gttcttctga gcgggactct ggggttcgaa atgaccgacc aagcgacgcc    4320
caacctgcca tcacgagatt tcgattccac cgccgccttc tatgaaaggt tgggcttcgg    4380
aatcgttttc cgggacgccg gctggatgat cctccagcgc ggggatctca tgctggagtt    4440
cttcgcccac cccaacttgt ttattgcagc ttataatggt tacaaataaa gcaatagcat    4500
cacaaatttc acaaataaag cattttttc actgcattct agttgtggtt tgtccaaact    4560
catcaatgta tcttatcatg tctgtatacc gtcgacctct agctagagct tggcgtaatc    4620
atggtcatag ctgtttcctg tgtgaaattg ttatccgctc acaattccac acaacatacg    4680
agccggaagc ataaagtgta aagcctgggg tgcctaatga gtgagctaac tcacattaat    4740
tgcgttgcgc tcactgcccg ctttccagtc gggaaacctg tcgtgccagc tgcattaatg    4800
aatcggccaa cgcgcgggga gaggcggttt gcgtattggg cgctcttccg cttcctcgct    4860
cactgactcg ctgcgctcgg tcgttcggct gcggcgagcg gtatcagctc actcaaaggc    4920
ggtaatacgg ttatccacag aatcagggga taacgcagga agaacatgt gagcaaaagg     4980 ccagcaaaag gccaggaacc gtaaaaaggc cgcgttgctg gcgtttttcc ataggctccg    5040 ccccctgac gagcatcaca aaaatcgacg ctcaagtcag aggtggcgaa acccgacagg     5100
actataaaga taccaggcgt ttccccctgg aagctccctc gtgcgctctc ctgttccgac    5160
cctgccgctt accggatacc tgtccgcctt tctcccttcg ggaagcgtgg cgctttctca    5220
tagctcacgc tgtaggtatc tcagttcggt gtaggtcgtt cgctccaagc tgggctgtgt    5280
gcacgaaccc cccgttcagc ccgaccgctg cgccttatcc ggtaactatc gtcttgagtc    5340
caacccggta agacacgact tatcgccact ggcagcagcc actggtaaca ggattagcag    5400
agcgaggtat gtaggcggtg ctacagagtt cttgaagtgg tggcctaact acggctacac    5460
tagaagaaca gtatttggta tctgcgctct gctgaagcca gttaccttcg gaaaaagagt    5520
```

```
tggtagctct tgatccggca aacaaaccac cgctggtagc ggttttttg tttgcaagca    5580 gcagattacg cgcagaaaaa aaggatctca agaagatcct ttgatctttt ctacggggtc    5640
tgacgctcag tggaacgaaa actcacgtta agggattttg gtcatgagat tatcaaaaag    5700
gatcttcacc tagatccttt taaattaaaa atgaagtttt aaatcaatct aaagtatata    5760
tgagtaaact tggtctgaca gttaccaatg cttaatcagt gaggcaccta tctcagcgat    5820
ctgtctattt cgttcatcca tagttgcctg actccccgtc gtgtagataa ctacgatacg    5880
ggagggctta ccatctggcc ccagtgctgc aatgataccg cgagacccac gctcaccggc    5940
tccagattta tcagcaataa accagccagc cggaagggcc gagcgcagaa gtggtcctgc    6000
aactttatcc gcctccatcc agtctattaa ttgttgccgg gaagctagag taagtagttc    6060
gccagttaat agtttgcgca acgttgttgc cattgctaca ggcatcgtgg tgtcacgctc    6120
gtcgtttggt atggcttcat tcagctccgg ttcccaacga tcaaggcgag ttacatgatc    6180
ccccatgttg tgcaaaaaag cggttagctc cttcggtcct ccgatcgttg tcagaagtaa    6240
gttggccgca gtgttatcac tcatggttat ggcagcactg cataattctc ttactgtcat    6300
gccatccgta agatgctttt ctgtgactgg tgagtactca accaagtcat tctgagaata    6360
gtgtatgcgg cgaccgagtt gctcttgccc ggcgtcaata cgggataata ccgcgccaca    6420
tagcagaact ttaaaagtgc tcatcattgg aaaacgttct cggggcgaaa actctcaag    6480 gatcttaccg ctgttgagat ccagttcgat gtaacccact cgtgcaccca actgatcttc    6540
agcatctttt actttcacca gcgtttctgg gtgagcaaaa acaggaaggc aaaatgccgc    6600
aaaaaaggga ataagggcga cacggaaatg ttgaatactc atactcttcc ttttcaata    6660 ttattgaagc atttatcagg gttattgtct catgagcgga tacatatttg aatgtattta    6720
gaaaaataaa caaatagggg ttccgcgcac atttccccga aaagtgccac ctgacgtc      6778
```

<210> SEQ ID NO 38
<211> LENGTH: 6267
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Chemically synthesized - pSyn-C05-Ckappa

<400> SEQUENCE: 38

```
gacggatcgg gagatctccc gatccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgttaa ttaacatgaa     180
gaatctgctt agggttaggc gttttgcgct gcttcgctag gtggtcaata ttggccatta     240
gccatattat tcattggtta tatagcataa atcaatattg gctattggcc attgcatacg     300
ttgtatccat atcataatat gtacatttat attggctcat gtccaacatt accgccatgt     360
tgacattgat tattgactag ttattaatag taatcaatta cggggtcatt agttcatagc     420
ccatatatgg agttccgcgt tacataactt acggtaaatg gcccgcctgg ctgaccgccc     480
aacgaccccc gcccattgac gtcaataatg acgtatgttc ccatagtaac gccaataggg     540
actttccatt gacgtcaatg ggtggagtat ttacggtaaa ctgcccactt ggcagtacat     600
caagtgtatc atatgccaag tacgccccct attgacgtca atgacggtaa atggcccgcc     660
tggcattatg cccagtacat gaccttatgg gactttccta cttggcagta catctacgta     720
```

```
ttagtcatcg ctattaccat ggtgatgcgg ttttggcagt acatcaatgg gcgtggatag      780
cggtttgact cacggggatt tccaagtctc caccccattg acgtcaatgg gagtttgttt      840
tggcaccaaa atcaacggga ctttccaaaa tgtcgtaaca actccgcccc attgacgcaa      900
atgggcggta ggcgtgtacg gtgggaggtc tatataagca gagctcgttt agtgaaccgt      960
cagatcgcct ggagacgcca tccacgctgt tttgacctcc atagaagaca ccgggaccga     1020
tccagcctcc gcggccggga acggtgcatt ggaatcgatg actctcttag gtagccttgc     1080
agaagttggt cgtgaggcac tgggcaggta agtatcaagg ttacaagaca ggtttaagga     1140
gatcaataga aactgggctt gtcgagacag agaagactct tgcgtttctg ataggcacct     1200
attggtctta ctgacatcca ctttgccttt ctctccacag gtgtccactc ccagttcaat     1260
tacagctcgc caccatggcc tgccccggct tcctgtgggc cctggtgatc agcacctgcc     1320
tcgagttcag cggccctaag cggaccgtgg ccgctcccag cgtgttcatc ttccccccct     1380
ccgacgagca gctgaagagc ggcaccgcca gcgtggtgtg cctgctgaac aacttctacc     1440
cccgggaggc caaggtgcag tggaaggtgg acaacgccct gcagagcggc aacagccagg     1500
agagcgtgac cgagcaggac agcaaggact ccacctacag cctgagcagc accctcaccc     1560
tgagcaaggc cgactacgag aagcacaagg tgtacgcctg cgaggtgacc caccagggcc     1620
tgagcagccc cgtgaccaag agcttcaacc ggggcgagtg ttaatagact taagtttaaa     1680
ccgctgatca gcctcgactg tgccttctag ttgccagcca tctgttgttt gcccctcccc     1740
cgtgccttcc ttgaccctgg aaggtgccac tcccactgtc ctttcctaat aaaatgagga     1800
aattgcatcg cattgtctga gtaggtgtca ttctattctg ggggtgggg tgggcagga     1860 cagcaagggg gaggattggg aagacaatag caggcatgct ggggatgcgg tgggctctat     1920
ggcttctgag gcggaaagaa ccagctgggg ctctaggggg tatccccacg cgccctgtag     1980
cggcgcatta gcgcggcgg gtgtggtggt tacgcgcagc gtgaccgcta cacttgccag     2040
cgccctagcg cccgctcctt tcgctttctt cccttccttt ctcgccacgt tcgccggctt     2100
tccccgtcaa gctctaaatc ggggctccc tttagggttc cgatttagtg ctttacggca     2160
cctcgacccc aaaaaacttg attagggtga tggttcacgt agtgggccat cgccctgata     2220
gacggttttt cgccctttga cgttggagtc acgttctttt aatagtggac tcttgttcca     2280
aactggaaca acactcaacc ctatctcggt ctattctttt gatttataag ggattttggc     2340
catttcggcc tattggttaa aaaatgagct gatttaacaa aaatttaacg cgaattaatt     2400
ctgtggaatg tgtgtcagtt agggtgtgga aagtccccag gctccccagc aggcagaagt     2460
atgcaaagca tgcatctcaa ttagtcagca accaggtgtg gaaagtcccc aggctcccca     2520
gcaggcagaa gtatgcaaag catgcatctc aattagtcag caaccatagt cccgccccta     2580
actccgccca tcccgcccct aactccgccc agttccgccc attctccgcc ccatggctga     2640 ctaattttt ttatttatgc agaggccgag gccgcctctg cctctgagct attccagaag     2700
tagtgaggag gcttttttgg aggcctaggc ttttgcaaaa agctcccggg agcttgtata     2760
tccattttcg gatctgatca gcacgtgatg aaaaagcctg aactcaccgc gacgtctgtc     2820
gagaagtttc tgatcgaaaa gttcgacagc gtctccgacc tgatgcagct ctcggagggc     2880
gaagaatctc gtgctttcag cttcgatgta ggagggcgtg gatatgtcct gcgggtaaat     2940
agctgcgccg atggtttcta caaagatcgt tatgtttatc ggcactttgc atcggccgcg     3000
ctcccgattc cggaagtgct tgacattggg gaattcagcg agagcctgac ctattgcatc     3060
```

```
tcccgccgtg cacagggtgt cacgttgcaa gacctgcctg aaaccgaact gcccgctgtt    3120
ctgcagccgg tcgcggaggc catggatgcg atcgctgcgg ccgatcttag ccagacgagc    3180
gggttcggcc cattcggacc acaaggaatc ggtcaataca ctacatggcg tgatttcata    3240
tgcgcgattg ctgatcccca tgtgtatcac tggcaaactg tgatggacga caccgtcagt    3300
gcgtccgtcg cgcaggctct cgatgagctg atgctttggg ccgaggactg ccccgaagtc    3360
cggcacctcg tgcacgcgga tttcggctcc aacaatgtcc tgacgacaa tggccgcata    3420
acagcggtca ttgactggag cgaggcgatg ttcggggatt cccaatacga ggtcgccaac    3480
atcttcttct ggaggccgtg gttggcttgt atggagcagc agacgcgcta cttcgagcgg    3540
aggcatccgg agcttgcagg atcgccgcgg ctccgggcgt atatgctccg cattggtctt    3600
gaccaactct atcagagctt ggttgacggc aatttcgatg atgcagcttg gcgcagggt     3660
cgatgcgacg caatcgtccg atccggagcc gggactgtcg ggcgtacaca aatcgcccgc    3720
agaagcgcgg ccgtctggac cgatggctgt gtagaagtac tcgccgatag tggaaaccga    3780
cgccccagca ctcgtccgag ggcaaaggaa tagcacgtgc tacgagattt cgattccacc    3840
gccgccttct atgaaaggtt gggcttcgga atcgtttcc gggacgccgg ctggatgatc     3900
ctccagcgcg gggatctcat gctggagttc ttcgcccacc ccaacttgtt tattgcagct    3960
tataatggtt acaaataaag caatagcatc acaaatttca caaataaagc atttttttca    4020
ctgcattcta gttgtggttt gtccaaactc atcaatgtat cttatcatgt ctgtataccg    4080
tcgacctcta gctagagctt ggcgtaatca tggtcatagc tgtttcctgt gtgaaattgt    4140
tatccgctca caattccaca acatacga gccggaagca taagtgtaa agcctggggt       4200
gcctaatgag tgagctaact cacattaatt gcgttgcgct cactgcccgc tttccagtcg    4260
ggaaacctgt cgtgccagct gcattaatga atcggccaac gcgcggggag aggcggtttg    4320
cgtattgggc gctcttccgc ttcctcgctc actgactcgc tgcgctcggt cgttcggctg    4380
cggcgagcgg tatcagctca ctcaaaggcg gtaatacggt tatccacaga atcagggga    4440
aacgcaggaa agaacatgtg agcaaaaggc cagcaaaagg ccaggaaccg taaaaaggcc    4500
gcgttgctgg cgttttttcca taggctccgc cccctgacg agcatcacaa aaatcgacgc   4560
tcaagtcaga ggtggcgaaa cccgacagga ctataaagat accaggcgtt tcccctgga    4620
agctccctcg tgcgctctcc tgttccgacc ctgccgctta ccggatacct gtccgccttt    4680
ctcccttcgg gaagcgtggc gctttctcat agctcacgct gtaggtatct cagttcggtg    4740
taggtcgttc gctccaagct gggctgtgtg cacgaacccc ccgttcagcc cgaccgctgc    4800
gccttatccg gtaactatcg tcttgagtcc aacccggtaa gacacgactt atcgccactg    4860
gcagcagcca ctggtaacag gattagcaga gcgaggtatg taggcggtgc tacagagttc    4920
ttgaagtggt ggcctaacta cggctacact agaagaacag tatttggtat ctgcgctctg    4980
ctgaagccag ttaccttcgg aaaaagagtt ggtagctctt gatccggcaa acaaaccacc    5040
gctggtagcg gttttttgt ttgcaagcag cagattacgc gcagaaaaaa aggatctcaa     5100
gaagatcctt tgatctttc tacggggtct gacgctcagt ggaacgaaaa ctcacgttaa     5160
gggattttgg tcatgagatt atcaaaaagg atcttcacct agatcctttt aaattaaaaa    5220
tgaagtttta aatcaatcta agtatatat gagtaaactt ggtctgacag ttaccaatgc     5280
ttaatcagtg aggcacctat ctcagcgatc tgtctatttc gttcatccat agttgcctga    5340
ctccccgtcg tgtagataac tacgatacgg gagggcttac catctggccc cagtgctgca    5400
atgataccgc gagacccacg ctcaccggct ccagatttat cagcaataaa ccagccagcc    5460
```

```
ggaagggccg agcgcagaag tggtcctgca actttatccg cctccatcca gtctattaat    5520
tgttgccggg aagctagagt aagtagttcg ccagttaata gtttgcgcaa cgttgttgcc    5580
attgctacag gcatcgtggt gtcacgctcg tcgtttggta tggcttcatt cagctccggt    5640
tcccaacgat caaggcgagt tacatgatcc cccatgttgt gcaaaaaagc ggttagctcc    5700
ttcggtcctc cgatcgttgt cagaagtaag ttggccgcag tgttatcact catggttatg    5760
gcagcactgc ataattctct tactgtcatg ccatccgtaa gatgcttttc tgtgactggt    5820
gagtactcaa ccaagtcatt ctgagaatag tgtatgcggc gaccgagttg ctcttgcccg    5880
gcgtcaatac gggataatac cgcgccacat agcagaactt taaaagtgct catcattgga    5940
aaacgttctt cggggcgaaa actctcaagg atcttaccgc tgttgagatc cagttcgatg    6000
taacccactc gtgcacccaa ctgatcttca gcatctttta ctttcaccag cgtttctggg    6060
tgagcaaaaa caggaaggca aaatgccgca aaaagggaa taagggcgac acggaaatgt    6120
tgaatactca tactcttcct ttttcaatat tattgaagca tttatcaggg ttattgtctc    6180
atgagcggat acatatttga atgtatttag aaaaataaac aatagggggt ccgcgcaca    6240 tttcccccgaa aagtgccacc tgacgtc                                       6267

<210> SEQ ID NO 39
<211> LENGTH: 6283
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Chemically synthesized - pSyn-C04-Clambda

<400> SEQUENCE: 39
gacggatcgg gagatctccc gatccctat ggtgcactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgttaa ttaacatgaa    180
gaatctgctt agggttaggc gttttgcgct gcttcgctag gtggtcaata ttggccatta    240
gccatattat tcattggtta tatagcataa atcaatattg gctattggcc attgcatacg    300
ttgtatccat atcataatat gtacatttat attggctcat gtccaacatt accgccatgt    360
tgacattgat tattgactag ttattaatag taatcaatta cggggtcatt agttcatagc    420
ccatatatgg agttccgcgt tacataactt acggtaaatg gcccgcctgg ctgaccgccc    480
aacgaccccc gcccattgac gtcaataatg acgtatgttc ccatagtaac gccaataggg    540
actttccatt gacgtcaatg ggtggagtat ttacggtaaa ctgcccactt ggcagtacat    600
caagtgtatc atatgccaag tacgcccct attgacgtca atgacggtaa atggcccgcc    660
tggcattatg cccagtacat gaccttatgg gactttccta cttggcagta catctacgta    720
ttagtcatcg ctattaccat ggtgatgcgg ttttggcagt acatcaatgg gcgtggatag    780
cggtttgact cacggggatt tccaagtctc caccccattg acgtcaatgg gagtttgttt    840
tggcaccaaa atcaacggga ctttccaaaa tgtcgtaaca actccgcccc attgacgcaa    900
atgggcggta ggcgtgtacg gtgggaggtc tatataagca gagctcgttt agtgaaccgt    960
cagatcgcct ggagacgcca tccacgctgt tttgacctcc atagaagaca ccgggaccga   1020
tccagcctcc gcggccggga acggtgcatt ggaatcgatg actctcttag gtagccttgc   1080
agaagttggt cgtgaggcac tgggcaggta agtatcaagg ttacaagaca ggtttaagga   1140
```

```
gatcaataga aactgggctt gtcgagacag agaagactct tgcgtttctg ataggcacct    1200
attggtctta ctgacatcca ctttgccttt ctctccacag gtgtccactc ccagttcaat    1260
tacagctcgc caccatggcc tgccccggct tcctgtgggc cctggtgatc agcacctgcc    1320
tcgagatccc cggaccgcgg ccgcaagctt accgtgctgg gccagcccaa ggccgctccc    1380
agcgtgaccc tgttcccccc ctcctccgag gagctgcagg ccaacaaggc caccctggtg    1440
tgcctcatca gcgacttcta ccctggcgcc gtgaccgtgg cctggaaggc cgacagcagc    1500
cccgtgaagg ccggcgtgga gaccaccacc cccagcaagc agagcaacaa caagtacgcc    1560
gccagcagct acctgagcct caccccccgag cagtggaaga gccaccggag ctacagctgc    1620
caggtgaccc acgagggcag caccgtggag aagaccgtgg cccccaccga gtgcagctaa    1680
tagacttaag tttaaaccgc tgatcagcct cgactgtgcc ttctagttgc cagccatctg    1740
ttgtttgccc ctcccccgtg ccttccttga ccctggaagg tgccactccc actgtccttt    1800
cctaataaaa tgaggaaatt gcatcgcatt gtctgagtag gtgtcattct attctggggg    1860
gtggggtggg gcaggacagc aaggggagg attgggaaga caatagcagg catgctgggg     1920
atgcggtggg ctctatggct tctgaggcgg aaagaaccag ctggggctct aggggggtatc   1980 cccacgcgcc ctgtagcggc gcattaagcg cggcgggtgt ggtggttacg cgcagcgtga    2040
ccgctacact tgccagcgcc ctagcgcccg ctcctttcgc tttcttccct tcctttctcg    2100
ccacgttcgc cggctttccc cgtcaagctc taaatcgggg gctcccttta gggttccgat    2160
ttagtgcttt acggcacctc gaccccaaaa aacttgatta gggtgatggt tcacgtagtg    2220
ggccatcgcc ctgatagacg gttttttcgcc ctttgacgtt ggagtccacg ttctttaata   2280
gtggactctt gttccaaact ggaacaacac tcaaccctat ctcggtctat tcttttgatt    2340
tataagggat tttgccatt tcggcctatt ggttaaaaaa tgagctgatt taacaaaaat     2400
ttaacgcgaa ttaattctgt ggaatgtgtg tcagttaggg tgtggaaagt ccccaggctc    2460
cccagcaggc agaagtatgc aaagcatgca tctcaattag tcagcaacca ggtgtggaaa    2520
gtccccaggc tccccagcag gcagaagtat gcaaagcatg catctcaatt agtcagcaac    2580
catagtcccg cccctaactc cgcccatccc gcccctaact ccgcccagtt ccgcccattc    2640
tccgccccat ggctgactaa ttttttttat ttatgcagag gccgaggccg cctctgcctc    2700
tgagctattc cagaagtagt gaggaggctt ttttggaggc ctaggctttt gcaaaaagct    2760
cccgggagct tgtatatcca ttttcggatc tgatcagcac gtgatgaaaa agcctgaact    2820
caccgcgacg tctgtcgaga agtttctgat cgaaaagttc gacagcgtct ccgacctgat    2880
gcagctctcg gagggcgaag aatctcgtgc tttcagcttc gatgtaggag ggcgtggata    2940
tgtcctgcgg gtaaatagct gcgccgatgg tttctacaaa gatcgttatg tttatcggca    3000
ctttgcatcg gccgcgctcc cgattccgga agtgcttgac attggggaat tcagcgagag    3060
cctgacctat tgcatctccc gccgtgcaca gggtgtcacg ttgcaagacc tgcctgaaac    3120
cgaactgccc gctgttctgc agccggtcgc ggaggccatg gatgcgatcg ctgcggccga    3180
tcttagccag acgagcgggt tcggcccatt cggaccgcaa ggaatcggtc aatacactac    3240
atggcgtgat ttcatatgcg cgattgctga tccccatgtg tatcactggc aaactgtgat    3300
ggacgacacc gtcagtgcgt ccgtcgcgca ggctctcgat gagctgatgc tttgggccga    3360
ggactgcccc gaagtccggc acctcgtgca cgcggatttc ggctccaaca atgtcctgac    3420
ggacaatggc cgcataacag cggtcattga ctggagcgag gcgatgttcg gggattccca    3480
```

```
atacgaggtc gccaacatct tcttctggag gccgtggttg gcttgtatgg agcagcagac      3540
gcgctacttc gagcggaggc atccggagct tgcaggatcg ccgcggctcc gggcgtatat      3600
gctccgcatt ggtcttgacc aactctatca gagcttggtt gacggcaatt tcgatgatgc      3660
agcttgggcg cagggtcgat gcgacgcaat cgtccgatcc ggagccggga ctgtcgggcg      3720
tacacaaatc gcccgcagaa gcgcggccgt ctggaccgat ggctgtgtag aagtactcgc      3780
cgatagtgga aaccgacgcc ccagcactcg tccgagggca aaggaatagc acgtgctacg      3840
agatttcgat tccaccgccg ccttctatga aaggttgggc ttcggaatcg tttccggga       3900
cgccggctgg atgatcctcc agcgcgggga tctcatgctg gagttcttcg cccacccaa       3960
cttgtttatt gcagcttata atggttacaa ataaagcaat agcatcacaa atttcacaaa      4020
taaagcattt ttttcactgc attctagttg tggtttgtcc aaactcatca atgtatctta      4080
tcatgtctgt ataccgtcga cctctagcta gagcttggcg taatcatggt catagctgtt      4140
tcctgtgtga aattgttatc cgctcacaat tccacacaac atacgagccg aagcataaa       4200
gtgtaaagcc tggggtgcct aatgagtgag ctaactcaca ttaattgcgt tgcgctcact      4260
gcccgctttc cagtcgggaa acctgtcgtg ccagctgcat taatgaatcg gccaacgcgc      4320
ggggagaggc ggtttgcgta ttgggcgctc ttccgcttcc tcgctcactg actcgctgcg      4380
ctcggtcgtt cggctgcggc gagcggtatc agctcactca aaggcggtaa tacggttatc      4440
cacagaatca ggggataacg caggaaagaa catgtgagca aaaggccagc aaaaggccag      4500
gaaccgtaaa aaggccgcgt tgctggcgtt tttccatagg ctccgccccc ctgacgagca      4560
tcacaaaaat cgacgctcaa gtcagaggtg gcgaaacccg acaggactat aaagatacca      4620
ggcgtttccc cctggaagct ccctcgtgcg ctctcctgtt ccgaccctgc cgcttaccgg      4680
atacctgtcc gcctttctcc cttcgggaag cgtggcgctt tctcatagct cacgctgtag      4740
gtatctcagt tcggtgtagg tcgttcgctc caagctgggc tgtgtgcacg aaccccccgt      4800
tcagcccgac cgctgcgcct tatccggtaa ctatcgtctt gagtccaacc cggtaagaca      4860
cgacttatcg ccactggcag cagccactgg taacaggatt agcagagcga ggtatgtagg      4920
cggtgctaca gagttcttga agtggtggcc taactacggc tacactagaa gaacagtatt      4980
tggtatctgc gctctgctga agccagttac cttcggaaaa agagttggta gctcttgatc      5040
cggcaaacaa accaccgctg gtagcggttt ttttgtttgc aagcagcaga ttacgcgcag      5100
aaaaaaagga tctcaagaag atcctttgat cttttctacg gggtctgacg ctcagtggaa      5160
cgaaaactca cgttaaggga ttttggtcat gagattatca aaaaggatct tcacctagat      5220
ccttttaaat taaaaatgaa gttttaaatc aatctaaagt atatatgagt aaacttggtc      5280
tgacagttac caatgcttaa tcagtgaggc acctatctca gcgatctgtc tatttcgttc      5340
atccatagtt gcctgactcc ccgtcgtgta gataactacg atacgggagg gcttaccatc      5400
tggccccagt gctgcaatga taccgcgaga cccacgctca ccggctccag atttatcagc      5460
aataaaccag ccagccggaa gggccgagcg cagaagtggt cctgcaactt tatccgcctc      5520
catccagtct attaattgtt gccgggaagc tagagtaagt agttcgccag ttaatagttt      5580
gcgcaacgtt gttgccattg ctacaggcat cgtggtgtca cgctcgtcgt ttggtatggc      5640
ttcattcagc tccggttccc aacgatcaag gcgagttaca tgatccccca tgttgtgcaa      5700
aaaagcggtt agctccttcg gtcctccgat cgttgtcaga agtaagttgg ccgcagtgtt      5760
atcactcatg gttatggcag cactgcataa ttctcttact gtcatgccat ccgtaagatg      5820
cttttctgtg actggtgagt actcaaccaa gtcattctga gaatagtgta tgcggcgacc      5880
```

```
gagttgctct tgcccggcgt caatacggga taataccgcg ccacatagca gaactttaaa    5940
agtgctcatc attggaaaac gttcttcggg gcgaaaactc tcaaggatct taccgctgtt    6000
gagatccagt tcgatgtaac ccactcgtgc acccaactga tcttcagcat cttttacttt    6060
caccagcgtt tctgggtgag caaaaacagg aaggcaaaat gccgcaaaaa agggaataag    6120
ggcgacacgg aaatgttgaa tactcatact cttcctttt caatattatt gaagcattta     6180
tcagggttat tgtctcatga gcggatacat atttgaatgt atttagaaaa ataaacaaat    6240
aggggttccg cgcacatttc cccgaaaagt gccacctgac gtc                      6283

<210> SEQ ID NO 40
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized - Oligonucleotide 5k-I

<400> SEQUENCE: 40
acctgtctcg agttttccat ggctgacatc cagatgaccc agtctccatc ctcc           54

<210> SEQ ID NO 41
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized - Oligonucleotide sy3K-C

<400> SEQUENCE: 41
gggaccaagg tggagatcaa acggaccgtg gccgccccca gc                        42

<210> SEQ ID NO 42
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized - Oligonucleotide sy5L-A

<400> SEQUENCE: 42
acctgtctcg agttttccat ggcttcctcc gagctgaccc aggaccctgc tg             52

<210> SEQ ID NO 43
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized - Oligonucleotide 3L-B

<400> SEQUENCE: 43
ttttccttag cggccgcgac tcacctagga cggtcagctt ggtc                      44

<210> SEQ ID NO 44
<211> LENGTH: 49
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized - Oligonucleotide
      5H-Fshort

<400> SEQUENCE: 44
acctgtcttg aattctccat ggcccaggtg cagctgcagg agtccggcc            49

<210> SEQ ID NO 45
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized - Oligonucleotide sy3H-A

<400> SEQUENCE: 45
gcccttggtg ctagcgctgg agacggtcac cagggtgccc tggcccc             47

<210> SEQ ID NO 46
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized - Oligonucleotide 5H-B

<400> SEQUENCE: 46
acctgtcttg aattctccat ggccgaggtg cagctggtgg agtctg              46

<210> SEQ ID NO 47
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized - Oligonucleotide
      5H-B**65

<400> SEQUENCE: 47
acctgtcttg aattctccat ggccgaggtg cagctggtgg agtctggggg aggcttggta    60
catcc                                                               65

<210> SEQ ID NO 48
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized - Oligonucleotide 5H-A

<400> SEQUENCE: 48
acctgtcttg aattctccat ggcccaggtg cagctggtgc agtctgg             47

<210> SEQ ID NO 49
<211> LENGTH: 68
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Chemically synthesized - Oligonucleotide
      115int68

<400> SEQUENCE: 49
caccagggtg ccctggcccc agtagtcaaa gtaactcggc atctgcgacc ttgcacagta    60
atacacgg                                                            68

<210> SEQ ID NO 50
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Chemically synthesized - Heavy chain of 02-113
<220> FEATURE:
<221> NAME/KEY: CDS
<222> LOCATION: (1)..(1341)

<400> SEQUENCE: 50

| | | | | | | | | | | | | | | | | |
|---|---|---|---|---|---|---|---|---|---|---|---|---|---|---|---|---|---|
| cag | gtg | cag | ctg | cag | gag | tcc | ggc | gca | gga | ctg | ttg | aag | cct | tcg | gag | | 48 |
| Gln | Val | Gln | Leu | Gln | Glu | Ser | Gly | Ala | Gly | Leu | Leu | Lys | Pro | Ser | Glu | | |
| 1 | | | | 5 | | | | | 10 | | | | | 15 | | | |

| | | | | | | | | | | | | | | | | |
|---|---|---|---|---|---|---|---|---|---|---|---|---|---|---|---|---|---|
| acc | ctg | tcc | ctc | acc | tgc | gct | gtc | tat | ggt | ggg | tct | ttc | agt | ggc | tac | | 96 |
| Thr | Leu | Ser | Leu | Thr | Cys | Ala | Val | Tyr | Gly | Gly | Ser | Phe | Ser | Gly | Tyr | | |
| | | | 20 | | | | | 25 | | | | | 30 | | | | |

| | | | | | | | | | | | | | | | | |
|---|---|---|---|---|---|---|---|---|---|---|---|---|---|---|---|---|---|
| tac | tgg | agc | tgg | atc | cgg | cag | ccc | cca | ggg | aag | gga | ctg | gag | tgg | att | | 144 |
| Tyr | Trp | Ser | Trp | Ile | Arg | Gln | Pro | Pro | Gly | Lys | Gly | Leu | Glu | Trp | Ile | | |
| | | 35 | | | | | 40 | | | | | 45 | | | | | |

| | | | | | | | | | | | | | | | | |
|---|---|---|---|---|---|---|---|---|---|---|---|---|---|---|---|---|---|
| ggg | tat | atc | tat | tac | agt | ggg | agc | acc | aac | tac | aac | ccc | tcc | ctc | aag | | 192 |
| Gly | Tyr | Ile | Tyr | Tyr | Ser | Gly | Ser | Thr | Asn | Tyr | Asn | Pro | Ser | Leu | Lys | | |
| | 50 | | | | | 55 | | | | | 60 | | | | | | |

| | | | | | | | | | | | | | | | | |
|---|---|---|---|---|---|---|---|---|---|---|---|---|---|---|---|---|---|
| agt | cga | gtc | acc | ata | tca | gta | gac | acg | tcc | aag | aac | cag | ttc | tcc | ctg | | 240 |
| Ser | Arg | Val | Thr | Ile | Ser | Val | Asp | Thr | Ser | Lys | Asn | Gln | Phe | Ser | Leu | | |
| 65 | | | | | 70 | | | | | 75 | | | | | 80 | | |

| | | | | | | | | | | | | | | | | |
|---|---|---|---|---|---|---|---|---|---|---|---|---|---|---|---|---|---|
| aag | ctg | agc | tct | gtg | acc | gct | gcg | gac | acg | gcc | gtg | tat | tac | tgt | gca | | 288 |
| Lys | Leu | Ser | Ser | Val | Thr | Ala | Ala | Asp | Thr | Ala | Val | Tyr | Tyr | Cys | Ala | | |
| | | | | 85 | | | | | 90 | | | | | 95 | | | |

| | | | | | | | | | | | | | | | | |
|---|---|---|---|---|---|---|---|---|---|---|---|---|---|---|---|---|---|
| aag | gcc | cct | tat | atg | atg | tat | ttt | gac | tcc | tgg | ggc | cag | ggc | acc | ctg | | 336 |
| Lys | Ala | Pro | Tyr | Met | Met | Tyr | Phe | Asp | Ser | Trp | Gly | Gln | Gly | Thr | Leu | | |
| | | | 100 | | | | | 105 | | | | | 110 | | | | |

| | | | | | | | | | | | | | | | | |
|---|---|---|---|---|---|---|---|---|---|---|---|---|---|---|---|---|---|
| gtg | acc | gtc | tcc | agc | gct | agc | acc | aag | ggc | ccc | agc | gtg | ttc | ccc | ctg | | 384 |
| Val | Thr | Val | Ser | Ser | Ala | Ser | Thr | Lys | Gly | Pro | Ser | Val | Phe | Pro | Leu | | |
| | | 115 | | | | | 120 | | | | | 125 | | | | | |

| | | | | | | | | | | | | | | | | |
|---|---|---|---|---|---|---|---|---|---|---|---|---|---|---|---|---|---|
| gcc | ccc | agc | agc | aag | agc | acc | agc | ggc | ggc | aca | gcc | gcc | ctg | ggc | tgc | | 432 |
| Ala | Pro | Ser | Ser | Lys | Ser | Thr | Ser | Gly | Gly | Thr | Ala | Ala | Leu | Gly | Cys | | |
| | 130 | | | | | 135 | | | | | 140 | | | | | | |

| | | | | | | | | | | | | | | | | |
|---|---|---|---|---|---|---|---|---|---|---|---|---|---|---|---|---|---|
| ctg | gtg | aag | gac | tac | ttc | ccc | gag | ccc | gtg | acc | gtg | agc | tgg | aac | agc | | 480 |
| Leu | Val | Lys | Asp | Tyr | Phe | Pro | Glu | Pro | Val | Thr | Val | Ser | Trp | Asn | Ser | | |
| 145 | | | | | 150 | | | | | 155 | | | | | 160 | | |

| | | | | | | | | | | | | | | | | |
|---|---|---|---|---|---|---|---|---|---|---|---|---|---|---|---|---|---|
| ggc | gcc | ttg | acc | agc | ggc | gtg | cac | acc | ttc | ccc | gcc | gtg | ctg | cag | agc | | 528 |
| Gly | Ala | Leu | Thr | Ser | Gly | Val | His | Thr | Phe | Pro | Ala | Val | Leu | Gln | Ser | | |
| | | | | 165 | | | | | 170 | | | | | 175 | | | |

| | | | | | | | | | | | | | | | | |
|---|---|---|---|---|---|---|---|---|---|---|---|---|---|---|---|---|---|
| agc | ggc | ctg | tac | agc | ctg | agc | agc | gtg | gtg | acc | gtg | ccc | agc | agc | agc | | 576 |
| Ser | Gly | Leu | Tyr | Ser | Leu | Ser | Ser | Val | Val | Thr | Val | Pro | Ser | Ser | Ser | | |
| | | | 180 | | | | | 185 | | | | | 190 | | | | |

| | | | | | | | | | | | | | | | | |
|---|---|---|---|---|---|---|---|---|---|---|---|---|---|---|---|---|---|
| ctg | ggc | acc | cag | acc | tac | atc | tgc | aac | gtg | aac | cac | aag | ccc | agc | aac | | 624 |

```
            Leu Gly Thr Gln Thr Tyr Ile Cys Asn Val Asn His Lys Pro Ser Asn
                    195                 200                 205 acc aag gtg gac aaa cgc gtg gag ccc aag agc tgc gac aag acc cac                 672
Thr Lys Val Asp Lys Arg Val Glu Pro Lys Ser Cys Asp Lys Thr His
210                 215                 220 acc tgc ccc ccc tgc cct gcc ccc gag ctg ctg ggc gga ccc tcc gtg                 720
Thr Cys Pro Pro Cys Pro Ala Pro Glu Leu Leu Gly Gly Pro Ser Val
225                 230                 235                 240 ttc ctg ttc ccc ccc aag ccc aag gac acc ctc atg atc agc cgg acc                 768
Phe Leu Phe Pro Pro Lys Pro Lys Asp Thr Leu Met Ile Ser Arg Thr
                    245                 250                 255 ccc gag gtg acc tgc gtg gtg gtg gac gtg agc cac gag gac ccc gag                 816
Pro Glu Val Thr Cys Val Val Val Asp Val Ser His Glu Asp Pro Glu
                260                 265                 270 gtg aag ttc aac tgg tac gtg gac ggc gtg gag gtg cac aac gcc aag                 864
Val Lys Phe Asn Trp Tyr Val Asp Gly Val Glu Val His Asn Ala Lys
            275                 280                 285 acc aag ccc cgg gag gag cag tac aac agc acc tac cgg gtg gtg agc                 912
Thr Lys Pro Arg Glu Glu Gln Tyr Asn Ser Thr Tyr Arg Val Val Ser
        290                 295                 300 gtg ctc acc gtg ctg cac cag gac tgg ctg aac ggc aag gag tac aag                 960
Val Leu Thr Val Leu His Gln Asp Trp Leu Asn Gly Lys Glu Tyr Lys
305                 310                 315                 320 tgc aag gtg agc aac aag gcc ctg cct gcc ccc atc gag aag acc atc                1008
Cys Lys Val Ser Asn Lys Ala Leu Pro Ala Pro Ile Glu Lys Thr Ile
                    325                 330                 335 agc aag gcc aag ggc cag ccc cgg gag ccc cag gtg tac acc ctg ccc                1056
Ser Lys Ala Lys Gly Gln Pro Arg Glu Pro Gln Val Tyr Thr Leu Pro
                340                 345                 350 ccc agc cgg gag gag atg acc aag aac cag gtg tcc ctc acc tgt ctg                1104
Pro Ser Arg Glu Glu Met Thr Lys Asn Gln Val Ser Leu Thr Cys Leu
            355                 360                 365 gtg aag ggc ttc tac ccc agc gac atc gcc gtg gag tgg gag agc aac                1152
Val Lys Gly Phe Tyr Pro Ser Asp Ile Ala Val Glu Trp Glu Ser Asn
        370                 375                 380 ggc cag ccc gag aac aac tac aag acc acc ccc cct gtg ctg gac agc                1200
Gly Gln Pro Glu Asn Asn Tyr Lys Thr Thr Pro Pro Val Leu Asp Ser
385                 390                 395                 400 gac ggc agc ttc ttc ctg tac agc aag ctc acc gtg gac aag agc cgg                1248
Asp Gly Ser Phe Phe Leu Tyr Ser Lys Leu Thr Val Asp Lys Ser Arg
                    405                 410                 415 tgg cag cag ggc aac gtg ttc agc tgc agc gtg atg cac gag gcc ctg                1296
Trp Gln Gln Gly Asn Val Phe Ser Cys Ser Val Met His Glu Ala Leu
                420                 425                 430 cac aac cac tac acc cag aag agc ctg agc ctg agc ccc ggc aag                    1341
His Asn His Tyr Thr Gln Lys Ser Leu Ser Leu Ser Pro Gly Lys
            435                 440                 445

<210> SEQ ID NO 51
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chemically synthesized - Heavy chain of 02-113

<400> SEQUENCE: 51

Gln Val Gln Leu Gln Glu Ser Gly Ala Gly Leu Leu Lys Pro Ser Glu
1               5                   10                  15
```

```
Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Lys Ala Pro Tyr Met Met Tyr Phe Asp Ser Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
```

-continued

```
                    435                 440                 445
```

<210> SEQ ID NO 52
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Chemically synthesized - Heavy chain of 02-114
<220> FEATURE:
<221> NAME/KEY: CDS
<222> LOCATION: (1)..(1344)

<400> SEQUENCE: 52

| gag | gtg | cag | ctg | gtg | gag | tct | ggg | gga | ggc | ttg | gta | cag | cct | ggg | ggg | 48 |
|---|---|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly | |
| 1 | | | | 5 | | | | | 10 | | | | | 15 | | |

| tcc | ctg | aga | ctc | tcc | tgt | gca | gcc | tct | gga | ttc | acc | ttc | agt | agc | tat | 96 |
|---|---|---|---|---|---|---|---|---|---|---|---|---|---|---|---|---|
| Ser | Leu | Arg | Leu | Ser | Cys | Ala | Ala | Ser | Gly | Phe | Thr | Phe | Ser | Ser | Tyr | |
| | | | 20 | | | | | 25 | | | | | 30 | | | |

| agc | atg | aac | tgg | gtc | cgc | cag | gct | cca | ggg | aag | ggg | ctg | gag | tgg | gtt | 144 |
|---|---|---|---|---|---|---|---|---|---|---|---|---|---|---|---|---|
| Ser | Met | Asn | Trp | Val | Arg | Gln | Ala | Pro | Gly | Lys | Gly | Leu | Glu | Trp | Val | |
| | | 35 | | | | | 40 | | | | | 45 | | | | |

| tca | tac | att | agt | agt | agt | agt | acc | ata | tac | tac | gca | gac | tct | gtg | | 192 |
|---|---|---|---|---|---|---|---|---|---|---|---|---|---|---|---|---|
| Ser | Tyr | Ile | Ser | Ser | Ser | Ser | Thr | Ile | Tyr | Tyr | Ala | Asp | Ser | Val | | |
| 50 | | | | | 55 | | | | | 60 | | | | | | |

| aag | ggc | cga | ttc | acc | atc | tcc | aga | gac | aat | gcc | aag | aac | tca | ctg | tat | 240 |
|---|---|---|---|---|---|---|---|---|---|---|---|---|---|---|---|---|
| Lys | Gly | Arg | Phe | Thr | Ile | Ser | Arg | Asp | Asn | Ala | Lys | Asn | Ser | Leu | Tyr | |
| 65 | | | | 70 | | | | | 75 | | | | | 80 | | |

| ctg | caa | atg | aac | agc | ctg | aga | gac | gag | gac | acg | gcc | gtg | tat | tac | tgt | 288 |
|---|---|---|---|---|---|---|---|---|---|---|---|---|---|---|---|---|
| Leu | Gln | Met | Asn | Ser | Leu | Arg | Asp | Glu | Asp | Thr | Ala | Val | Tyr | Tyr | Cys | |
| | | | | 85 | | | | | 90 | | | | | 95 | | |

| gca | aag | gag | act | tgg | tgg | cag | tcc | ttt | gac | tac | tgg | ggc | cag | ggc | acc | 336 |
|---|---|---|---|---|---|---|---|---|---|---|---|---|---|---|---|---|
| Ala | Lys | Glu | Thr | Trp | Trp | Gln | Ser | Phe | Asp | Tyr | Trp | Gly | Gln | Gly | Thr | |
| | | | 100 | | | | | 105 | | | | | 110 | | | |

| ctg | gtg | acc | gtc | tcc | agc | gct | agc | acc | aag | ggc | ccc | agc | gtg | ttc | ccc | 384 |
|---|---|---|---|---|---|---|---|---|---|---|---|---|---|---|---|---|
| Leu | Val | Thr | Val | Ser | Ser | Ala | Ser | Thr | Lys | Gly | Pro | Ser | Val | Phe | Pro | |
| | | 115 | | | | | 120 | | | | | 125 | | | | |

| ctg | gcc | ccc | agc | agc | aag | agc | acc | agc | ggc | ggc | aca | gcc | gcc | ctg | ggc | 432 |
|---|---|---|---|---|---|---|---|---|---|---|---|---|---|---|---|---|
| Leu | Ala | Pro | Ser | Ser | Lys | Ser | Thr | Ser | Gly | Gly | Thr | Ala | Ala | Leu | Gly | |
| | 130 | | | | | 135 | | | | | 140 | | | | | |

| tgc | ctg | gtg | aag | gac | tac | ttc | ccc | gag | ccc | gtg | acc | gtg | agc | tgg | aac | 480 |
|---|---|---|---|---|---|---|---|---|---|---|---|---|---|---|---|---|
| Cys | Leu | Val | Lys | Asp | Tyr | Phe | Pro | Glu | Pro | Val | Thr | Val | Ser | Trp | Asn | |
| 145 | | | | 150 | | | | | 155 | | | | | 160 | | |

| agc | ggc | gcc | ttg | acc | agc | ggc | gtg | cac | acc | ttc | ccc | gcc | gtg | ctg | cag | 528 |
|---|---|---|---|---|---|---|---|---|---|---|---|---|---|---|---|---|
| Ser | Gly | Ala | Leu | Thr | Ser | Gly | Val | His | Thr | Phe | Pro | Ala | Val | Leu | Gln | |
| | | | 165 | | | | | 170 | | | | | 175 | | | |

| agc | agc | ggc | ctg | tac | agc | ctg | agc | agc | gtg | gtg | acc | gtg | ccc | agc | agc | 576 |
|---|---|---|---|---|---|---|---|---|---|---|---|---|---|---|---|---|
| Ser | Ser | Gly | Leu | Tyr | Ser | Leu | Ser | Ser | Val | Val | Thr | Val | Pro | Ser | Ser | |
| | | 180 | | | | | 185 | | | | | 190 | | | | |

| agc | ctg | ggc | acc | cag | acc | tac | atc | tgc | aac | gtg | aac | cac | aag | ccc | agc | 624 |
|---|---|---|---|---|---|---|---|---|---|---|---|---|---|---|---|---|
| Ser | Leu | Gly | Thr | Gln | Thr | Tyr | Ile | Cys | Asn | Val | Asn | His | Lys | Pro | Ser | |
| | 195 | | | | | 200 | | | | | 205 | | | | | |

| aac | acc | aag | gtg | gac | aaa | cgc | gtg | gag | ccc | aag | agc | tgc | gac | aag | acc | 672 |
|---|---|---|---|---|---|---|---|---|---|---|---|---|---|---|---|---|
| Asn | Thr | Lys | Val | Asp | Lys | Arg | Val | Glu | Pro | Lys | Ser | Cys | Asp | Lys | Thr | |
| 210 | | | | 215 | | | | | 220 | | | | | | | |

| cac | acc | tgc | ccc | ccc | tgc | cct | gcc | ccc | gag | ctg | ctg | ggc | gga | ccc | tcc | 720 |
|---|---|---|---|---|---|---|---|---|---|---|---|---|---|---|---|---|
| His | Thr | Cys | Pro | Pro | Cys | Pro | Ala | Pro | Glu | Leu | Leu | Gly | Gly | Pro | Ser | |
| 225 | | | | 230 | | | | | 235 | | | | | 240 | | |

| gtg | ttc | ctg | ttc | ccc | ccc | aag | ccc | aag | gac | acc | ctc | atg | atc | agc | cgg | 768 |
|---|---|---|---|---|---|---|---|---|---|---|---|---|---|---|---|---|
| Val | Phe | Leu | Phe | Pro | Pro | Lys | Pro | Lys | Asp | Thr | Leu | Met | Ile | Ser | Arg | |

```
                                                                                    816
acc ccc gag gtg acc tgc gtg gtg gtg gac gtg agc cac gag gac ccc
Thr Pro Glu Val Thr Cys Val Val Val Asp Val Ser His Glu Asp Pro
        260                 265                 270

864
gag gtg aag ttc aac tgg tac gtg gac ggc gtg gag gtg cac aac gcc
Glu Val Lys Phe Asn Trp Tyr Val Asp Gly Val Glu Val His Asn Ala
            275                 280                 285

912
aag acc aag ccc cgg gag gag cag tac aac agc acc tac cgg gtg gtg
Lys Thr Lys Pro Arg Glu Glu Gln Tyr Asn Ser Thr Tyr Arg Val Val
        290                 295                 300

960
agc gtg ctc acc gtg ctg cac cag gac tgg ctg aac ggc aag gag tac
Ser Val Leu Thr Val Leu His Gln Asp Trp Leu Asn Gly Lys Glu Tyr
305                 310                 315                 320

1008
aag tgc aag gtg agc aac aag gcc ctg cct gcc ccc atc gag aag acc
Lys Cys Lys Val Ser Asn Lys Ala Leu Pro Ala Pro Ile Glu Lys Thr
            325                 330                 335

1056
atc agc aag gcc aag ggc cag ccc cgg gag ccc cag gtg tac acc ctg
Ile Ser Lys Ala Lys Gly Gln Pro Arg Glu Pro Gln Val Tyr Thr Leu
        340                 345                 350

1104
ccc ccc agc cgg gag gag atg acc aag aac cag gtg tcc ctc acc tgt
Pro Pro Ser Arg Glu Glu Met Thr Lys Asn Gln Val Ser Leu Thr Cys
    355                 360                 365

1152
ctg gtg aag ggc ttc tac ccc agc gac atc gcc gtg gag tgg gag agc
Leu Val Lys Gly Phe Tyr Pro Ser Asp Ile Ala Val Glu Trp Glu Ser
370                 375                 380

1200
aac ggc cag ccc gag aac aac tac aag acc acc ccc cct gtg ctg gac
Asn Gly Gln Pro Glu Asn Asn Tyr Lys Thr Thr Pro Pro Val Leu Asp
385                 390                 395                 400

1248
agc gac ggc agc ttc ttc ctg tac agc aag ctc acc gtg gac aag agc
Ser Asp Gly Ser Phe Phe Leu Tyr Ser Lys Leu Thr Val Asp Lys Ser
                405                 410                 415

1296
cgg tgg cag cag ggc aac gtg ttc agc tgc agc gtg atg cac gag gcc
Arg Trp Gln Gln Gly Asn Val Phe Ser Cys Ser Val Met His Glu Ala
            420                 425                 430

1344
ctg cac aac cac tac acc cag aag agc ctg agc ctg agc ccc ggc aag
Leu His Asn His Tyr Thr Gln Lys Ser Leu Ser Leu Ser Pro Gly Lys
        435                 440                 445
```

<210> SEQ ID NO 53
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chemically synthesized - Heavy chain of 02-114

<400> SEQUENCE: 53

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80
```

Leu Gln Met Asn Ser Leu Arg Asp Glu Asp Thr Ala Val Tyr Tyr Cys
                85                  90                  95

Ala Lys Glu Thr Trp Trp Gln Ser Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 54
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Chemically synthesized - Heavy chain of 02-115

```
<220> FEATURE:
<221> NAME/KEY: CDS
<222> LOCATION: (1)..(1344)

<400> SEQUENCE: 54 cag gtg cag ctg gtg cag tct ggg gct gag gcg aag aag cct ggg gcc      48
Gln Val Gln Leu Val Gln Ser Gly Ala Glu Ala Lys Lys Pro Gly Ala
1               5                   10                  15 tca gtg aag gtc tcc tgc aag gct tct gga tac acc ttc acc ggc tac      96
Ser Val Lys Val Ser Cys Lys Ala Ser Gly Tyr Thr Phe Thr Gly Tyr
            20                  25                  30 tat atg cac tgg gtg cga cag gcc cct gga caa ggg ctt gag tgg atg     144
Tyr Met His Trp Val Arg Gln Ala Pro Gly Gln Gly Leu Glu Trp Met
        35                  40                  45 gga tgg atc agc gct tac aat ggt aac aca aac tat gca cag aag ctc     192
Gly Trp Ile Ser Ala Tyr Asn Gly Asn Thr Asn Tyr Ala Gln Lys Leu
    50                  55                  60 cag ggc aga gtc acc atg acc aca gac aca tcc acg agc aca gcc tac     240
Gln Gly Arg Val Thr Met Thr Thr Asp Thr Ser Thr Ser Thr Ala Tyr
65                  70                  75                  80 atg gag ctg agg agc ctg aga tct gac gac acg gcc gtg tat tac tgt     288
Met Glu Leu Arg Ser Leu Arg Ser Asp Asp Thr Ala Val Tyr Tyr Cys
                85                  90                  95 gca agg tcg cag atg ccg agt tac ttt gac tac tgg ggc cag ggc acc     336
Ala Arg Ser Gln Met Pro Ser Tyr Phe Asp Tyr Trp Gly Gln Gly Thr
            100                 105                 110 ctg gtg acc gtc tcc agc gct agc acc aag ggc ccc agc gtg ttc ccc     384
Leu Val Thr Val Ser Ser Ala Ser Thr Lys Gly Pro Ser Val Phe Pro
        115                 120                 125 ctg gcc ccc agc agc aag agc acc agc ggc ggc aca gcc gcc ctg ggc     432
Leu Ala Pro Ser Ser Lys Ser Thr Ser Gly Gly Thr Ala Ala Leu Gly
    130                 135                 140 tgc ctg gtg aag gac tac ttc ccc gag ccc gtg acc gtg agc tgg aac     480
Cys Leu Val Lys Asp Tyr Phe Pro Glu Pro Val Thr Val Ser Trp Asn
145                 150                 155                 160 agc ggc gcc ttg acc agc ggc gtg cac acc ttc ccc gcc gtg ctg cag     528
Ser Gly Ala Leu Thr Ser Gly Val His Thr Phe Pro Ala Val Leu Gln
                165                 170                 175 agc agc ggc ctg tac agc ctg agc agc gtg gtg acc gtg ccc agc agc     576
Ser Ser Gly Leu Tyr Ser Leu Ser Ser Val Val Thr Val Pro Ser Ser
            180                 185                 190 agc ctg ggc acc cag acc tac atc tgc aac gtg aac cac aag ccc agc     624
Ser Leu Gly Thr Gln Thr Tyr Ile Cys Asn Val Asn His Lys Pro Ser
        195                 200                 205 aac acc aag gtg gac aaa cgc gtg gag ccc aag agc tgc gac aag acc     672
Asn Thr Lys Val Asp Lys Arg Val Glu Pro Lys Ser Cys Asp Lys Thr
    210                 215                 220 cac acc tgc ccc ccc tgc cct gcc ccc gag ctg ctg ggc gga ccc tcc     720
His Thr Cys Pro Pro Cys Pro Ala Pro Glu Leu Leu Gly Gly Pro Ser
225                 230                 235                 240 gtg ttc ctg ttc ccc ccc aag ccc aag gac acc ctc atg atc agc cgg     768
Val Phe Leu Phe Pro Pro Lys Pro Lys Asp Thr Leu Met Ile Ser Arg
                245                 250                 255 acc ccc gag gtg acc tgc gtg gtg gtg gac gtg agc cac gag gac ccc     816
Thr Pro Glu Val Thr Cys Val Val Val Asp Val Ser His Glu Asp Pro
            260                 265                 270 gag gtg aag ttc aac tgg tac gtg gac ggc gtg gag gtg cac aac gcc     864
Glu Val Lys Phe Asn Trp Tyr Val Asp Gly Val Glu Val His Asn Ala
        275                 280                 285 aag acc aag ccc cgg gag gag cag tac aac agc acc tac cgg gtg gtg     912
```

```
Lys Thr Lys Pro Arg Glu Glu Gln Tyr Asn Ser Thr Tyr Arg Val Val
    290                 295                 300 agc gtg ctc acc gtg ctg cac cag gac tgg ctg aac ggc aag gag tac      960
Ser Val Leu Thr Val Leu His Gln Asp Trp Leu Asn Gly Lys Glu Tyr
305                 310                 315                 320 aag tgc aag gtg agc aac aag gcc ctg cct gcc ccc atc gag aag acc     1008
Lys Cys Lys Val Ser Asn Lys Ala Leu Pro Ala Pro Ile Glu Lys Thr
                325                 330                 335 atc agc aag gcc aag ggc cag ccc cgg gag ccc cag gtg tac acc ctg     1056
Ile Ser Lys Ala Lys Gly Gln Pro Arg Glu Pro Gln Val Tyr Thr Leu
            340                 345                 350 ccc ccc agc cgg gag gag atg acc aag aac cag gtg tcc ctc acc tgt     1104
Pro Pro Ser Arg Glu Glu Met Thr Lys Asn Gln Val Ser Leu Thr Cys
        355                 360                 365 ctg gtg aag ggc ttc tac ccc agc gac atc gcc gtg gag tgg gag agc     1152
Leu Val Lys Gly Phe Tyr Pro Ser Asp Ile Ala Val Glu Trp Glu Ser
    370                 375                 380 aac ggc cag ccc gag aac aac tac aag acc acc ccc cct gtg ctg gac     1200
Asn Gly Gln Pro Glu Asn Asn Tyr Lys Thr Thr Pro Pro Val Leu Asp
385                 390                 395                 400 agc gac ggc agc ttc ttc ctg tac agc aag ctc acc gtg gac aag agc     1248
Ser Asp Gly Ser Phe Phe Leu Tyr Ser Lys Leu Thr Val Asp Lys Ser
                405                 410                 415 cgg tgg cag cag ggc aac gtg ttc agc tgc agc gtg atg cac gag gcc     1296
Arg Trp Gln Gln Gly Asn Val Phe Ser Cys Ser Val Met His Glu Ala
            420                 425                 430 ctg cac aac cac tac acc cag aag agc ctg agc ctg agc ccc ggc aag     1344
Leu His Asn His Tyr Thr Gln Lys Ser Leu Ser Leu Ser Pro Gly Lys
        435                 440                 445

<210> SEQ ID NO 55
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chemically synthesized - Heavy chain of 02-115

<400> SEQUENCE: 55

Gln Val Gln Leu Val Gln Ser Gly Ala Glu Ala Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Gln Met Pro Ser Tyr Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140
```

```
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Gln Thr Tyr Ile Cys Asn Val Asn His Lys Pro Ser
    195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Arg Glu Glu Met Thr Lys Asn Gln Val Ser Leu Thr Cys
    355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
    435                 440                 445
```

<210> SEQ ID NO 56
<211> LENGTH: 1344
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Chemically synthesized - Heavy chain of 02-116
<220> FEATURE:
<221> NAME/KEY: CDS
<222> LOCATION: (1)..(1344)

<400> SEQUENCE: 56

```
gag gtg cag ctg gtg gag tct ggg gga ggc ttg gta cag cct ggg ggg      48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttt agc agc tat      96
Ser Leu Arg Leu Ser Cys Ala Ala Ser Gly Phe Thr Phe Ser Ser Tyr
```

-continued

|  | 20 |  |  |  | 25 |  |  |  | 30 |  |  |  |  |
|---|---|---|---|---|---|---|---|---|---|---|---|---|---|
| gcc | atg | agc | tgg | gtc | cgc | cag | gct | cca | ggg | aag | ggg | ctg | gag | tgg | gtc | 144 |
| Ala | Met | Ser | Trp | Val | Arg | Gln | Ala | Pro | Gly | Lys | Gly | Leu | Glu | Trp | Val |  |
|  | 35 |  |  |  | 40 |  |  |  | 45 |  |  |  |  |

```
gcc atg agc tgg gtc cgc cag gct cca ggg aag ggg ctg gag tgg gtc       144
Ala Met Ser Trp Val Arg Gln Ala Pro Gly Lys Gly Leu Glu Trp Val
     35                  40                  45 tca gct att agt ggt agt ggt ggt agc aca tac tac gca gac tcc gtg       192
Ser Ala Ile Ser Gly Ser Gly Gly Ser Thr Tyr Tyr Ala Asp Ser Val
 50                  55                  60 aag ggc cgg ttc acc atc tcc aga gac aat tcc aag aac acg ctg tat       240
Lys Gly Arg Phe Thr Ile Ser Arg Asp Asn Ser Lys Asn Thr Leu Tyr
 65                  70                  75                  80 ctg caa atg aac agc cta aga gcc gag gac acg gcc gtg tat tac tgt       288
Leu Gln Met Asn Ser Leu Arg Ala Glu Asp Thr Ala Val Tyr Tyr Cys
                 85                  90                  95 gca aag gac gct ctt tgg ctg gct ttt gac tac tgg ggc cag ggc acc       336
Ala Lys Asp Ala Leu Trp Leu Ala Phe Asp Tyr Trp Gly Gln Gly Thr
                100                 105                 110 ctg gtg acc gtc tcc agc gct agc acc aag ggc ccc agc gtg ttc ccc       384
Leu Val Thr Val Ser Ser Ala Ser Thr Lys Gly Pro Ser Val Phe Pro
            115                 120                 125 ctg gcc ccc agc agc aag agc acc agc ggc gga aca gcc gcc ctg ggc       432
Leu Ala Pro Ser Ser Lys Ser Thr Ser Gly Gly Thr Ala Ala Leu Gly
        130                 135                 140 tgc ctg gtg aag gac tac ttc ccc gag ccc gtg acc gtg agc tgg aac       480
Cys Leu Val Lys Asp Tyr Phe Pro Glu Pro Val Thr Val Ser Trp Asn
145                 150                 155                 160 agc ggc gcc ttg acc agc ggc gtg cac acc ttc ccc gcc gtg ctg cag       528
Ser Gly Ala Leu Thr Ser Gly Val His Thr Phe Pro Ala Val Leu Gln
                165                 170                 175 agc agc ggc ctg tac agc ctg agc agc gtg gtg acc gtg ccc agc agc       576
Ser Ser Gly Leu Tyr Ser Leu Ser Ser Val Val Thr Val Pro Ser Ser
                180                 185                 190 agc ctg ggc acc cag acc tac atc tgc aac gtg aac cac aag ccc agc       624
Ser Leu Gly Thr Gln Thr Tyr Ile Cys Asn Val Asn His Lys Pro Ser
            195                 200                 205 aac acc aag gtg gac aaa cgc gtg gag ccc aag agc tgc gac aag acc       672
Asn Thr Lys Val Asp Lys Arg Val Glu Pro Lys Ser Cys Asp Lys Thr
        210                 215                 220 cac acc tgc ccc ccc tgc cct gcc ccc gag ctg ctg ggc gga ccc tcc       720
His Thr Cys Pro Pro Cys Pro Ala Pro Glu Leu Leu Gly Gly Pro Ser
225                 230                 235                 240 gtg ttc ctg ttc ccc ccc aag ccc aag gac acc ctc atg atc agc cgg       768
Val Phe Leu Phe Pro Pro Lys Pro Lys Asp Thr Leu Met Ile Ser Arg
                245                 250                 255 acc ccc gag gtg acc tgc gtg gtg gtg gac gtg agc cac gag gac ccc       816
Thr Pro Glu Val Thr Cys Val Val Val Asp Val Ser His Glu Asp Pro
                260                 265                 270 gag gtg aag ttc aac tgg tac gtg gac ggc gtg gag gtg cac aac gcc       864
Glu Val Lys Phe Asn Trp Tyr Val Asp Gly Val Glu Val His Asn Ala
            275                 280                 285 aag acc aag ccc cgg gag gag cag tac aac agc acc tac cgg gtg gtg       912
Lys Thr Lys Pro Arg Glu Glu Gln Tyr Asn Ser Thr Tyr Arg Val Val
        290                 295                 300 agc gtg ctc acc gtg ctg cac cag gac tgg ctg aac ggc aag gag tac       960
Ser Val Leu Thr Val Leu His Gln Asp Trp Leu Asn Gly Lys Glu Tyr
305                 310                 315                 320 aag tgc aag gtg agc aac aag gcc ctg cct gcc ccc atc gag aag acc      1008
Lys Cys Lys Val Ser Asn Lys Ala Leu Pro Ala Pro Ile Glu Lys Thr
                325                 330                 335 atc agc aag gcc aag ggc cag ccc cgg gag ccc cag gtg tac acc ctg      1056
```

```
Ile Ser Lys Ala Lys Gly Gln Pro Arg Glu Pro Gln Val Tyr Thr Leu
            340                 345                 350 ccc ccc agc cgg gag gag atg acc aag aac cag gtg tcc ctc acc tgt    1104
Pro Pro Ser Arg Glu Glu Met Thr Lys Asn Gln Val Ser Leu Thr Cys
            355                 360                 365 ctg gtg aag ggc ttc tac ccc agc gac atc gcc gtg gag tgg gag agc    1152
Leu Val Lys Gly Phe Tyr Pro Ser Asp Ile Ala Val Glu Trp Glu Ser
370                 375                 380 aac ggc cag ccc gag aac aac tac aag acc acc ccc cct gtg ctg gac    1200
Asn Gly Gln Pro Glu Asn Asn Tyr Lys Thr Thr Pro Pro Val Leu Asp
385                 390                 395                 400 agc gac ggc agc ttc ttc ctg tac agc aag ctc acc gtg gac aag agc    1248
Ser Asp Gly Ser Phe Phe Leu Tyr Ser Lys Leu Thr Val Asp Lys Ser
            405                 410                 415 cgg tgg cag cag ggc aac gtg ttc agc tgc agc gtg atg cac gag gcc    1296
Arg Trp Gln Gln Gly Asn Val Phe Ser Cys Ser Val Met His Glu Ala
            420                 425                 430 ctg cac aac cac tac acc cag aag agc ctg agc ctg agc ccc ggc aag    1344
Leu His Asn His Tyr Thr Gln Lys Ser Leu Ser Leu Ser Pro Gly Lys
            435                 440                 445
```

<210> SEQ ID NO 57
<211> LENGTH: 448
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Chemically synthesized - Heavy chain of 02-116

<400> SEQUENCE: 57

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ala Leu Trp Leu Ala Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205
```

```
Asn Thr Lys Val Asp Lys Arg Val Glu Pro Lys Ser Cys Asp Lys Thr
    210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445

<210> SEQ ID NO 58
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Chemically synthesized - Heavy chain of 02-117
<220> FEATURE:
<221> NAME/KEY: CDS
<222> LOCATION: (1)..(1341)

<400> SEQUENCE: 58 gag gtg cag ctg gtg gag tct ggg gga ggc ttg gta cat cct ggg ggg    48
Glu Val Gln Leu Val Glu Ser Gly Gly Gly Leu Val His Pro Gly Gly
1               5                   10                  15 tcc ctg aga ctc tcc tgt gca ggc tct gga ttc acc ttc agt agc tat    96
Ser Leu Arg Leu Ser Cys Ala Gly Ser Gly Phe Thr Phe Ser Ser Tyr
            20                  25                  30 gct atg cac tgg gtt cgc cag gct cca gga aaa ggt ctg gag tgg gta   144
Ala Met His Trp Val Arg Gln Ala Pro Gly Lys Gly Leu Glu Trp Val
        35                  40                  45 tca gct att ggt act ggt ggt ggc aca tac tat gca gac tcc gtg aag   192
Ser Ala Ile Gly Thr Gly Gly Gly Thr Tyr Tyr Ala Asp Ser Val Lys
    50                  55                  60 ggc cga ttc acc atc tcc aga gac aat gcc aag aac tcc ttg tat ctt   240
Gly Arg Phe Thr Ile Ser Arg Asp Asn Ala Lys Asn Ser Leu Tyr Leu
```

```
                65                  70                  75                  80 caa atg aac agc ctg aga gcc gag gac acg gcc gtg tat tac tgt gca         288
Gln Met Asn Ser Leu Arg Ala Glu Asp Thr Ala Val Tyr Tyr Cys Ala
                    85                  90                  95 agg tct acg cct tgg ttt tcc ttt gac tac tgg ggc cag ggc acc ctg         336
Arg Ser Thr Pro Trp Phe Ser Phe Asp Tyr Trp Gly Gln Gly Thr Leu
                100                 105                 110 gtg acc gtc tcc agc gct agc acc aag ggc ccc agc gtg ttc ccc ctg         384
Val Thr Val Ser Ser Ala Ser Thr Lys Gly Pro Ser Val Phe Pro Leu
            115                 120                 125 gcc ccc agc agc aag agc acc agc ggc ggc aca gcc gcc ctg ggc tgc         432
Ala Pro Ser Ser Lys Ser Thr Ser Gly Gly Thr Ala Ala Leu Gly Cys
        130                 135                 140 ctg gtg aag gac tac ttc ccc gag ccc gtg acc gtg agc tgg aac agc         480
Leu Val Lys Asp Tyr Phe Pro Glu Pro Val Thr Val Ser Trp Asn Ser
145                 150                 155                 160 ggc gcc ttg acc agc ggc gtg cac acc ttc ccc gcc gtg ctg cag agc         528
Gly Ala Leu Thr Ser Gly Val His Thr Phe Pro Ala Val Leu Gln Ser
                165                 170                 175 agc ggc ctg tac agc ctg agc agc gtg gtg acc gtg ccc agc agc agc         576
Ser Gly Leu Tyr Ser Leu Ser Ser Val Val Thr Val Pro Ser Ser Ser
                180                 185                 190 ctg ggc acc cag acc tac atc tgc aac gtg aac cac aag ccc agc aac         624
Leu Gly Thr Gln Thr Tyr Ile Cys Asn Val Asn His Lys Pro Ser Asn
            195                 200                 205 acc aag gtg gac aaa cgc gtg gag ccc aag agc tgc gac aag acc cac         672
Thr Lys Val Asp Lys Arg Val Glu Pro Lys Ser Cys Asp Lys Thr His
        210                 215                 220 acc tgc ccc ccc tgc cct gcc ccc gag ctg ctg ggc gga ccc tcc gtg         720
Thr Cys Pro Pro Cys Pro Ala Pro Glu Leu Leu Gly Gly Pro Ser Val
225                 230                 235                 240 ttc ctg ttc ccc ccc aag ccc aag gac acc ctc atg atc agc cgg acc         768
Phe Leu Phe Pro Pro Lys Pro Lys Asp Thr Leu Met Ile Ser Arg Thr
                245                 250                 255 ccc gag gtg acc tgc gtg gtg gtg gac gtg agc cac gag gac ccc gag         816
Pro Glu Val Thr Cys Val Val Val Asp Val Ser His Glu Asp Pro Glu
                260                 265                 270 gtg aag ttc aac tgg tac gtg gac ggc gtg gag gtg cac aac gcc aag         864
Val Lys Phe Asn Trp Tyr Val Asp Gly Val Glu Val His Asn Ala Lys
            275                 280                 285 acc aag ccc cgg gag gag cag tac aac agc acc tac cgg gtg gtg agc         912
Thr Lys Pro Arg Glu Glu Gln Tyr Asn Ser Thr Tyr Arg Val Val Ser
        290                 295                 300 gtg ctc acc gtg ctg cac cag gac tgg ctg aac ggc aag gag tac aag         960
Val Leu Thr Val Leu His Gln Asp Trp Leu Asn Gly Lys Glu Tyr Lys
305                 310                 315                 320 tgc aag gtg agc aac aag gcc ctg cct gcc ccc atc gag aag acc atc        1008
Cys Lys Val Ser Asn Lys Ala Leu Pro Ala Pro Ile Glu Lys Thr Ile
                325                 330                 335 agc aag gcc aag ggc cag ccc cgg gag ccc cag gtg tac acc ctg ccc        1056
Ser Lys Ala Lys Gly Gln Pro Arg Glu Pro Gln Val Tyr Thr Leu Pro
                340                 345                 350 ccc agc cgg gag gag atg acc aag aac cag gtg tcc ctc acc tgt ctg        1104
Pro Ser Arg Glu Glu Met Thr Lys Asn Gln Val Ser Leu Thr Cys Leu
            355                 360                 365 gtg aag ggc ttc tac ccc agc gac atc gcc gtg gag tgg gag agc aac        1152
Val Lys Gly Phe Tyr Pro Ser Asp Ile Ala Val Glu Trp Glu Ser Asn
        370                 375                 380 ggc cag ccc gag aac aac tac aag acc acc ccc cct gtg ctg gac agc        1200
```

```
Gly Gln Pro Glu Asn Asn Tyr Lys Thr Thr Pro Val Leu Asp Ser
385                 390                 395                 400 gac ggc agc ttc ttc ctg tac agc aag ctc acc gtg gac aag agc cgg    1248
Asp Gly Ser Phe Phe Leu Tyr Ser Lys Leu Thr Val Asp Lys Ser Arg
            405                 410                 415 tgg cag cag ggc aac gtg ttc agc tgc agc gtg atg cac gag gcc ctg    1296
Trp Gln Gln Gly Asn Val Phe Ser Cys Ser Val Met His Glu Ala Leu
            420                 425                 430 cac aac cac tac acc cag aag agc ctg agc ctg agc ccc ggc aag        1341
His Asn His Tyr Thr Gln Lys Ser Leu Ser Leu Ser Pro Gly Lys
            435                 440                 445
```

<210> SEQ ID NO 59
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Chemically synthesized - Heavy chain of 02-117

<400> SEQUENCE: 59

```
Glu Val Gln Leu Val Glu Ser Gly Gly Gly Leu Val His Pro Gly Gly
1               5                   10                  15

Ser Leu Arg Leu Ser Cys Ala Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Gly Thr Gly Gly Gly Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Ser Thr Pro Trp Phe Ser Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270
```

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 60
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Chemically synthesized - Heavy chain of 02-118
<220> FEATURE:
<221> NAME/KEY: CDS
<222> LOCATION: (1)..(1341)

<400> SEQUENCE: 60 gag gtg cag ctg gtg gag tct ggg gga ggc ttg gta cat cct ggg ggg      48
Glu Val Gln Leu Val Glu Ser Gly Gly Gly Leu Val His Pro Gly Gly
1               5                   10                  15 tcc ctg aga ctc tcc tgt gca ggc tct gga ttc acc ttc agt agc tat      96
Ser Leu Arg Leu Ser Cys Ala Gly Ser Gly Phe Thr Phe Ser Ser Tyr
            20                  25                  30 gct atg cac tgg gtt cgc cag gct cca gga aaa ggt ctg gag tgg gta     144
Ala Met His Trp Val Arg Gln Ala Pro Gly Lys Gly Leu Glu Trp Val
        35                  40                  45 tca gct att agt act ggt ggt ggc aca tac tat gca gac tcc gtg aag     192
Ser Ala Ile Ser Thr Gly Gly Gly Thr Tyr Tyr Ala Asp Ser Val Lys
    50                  55                  60 ggc cga ttc acc atc tcc aga gac aat gcc aag aac tcc ttg tat ctt     240
Gly Arg Phe Thr Ile Ser Arg Asp Asn Ala Lys Asn Ser Leu Tyr Leu
65                  70                  75                  80 caa atg aac agc ctg aga gcc gag gac acg gcc gtg tat tac tgt gca     288
Gln Met Asn Ser Leu Arg Ala Glu Asp Thr Ala Val Tyr Tyr Cys Ala
                85                  90                  95 agg agt gct tgg tgg ctg tcc ttt gac tcc tgg ggc cag ggc acc ctg     336
Arg Ser Ala Trp Trp Leu Ser Phe Asp Ser Trp Gly Gln Gly Thr Leu
            100                 105                 110 gtg acc gtc tcc agc gct agc acc aag ggc ccc agc gtg ttc ccc ctg     384
Val Thr Val Ser Ser Ala Ser Thr Lys Gly Pro Ser Val Phe Pro Leu

```
                  115                 120                 125
gcc ccc agc agc aag agc acc agc ggc ggc aca gcc gcc ctg ggc tgc     432
Ala Pro Ser Ser Lys Ser Thr Ser Gly Gly Thr Ala Ala Leu Gly Cys
    130                 135                 140 ctg gtg aag gac tac ttc ccc gag ccc gtg acc gtg agc tgg aac agc     480
Leu Val Lys Asp Tyr Phe Pro Glu Pro Val Thr Val Ser Trp Asn Ser
145                 150                 155                 160 ggc gcc ttg acc agc ggc gtg cac acc ttc ccc gcc gtg ctg cag agc     528
Gly Ala Leu Thr Ser Gly Val His Thr Phe Pro Ala Val Leu Gln Ser
                165                 170                 175 agc ggc ctg tac agc ctg agc agc gtg gtg acc gtg ccc agc agc agc     576
Ser Gly Leu Tyr Ser Leu Ser Ser Val Val Thr Val Pro Ser Ser Ser
            180                 185                 190 ctg ggc acc cag acc tac atc tgc aac gtg aac cac aag ccc agc aac     624
Leu Gly Thr Gln Thr Tyr Ile Cys Asn Val Asn His Lys Pro Ser Asn
        195                 200                 205 acc aag gtg gac aaa cgc gtg gag ccc aag agc tgc gac aag acc cac     672
Thr Lys Val Asp Lys Arg Val Glu Pro Lys Ser Cys Asp Lys Thr His
    210                 215                 220 acc tgc ccc ccc tgc cct gcc ccc gag ctg ctg ggc gga ccc tcc gtg     720
Thr Cys Pro Pro Cys Pro Ala Pro Glu Leu Leu Gly Gly Pro Ser Val
225                 230                 235                 240 ttc ctg ttc ccc ccc aag ccc aag gac acc ctc atg atc agc cgg acc     768
Phe Leu Phe Pro Pro Lys Pro Lys Asp Thr Leu Met Ile Ser Arg Thr
                245                 250                 255 ccc gag gtg acc tgc gtg gtg gtg gac gtg agc cac gag gac ccc gag     816
Pro Glu Val Thr Cys Val Val Val Asp Val Ser His Glu Asp Pro Glu
            260                 265                 270 gtg aag ttc aac tgg tac gtg gac ggc gtg gag gtg cac aac gcc aag     864
Val Lys Phe Asn Trp Tyr Val Asp Gly Val Glu Val His Asn Ala Lys
        275                 280                 285 acc aag ccc cgg gag gag cag tac aac agc acc tac cgg gtg gtg agc     912
Thr Lys Pro Arg Glu Glu Gln Tyr Asn Ser Thr Tyr Arg Val Val Ser
    290                 295                 300 gtg ctc acc gtg ctg cac cag gac tgg ctg aac ggc aag gag tac aag     960
Val Leu Thr Val Leu His Gln Asp Trp Leu Asn Gly Lys Glu Tyr Lys
305                 310                 315                 320 tgc aag gtg agc aac aag gcc ctg cct gcc ccc atc gag aag acc atc    1008
Cys Lys Val Ser Asn Lys Ala Leu Pro Ala Pro Ile Glu Lys Thr Ile
                325                 330                 335 agc aag gcc aag ggc cag ccc cgg gag ccc cag gtg tac acc ctg ccc    1056
Ser Lys Ala Lys Gly Gln Pro Arg Glu Pro Gln Val Tyr Thr Leu Pro
            340                 345                 350 ccc agc cgg gag gag atg acc aag aac cag gtg tcc ctc acc tgt ctg    1104
Pro Ser Arg Glu Glu Met Thr Lys Asn Gln Val Ser Leu Thr Cys Leu
        355                 360                 365 gtg aag ggc ttc tac ccc agc gac atc gcc gtg gag tgg gag agc aac    1152
Val Lys Gly Phe Tyr Pro Ser Asp Ile Ala Val Glu Trp Glu Ser Asn
    370                 375                 380 ggc cag ccc gag aac aac tac aag acc acc ccc cct gtg ctg gac agc    1200
Gly Gln Pro Glu Asn Asn Tyr Lys Thr Thr Pro Pro Val Leu Asp Ser
385                 390                 395                 400 gac ggc agc ttc ttc ctg tac agc aag ctc acc gtg gac aag agc cgg    1248
Asp Gly Ser Phe Phe Leu Tyr Ser Lys Leu Thr Val Asp Lys Ser Arg
                405                 410                 415 tgg cag cag ggc aac gtg ttc agc tgc agc gtg atg cac gag gcc ctg    1296
Trp Gln Gln Gly Asn Val Phe Ser Cys Ser Val Met His Glu Ala Leu
            420                 425                 430 cac aac cac tac acc cag aag agc ctg agc ctg agc ccc ggc aag        1341
```

His Asn His Tyr Thr Gln Lys Ser Leu Ser Leu Ser Pro Gly Lys
            435                 440                 445

<210> SEQ ID NO 61
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chemically synthesized - Heavy chain of 02-118

<400> SEQUENCE: 61

Glu Val Gln Leu Val Glu Ser Gly Gly Gly Leu Val His Pro Gly Gly
1               5                   10                  15

Ser Leu Arg Leu Ser Cys Ala Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Ser Thr Gly Gly Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Ser Ala Trp Trp Leu Ser Phe Asp Ser Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

```
Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 62
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Chemically synthesized - Light chain of 02-113,
      02-114, 02-116, 02-117 and 02-118
<220> FEATURE:
<221> NAME/KEY: CDS
<222> LOCATION: (1)..(642)

<400> SEQUENCE: 62 gac att cag atg acc cag tct cca tcc tcc ctg tct gca tct gta gga         48
Asp Ile Gln Met Thr Gln Ser Pro Ser Ser Leu Ser Ala Ser Val Gly
1               5                   10                  15 gac aga gtc acc atc act tgc cgg gca agt cag agc att agc agc tac         96
Asp Arg Val Thr Ile Thr Cys Arg Ala Ser Gln Ser Ile Ser Ser Tyr
            20                  25                  30 tta aat tgg tat cag cag aaa cca ggg aaa gcc cct aag ctc ctg atc        144
Leu Asn Trp Tyr Gln Gln Lys Pro Gly Lys Ala Pro Lys Leu Leu Ile
        35                  40                  45 tat gct gca tcc agt ttg caa agt ggg gtc cca tca agg ttc agt ggc        192
Tyr Ala Ala Ser Ser Leu Gln Ser Gly Val Pro Ser Arg Phe Ser Gly
    50                  55                  60 agt gga tct ggg aca gat ttc act ctc acc atc agc agt ctg caa cct        240
Ser Gly Ser Gly Thr Asp Phe Thr Leu Thr Ile Ser Ser Leu Gln Pro
65                  70                  75                  80 gaa gat ttt gca act tac tac tgt caa cag agt tac agt acc cct cca        288
Glu Asp Phe Ala Thr Tyr Tyr Cys Gln Gln Ser Tyr Ser Thr Pro Pro
                85                  90                  95 acg ttc ggc caa ggg acc aag gtg gag atc aaa cgg acc gtg gct gct        336
Thr Phe Gly Gln Gly Thr Lys Val Glu Ile Lys Arg Thr Val Ala Ala
            100                 105                 110 ccc agc gtg ttc atc ttc ccc ccc tcc gac gag cag ctg aag agc ggc        384
Pro Ser Val Phe Ile Phe Pro Pro Ser Asp Glu Gln Leu Lys Ser Gly
        115                 120                 125 acc gcc agc gtg gtg tgc ctg ctg aac aac ttc tac ccc cgg gag gcc        432
Thr Ala Ser Val Val Cys Leu Leu Asn Asn Phe Tyr Pro Arg Glu Ala
    130                 135                 140 aag gtg cag tgg aag gtg gac aac gcc ctg cag agc ggc aac agc cag        480
Lys Val Gln Trp Lys Val Asp Asn Ala Leu Gln Ser Gly Asn Ser Gln
145                 150                 155                 160 gag agc gtg acc gag cag gac agc aag gac tcc acc tac agc ctg agc        528
Glu Ser Val Thr Glu Gln Asp Ser Lys Asp Ser Thr Tyr Ser Leu Ser
```

```
Glu Ser Val Thr Glu Gln Asp Ser Lys Asp Ser Thr Tyr Ser Leu Ser
            165                 170                 175 agc acc ctc acc ctg agc aag gcc gac tac gag aag cac aag gtg tac       576
Ser Thr Leu Thr Leu Ser Lys Ala Asp Tyr Glu Lys His Lys Val Tyr
            180                 185                 190 gcc tgc gag gtg acc cac cag ggc ctg agc agc ccc gtg acc aag agc       624
Ala Cys Glu Val Thr His Gln Gly Leu Ser Ser Pro Val Thr Lys Ser
            195                 200                 205 ttc aac cgg ggc gag tgt                                               642
Phe Asn Arg Gly Glu Cys
        210
```

<210> SEQ ID NO 63
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Chemically synthesized - Light chain of 02-113, 02-114, 02-116, 02-117 and 02-118

<400> SEQUENCE: 63

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 64
<211> LENGTH: 696
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Chemically synthesized - Light chain of 02-115
<220> FEATURE:
<221> NAME/KEY: CDS
<222> LOCATION: (1)..(696)

<400> SEQUENCE: 64

```
tcc tcc gag ctg acc cag gac cct gct gtg tct gtg gcc ttg gga cag       48
Ser Ser Glu Leu Thr Gln Asp Pro Ala Val Ser Val Ala Leu Gly Gln
1               5                  10                  15 aca gtc agg atc aca tgc caa gga gac agc ctc aga agc tat tat gca       96
Thr Val Arg Ile Thr Cys Gln Gly Asp Ser Leu Arg Ser Tyr Tyr Ala
             20                  25                  30 agc tgg tac cag cag aag cca gga cag gcc cct gta ctt gtc atc tat      144
Ser Trp Tyr Gln Gln Lys Pro Gly Gln Ala Pro Val Leu Val Ile Tyr
         35                  40                  45 ggt aaa aac aac cgg ccc tca ggg atc cca gac cga ttc tct ggc tcc      192
Gly Lys Asn Asn Arg Pro Ser Gly Ile Pro Asp Arg Phe Ser Gly Ser
     50                  55                  60 agc tca gga aac aca gct tcc ttg acc atc act ggg gct cag gcg gaa      240
Ser Ser Gly Asn Thr Ala Ser Leu Thr Ile Thr Gly Ala Gln Ala Glu
65                  70                  75                  80 gat gag gct gac tat tac tgt aac tcc cgg gac agc agt ggt aac cat      288
Asp Glu Ala Asp Tyr Tyr Cys Asn Ser Arg Asp Ser Ser Gly Asn His
                 85                  90                  95 gtg gta ttc ggc gga ggg acc aag ctg acc gtc cta ggt gag tcg cgg      336
Val Val Phe Gly Gly Gly Thr Lys Leu Thr Val Leu Gly Glu Ser Arg
            100                 105                 110 ccg caa gct tac cgt gct ggg cca gcc caa ggc cgc tcc cag cgt gac      384
Pro Gln Ala Tyr Arg Ala Gly Pro Ala Gln Gly Arg Ser Gln Arg Asp
        115                 120                 125 cct gtt ccc ccc ctc ctc cga gga gct gca ggc caa caa ggc cac cct      432
Pro Val Pro Pro Leu Leu Arg Gly Ala Ala Gly Gln Gln Gly His Pro
    130                 135                 140 ggt gtg cct cat cag cga ctt cta ccc tgg cgc cgt gac cgt ggc ctg      480
Gly Val Pro His Gln Arg Leu Leu Pro Trp Arg Arg Asp Arg Gly Leu
145                 150                 155                 160 gaa ggc cga cag cag ccc cgt gaa ggc cgg cgt gga gac cac cac ccc      528
Glu Gly Arg Gln Gln Pro Arg Glu Gly Arg Arg Gly Asp His His Pro
                165                 170                 175 cag caa gca gag caa caa caa gta cgc cgc cag cag cta cct gag cct      576
Gln Gln Ala Glu Gln Gln Gln Val Arg Arg Gln Gln Leu Pro Glu Pro
            180                 185                 190 cac ccc cga gca gtg gaa gag cca ccg gag cta cag ctg cca ggt gac      624
His Pro Arg Ala Val Glu Glu Pro Pro Glu Leu Gln Leu Pro Gly Asp
        195                 200                 205 cca cga ggg cag cac cgt gga gaa gac cgt ggc ccc cac cga gtg cag      672
Pro Arg Gly Gln His Arg Gly Glu Asp Arg Gly Pro His Arg Val Gln
    210                 215                 220 cta ata gac tta agt tta aac cgc                                      696
Leu Ile Asp Leu Ser Leu Asn Arg
225                 230
```

<210> SEQ ID NO 65
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chemically synthesized - Light chain of 02-115

-continued

```
<400> SEQUENCE: 65

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu Gly Glu Ser Arg
            100                 105                 110

Pro Gln Ala Tyr Arg Ala Gly Pro Ala Gln Gly Arg Ser Gln Arg Asp
        115                 120                 125

Pro Val Pro Pro Leu Leu Arg Gly Ala Ala Gly Gln Gln Gly His Pro
    130                 135                 140

Gly Val Pro His Gln Arg Leu Leu Pro Trp Arg Arg Asp Arg Gly Leu
145                 150                 155                 160

Glu Gly Arg Gln Gln Pro Arg Glu Gly Arg Arg Gly Asp His His Pro
                165                 170                 175

Gln Gln Ala Glu Gln Gln Gln Val Arg Arg Gln Leu Pro Glu Pro
            180                 185                 190

His Pro Arg Ala Val Glu Glu Pro Glu Leu Gln Leu Pro Gly Asp
        195                 200                 205

Pro Arg Gly Gln His Arg Gly Glu Asp Arg Gly Pro His Arg Val Gln
    210                 215                 220

Leu Ile Asp Leu Ser Leu Asn Arg
225                 230

<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized - HCDR1 of SC02-113

<400> SEQUENCE: 66

Gly Tyr Tyr Trp Ser
1               5

<210> SEQ ID NO 67
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized - HCDR2 of SC02-113

<400> SEQUENCE: 67

Tyr Ile Tyr Tyr Ser Gly Ser Thr Asn Tyr Asn Pro Ser Leu Lys Ser
1               5                   10                  15
```

-continued

<210> SEQ ID NO 68
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized - LCDR1 of SC02-113 and
      SC02-118

<400> SEQUENCE: 68

Arg Ala Ser Gln Ser Ile Ser Ser Tyr Leu Asn
1               5                   10

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized - LCDR2 of SC02-113 and
      SC02-118

<400> SEQUENCE: 69

Ala Ala Ser Ser Leu Gln Ser
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized - LCDR3 of SC02-113 and
      SC02-118

<400> SEQUENCE: 70

Gln Gln Ser Tyr Ser Thr Pro
1               5

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized - HCDR1 of SC02-118

<400> SEQUENCE: 71

Ser Tyr Ala Met His
1               5

<210> SEQ ID NO 72
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Chemically synthesized - HCDR2 of SC02-118

<400> SEQUENCE: 72

```
Ala Ile Ser Thr Gly Gly Gly Thr Tyr Tyr Ala Asp Ser Val Lys Gly
1               5                   10                  15
```